US012479794B2

(12) United States Patent
Wu et al.

(10) Patent No.: US 12,479,794 B2
(45) Date of Patent: Nov. 25, 2025

(54) ACETOPHENONE OXIME COMPOUND AND APPLICATION THEREOF

(71) Applicant: Medshine Discovery Inc., Jiangsu (CN)

(72) Inventors: Lingyun Wu, Shanghai (CN); Lele Zhao, Shanghai (CN); Xinming Du, Shanghai (CN); Xu You, Shanghai (CN); Shuhui Chen, Shanghai (CN)

(73) Assignee: Medshine Discovery Inc., Jiangsu (CN)

( * ) Notice: Subject to any disclaimer, the term of this patent is extended or adjusted under 35 U.S.C. 154(b) by 460 days.

(21) Appl. No.: 18/022,194

(22) PCT Filed: Aug. 16, 2021

(86) PCT No.: PCT/CN2021/112753

§ 371 (c)(1),
(2) Date: Feb. 20, 2023

(87) PCT Pub. No.: WO2022/037525

PCT Pub. Date: Feb. 24, 2022

(65) Prior Publication Data

US 2023/0295076 A1 Sep. 21, 2023

(30) Foreign Application Priority Data

Aug. 20, 2020 (CN) ......................... 202010847864.2
Jan. 26, 2021 (CN) ......................... 202110109311.1
Jan. 28, 2021 (CN) ......................... 202110123369.1

(51) Int. Cl.
*C07C 251/50* (2006.01)
*A61P 9/10* (2006.01)

(52) U.S. Cl.
CPC .............. *C07C 251/50* (2013.01); *A61P 9/10* (2018.01)

(58) Field of Classification Search
CPC .............. C07C 251/50; C07C 2601/02; C07C 251/52; C07C 255/54; C07C 2601/08; C07C 2601/14; A61P 9/10
See application file for complete search history.

(56) References Cited

U.S. PATENT DOCUMENTS

2011/0053925 A1* 3/2011 Cho ..................... C07D 471/04 544/137

* cited by examiner

*Primary Examiner* — San Ming R Hui
(74) *Attorney, Agent, or Firm* — Wolf, Greenfield & Sacks, P.C.

(57) ABSTRACT

Disclosed are an acetophenone oxime compound and a preparation method therefor, and specifically disclosed are a compound as shown in formula (II) and a pharmaceutically acceptable salt thereof.

(II)

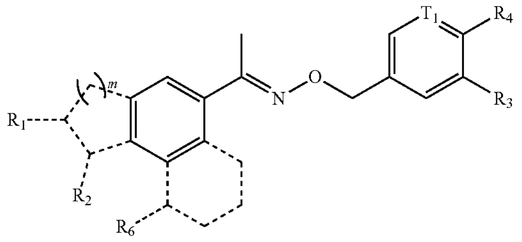

15 Claims, 1 Drawing Sheet

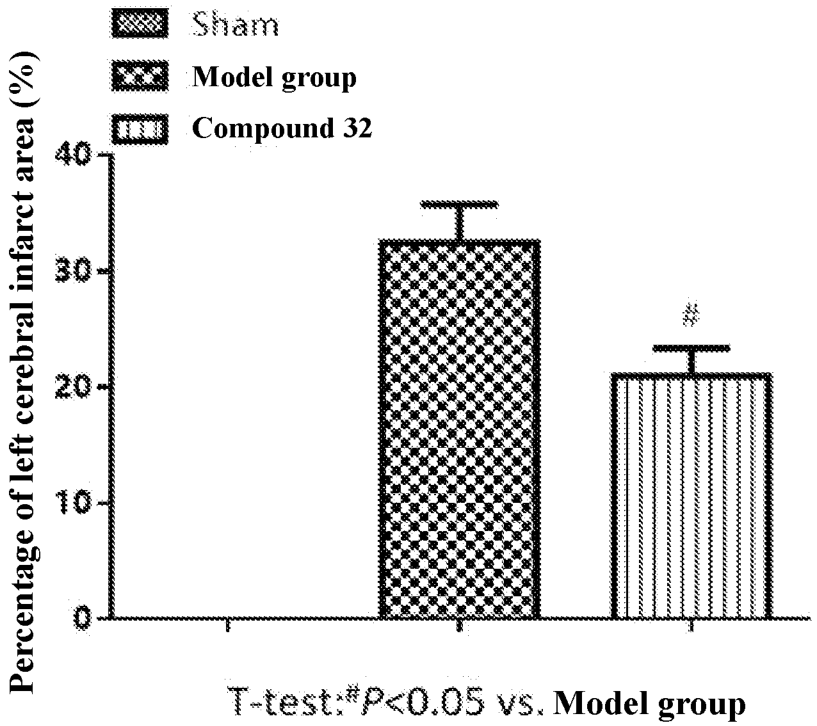
Sham
Model group
Compound 32
Percentage of left cerebral infarct area (%)
40
30
20
10
0

T-test: #P<0.05 vs. Model group

ACETOPHENONE OXIME COMPOUND AND APPLICATION THEREOF

REFERENCE TO RELATED APPLICATIONS

This application is a National Stage filing under 35 U.S.C. 371 of International PCT Application No. PCT/CN2021/112753, filed on Aug. 16, 2021, which claims the priority of CN202010847864.2, filed Aug. 20, 2020; CN202110109311.1, filed on Jan. 26, 2021; and CN202110123369.1, filed on Jan. 28, 2021. The Chinese Patent Application Nos. 202010847864.2, 202110109311.1, and 202110123369.1 are incorporated herein by reference as part of the disclosure of the present application.

FIELD OF THE INVENTION

The present disclosure relates to novel acetophenone oxime compounds and preparation methods thereof, in particular to a compound represented by formula (II) and a pharmaceutically acceptable salt thereof.

BACKGROUND OF THE INVENTION

Sphingosine-1-phosphate receptor (S1P) is a class of G protein-coupled receptor expressed on the surface of cell membranes of lymphocytes, glial cells, cardiovascular endothelial cells, etc., which regulates intrinsic and adaptive immune responses in the body by recognizing a class of sphingolipids with important biological functions, namely sphingosine-1-phosphate, and is involved in various physiological or pathological processes in the body, such as apoptosis, autophagy, lymphocyte migration, and release of inflammatory factors. Currently, five S1P subtypes have been found in mammals. $S1P_{1-3}$ is widely expressed in the central nervous system, immune system, and atrioventricular conduction system. $S1P_4$ is mainly expressed in the immune system, and $S1P_5$ is mainly expressed in the central nervous system. Studies have shown that $S1P_1$ agonists can induce $S1P_1$ endocytosis on the surface of lymphocytes, prevent lymphocytes from sensing S1P concentration gradients, prevent lymphocytes from migrating from secondary lymphoid organs (lymph nodes, etc.) to tissues, induce lymphocyte homing, reduce the number of lymphocytes in the peripheral circulatory system, prevent lymphocytes from reaching the site of inflammatory damage or grafts, reduce excessive inflammation, and have immunomodulatory effect.

Currently, three S1P agonists have been approved for marketing. Novartis' first-generation non-selective S1Ps ($S1P_1$, $S1P_3$, $S1P_4$, $S1P_5$) agonist Fingolimod was approved by the FDA in 2010 for the treatment of relapsing-remitting multiple sclerosis (RRMS), and the second-generation selective $S1P_1$ agonist Siponimod was approved by the FDA in 2019 for the treatment of relapsing-remitting multiple sclerosis (RRMS) and secondary progressive multiple sclerosis (SPMS). Bristol-Myers Squibb's second-generation selective $S1P_1$ agonist Ozanimod was approved by the FDA in 2020 for the treatment of relapsing-remitting multiple sclerosis (RRMS) and secondary progressive multiple sclerosis (SPMS). In addition, several $S1P_1$ agonists are in clinical studies for the treatment of autoimmune diseases such as systemic lupus erythematosus (SLE), ulcerative colitis (UC), Crohn's disease (CD), and psoriasis, and inflammatory stress injuries such as acute ischemic stroke (AIS) and hemorrhagic stroke (ICH). Therefore, the development of selective small molecule $S1P_1$ agonists has broad application prospects.

SUMMARY OF THE INVENTION

The present disclosure provides a compound represented by formula (II), or a pharmaceutically acceptable salt thereof, (II)

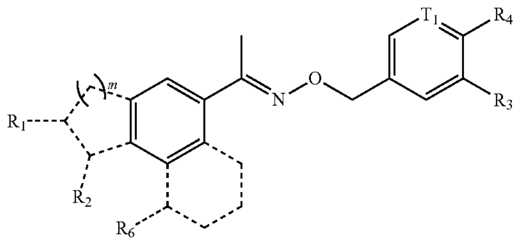

wherein the structural moiety

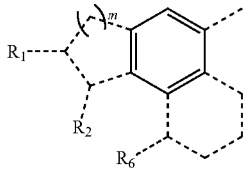

is selected from

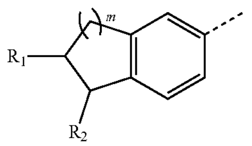

and

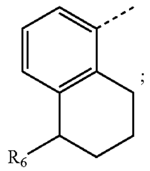

;

m is selected from 1 and 2;

$T_1$ is selected from $CR_5$ and N;

$R_1$ and $R_2$ are each independently selected from H, $-L_1-NR_a-L_2-COOH$, $-L_1-NR_a-L_2$-cyclopropyl, -azetidinyl-COOH and -piperidyl-COOH, wherein the $-L_1-NR_a-L_2-COOH$, $-L_1-NR_a-L_2$-cyclopropyl, -azetidinyl-COOH and -piperidyl-COOH are optionally substituted with 1, 2 or 3 $R_b$;

$L_1$ is selected from a single bond or $CH_2$;

$L_2$ is selected from $C_{1-3}$ alkyl;

$R_3$ and $R_5$ are each independently selected from H, F, Cl, Br, CN and $C_{1-3}$ alkyl, wherein the $C_{1-3}$ alkyl is optionally substituted with 1, 2 or 3 $R_c$;

$R_4$ is selected from —O—$C_{1-6}$ alkyl, —O—$C_{1-3}$ alkyl-cyclopropyl, —O—$C_{3-6}$ cycloalkyl and $C_{3-6}$ cycloalkyl, wherein the $C_{1-3}$ alkyl, $C_{1-6}$ alkyl and $C_{3-6}$ cycloalkyl are optionally substituted with 1, 2 or 3 $R_d$;

$R_6$ is selected from H and —$NR_a$—$C_{1-3}$ alkyl-COOH, wherein the —$NR_a$—$C_{1-3}$ alkyl-COOH is optionally substituted with 1, 2 or 3 $R_e$;

$R_a$ is selected from H and $CH_3$;

$R_b$ is selected from H, F, Cl, Br, I and COOH;

$R_c$ and $R_d$ are each independently selected from H, F, Cl, Br and I;

$R_e$ is each independently selected from H, F, Cl, Br and I.

In some embodiments of the present disclosure, the above $R_1$ is selected from H, —NH—$CH_2$—COOH and —NH—$CH_2CH_2$—COOH, and other variables are as defined in the present disclosure.

In some embodiments of the present disclosure, the above $L_2$ is selected from $CH_2$, $CH_2CH_2$, $CH(CH_2)_2$ and $CH_2CH_2CH_2$, and other variables are as defined in the present disclosure.

In some embodiments of the present disclosure, the above $R_2$ is selected from H, —NH—$CH_2$—COOH, —NH—$CH_2CH_2$—COOH, —N($CH_3$)—$CH_2CH_2$—COOH,

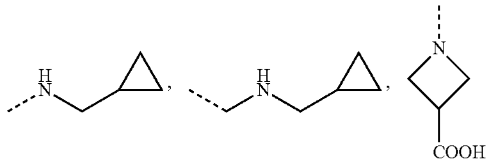

and

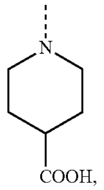

wherein the —NH—$CH_2$—COOH, —NH—$CH_2CH_2$—COOH, —N($CH_3$)—$CH_2CH_2$—COOH,

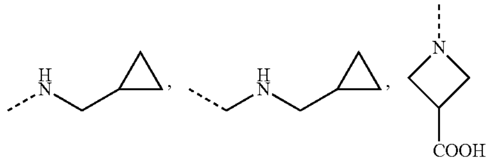

and

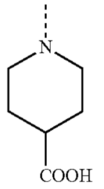

are optionally substituted with 1, 2 or 3 $R_b$, and other variables are as defined in the present disclosure.

In some embodiments of the present disclosure, the above $R_2$ is selected from H, —NH—$CH_2$—COOH, —NH—$CH_2CH_2$—COOH, —N($CH_3$)—$CH_2CH_2$—COOH,

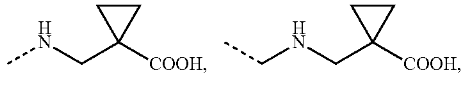

-continued

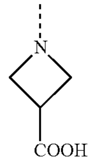

and

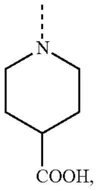

and other variables are as defined in the present disclosure.

In some embodiments of the present disclosure, the above $R_3$ is selected from H, F, Cl, Br, CN and $CF_3$, and other variables are as defined in the present disclosure.

In some embodiments of the present disclosure, the above $R_4$ is selected from —O—$C_{1-4}$ alkyl, —O—$C_{1-3}$ alkyl-cyclopropyl, —O-cyclopropyl, —O-cyclopentyl and cyclohexyl, wherein the —O—$C_{1-4}$ alkyl, —O—$C_{1-3}$ alkyl-cyclopropyl, —O-cyclopropyl, —O-cyclopentyl and cyclohexyl are optionally substituted with 1, 2 or 3 $R_d$, and other variables are as defined in the present disclosure.

In some embodiments of the present disclosure, the above $R_4$ is selected from

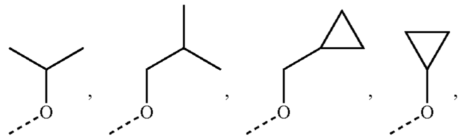

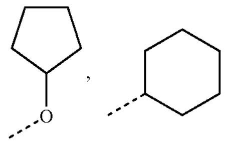

and

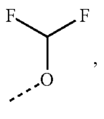

and other variables are as defined in the present disclosure.

In some embodiments of the present disclosure, the above $R_5$ is selected from H and F, and other variables are as defined in the present disclosure.

In some embodiments of the present disclosure, the above $R_6$ is selected from H, —NH—$CH_2$—COOH, —NH—$CH_2CH_2$—COOH, —N($CH_3$)—$CH_2CH_2$—COOH and —NH—$(CH_2)_3$—COOH, and other variables are as defined in the present disclosure.

In some embodiments, the present disclosure provides the above compound or a pharmaceutically acceptable salt thereof, wherein the compound is selected from (I)

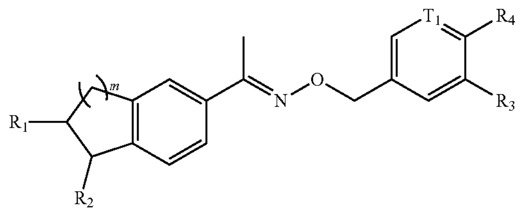

and

-continued (II-1)

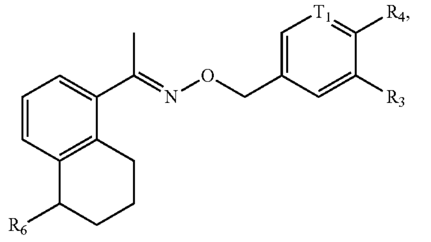

wherein m, $T_1$, $R_1$, $R_2$, $R_3$, $R_4$ and $R_6$ are as defined in the present disclosure.

In some embodiments, the present disclosure provides the above compound or a pharmaceutically acceptable salt thereof, wherein the compound is selected from (I-1)

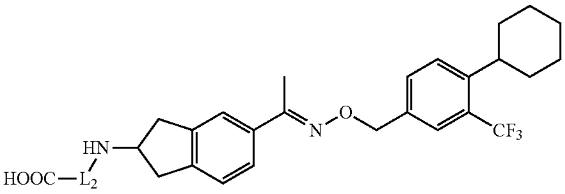

(I-2)

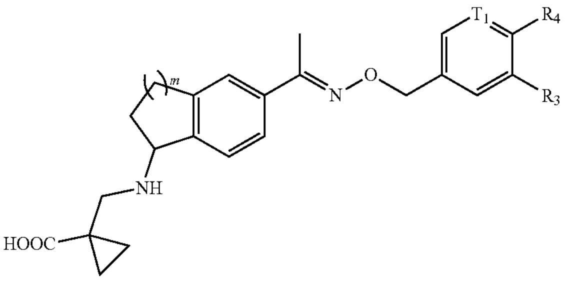

(I-3)

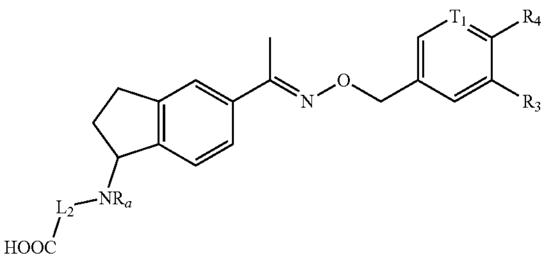

(II-1-1)

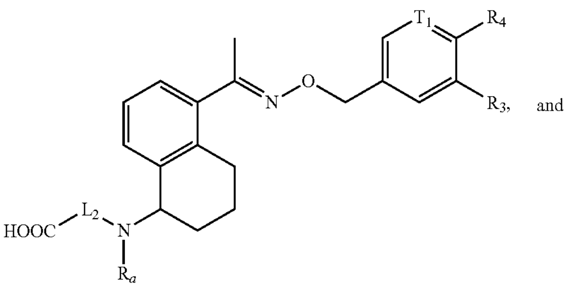

and

-continued (IV-1)

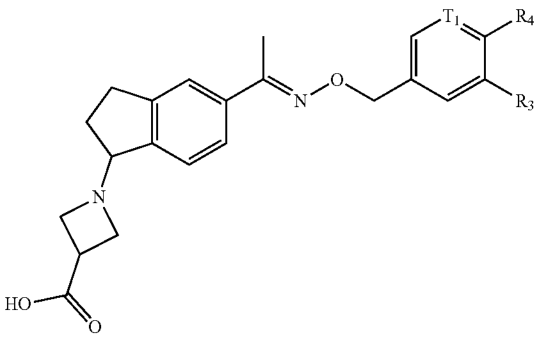

wherein $T_1$, $R_3$, $R_4$, $L_2$, m and $R_a$ are as defined in the present disclosure.

The present disclosure provides a compound represented by formula (I), or a pharmaceutically acceptable salt thereof, (I)

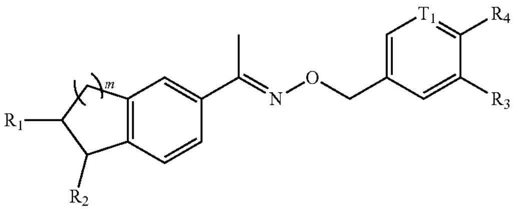

wherein m is selected from 1 and 2;

$T_1$ is selected from $CR_5$ and N;

$R_1$ and $R_2$ are each independently selected from H, $-L_1-NR_a-L_2$-COOH, $-L_1-NR_a-L_2$-cyclopropyl, -azetidinyl-COOH and -piperidyl-COOH, wherein the $-L_1-NR_a-L_2$-COOH, $-L_1-NR_a-L_2$-cyclopropyl, -azetidinyl-COOH and -piperidyl-COOH are optionally substituted with 1, 2 or 3 $R_b$;

$L_1$ is selected from a single bond or $CH_2$;

$L_2$ is selected from $C_{1-3}$ alkyl;

$R_3$ and $R_5$ are each independently selected from H, F, Cl, Br, CN and $C_{1-3}$ alkyl, wherein the $C_{1-3}$ alkyl is optionally substituted with 1, 2 or 3 $R_c$;

$R_4$ is selected from —O—$C_{1-6}$ alkyl, —O—$C_{1-3}$ alkyl-cyclopropyl, —O—$C_{3-6}$ cycloalkyl and $C_{3-6}$ cycloalkyl, wherein the $C_{1-3}$ alkyl, $C_{1-6}$ alkyl and $C_{3-6}$ cycloalkyl are optionally substituted with 1, 2 or 3 $R_d$;

$R_a$ is selected from H and $CH_3$;

$R_b$ is selected from H, F, Cl, Br, I and COOH;

$R_c$ and $R_d$ are each independently selected from H, F, Cl, Br and I.

In some embodiments of the present disclosure, the above $R_1$ is selected from H, —NH—$CH_2$—COOH and —NH—$CH_2CH_2$—COOH, and other variables are as defined in the present disclosure.

In some embodiments of the present disclosure, the above $L_2$ is selected from $CH_2$, $CH_2CH_2$, $CH(CH_2)_2$ and $CH_2CH_2CH_2$, and other variables are as defined in the present disclosure.

In some embodiments of the present disclosure, the above $R_2$ is selected from H, —NH—$CH_2$—COOH, —NH—$CH_2CH_2$—COOH, —$N(CH_3)$—$CH_2CH_2$—COOH,

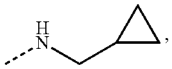 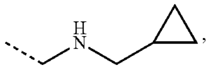 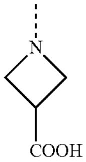 and

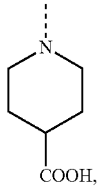

wherein the —NH—$CH_2$—COOH, —NH—$CH_2CH_2$—COOH, —N($CH_3$)—$CH_2CH_2$—COOH,

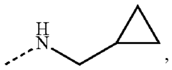 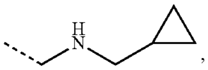

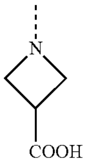 and 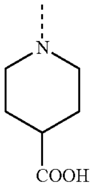

are optionally substituted with 1, 2 or 3 $R_b$, and other variables are as defined in the present disclosure.

In some embodiments of the present disclosure, the above $R_2$ is selected from H, —NH—$CH_2$—COOH, —NH—$CH_2CH_2$—COOH, —N($CH_3$)—$CH_2CH_2$—COOH,

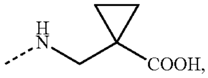 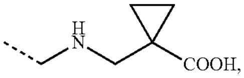

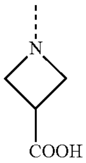 and 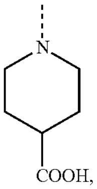

and other variables are as defined in the present disclosure.

In some embodiments of the present disclosure, the above $R_3$ is selected from H, F, Cl, Br, CN and $CF_3$, and other variables are as defined in the present disclosure.

In some embodiments of the present disclosure, the above $R_4$ is selected from —O—$C_{1-4}$ alkyl, —O—$C_{1-3}$ alkyl-cyclopropyl, —O-cyclopropyl, —O-cyclopentyl and cyclohexyl, wherein the —O—$C_{1-4}$ alkyl, —O—$C_{1-3}$ alkyl-cyclopropyl, —O-cyclopropyl, —O-cyclopentyl and cyclohexyl are optionally substituted with 1, 2 or 3 $R_d$, and other variables are as defined in the present disclosure.

In some embodiments of the present disclosure, the above $R_4$ is selected from

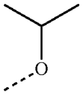, 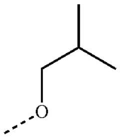, 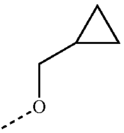, 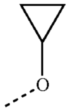,

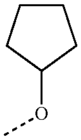 and 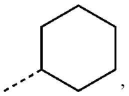, and other variables are as defined in the present disclosure.

In some embodiments of the present disclosure, the above $R_5$ is selected from H and F, and other variables are as defined in the present disclosure.

The present disclosure also includes some embodiments obtained by any combination of the above variables.

The present disclosure provides the following compounds or pharmaceutically acceptable salts thereof,

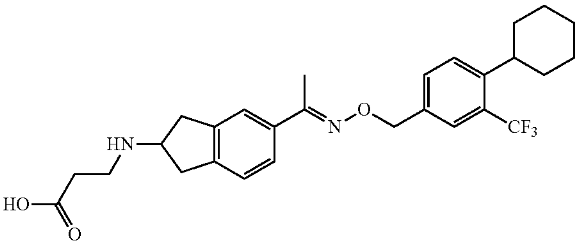

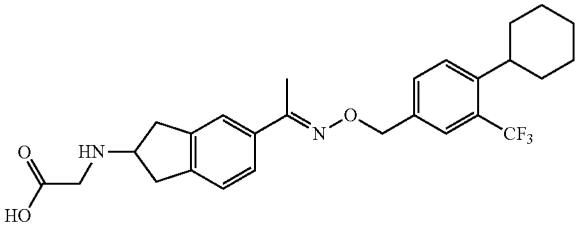

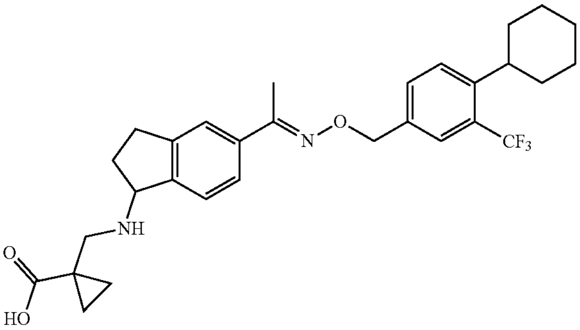

-continued
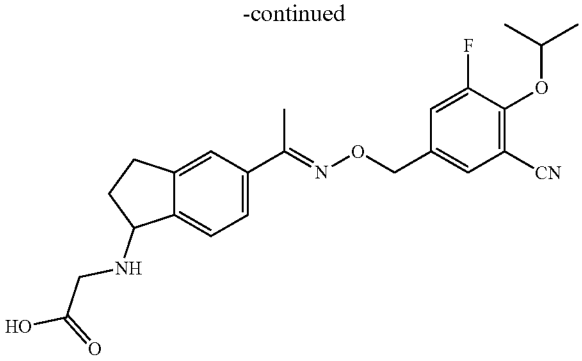
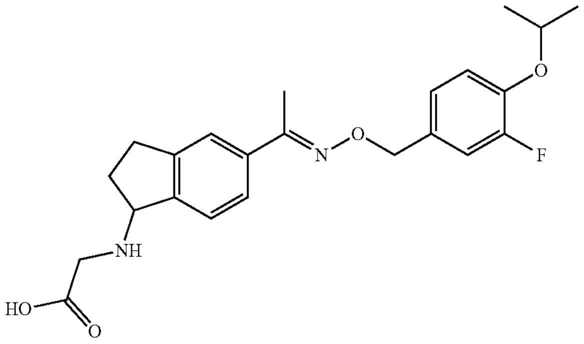
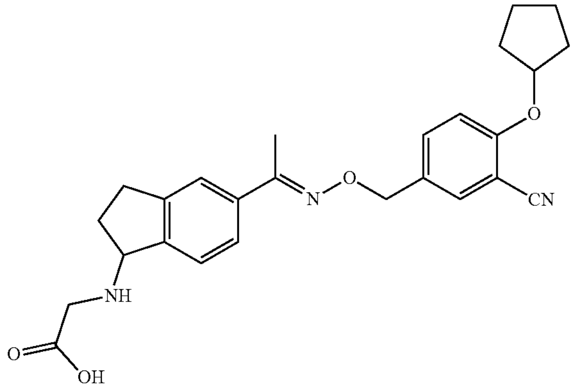
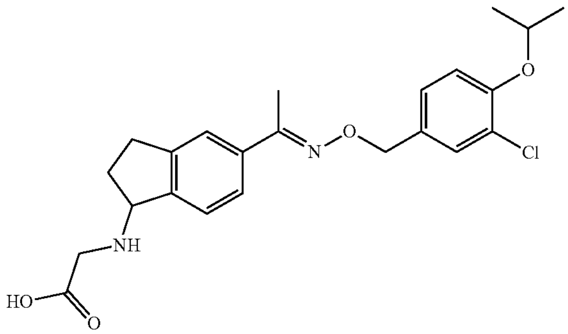
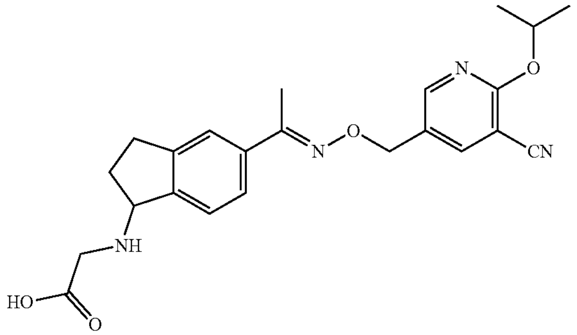
-continued
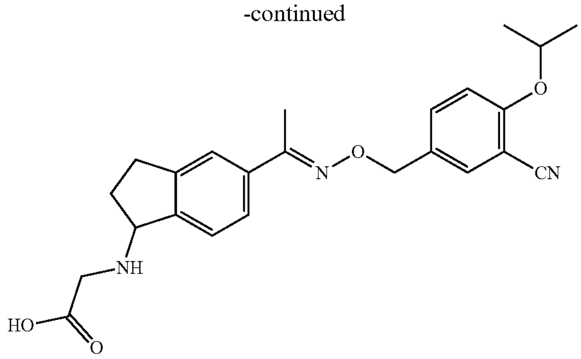
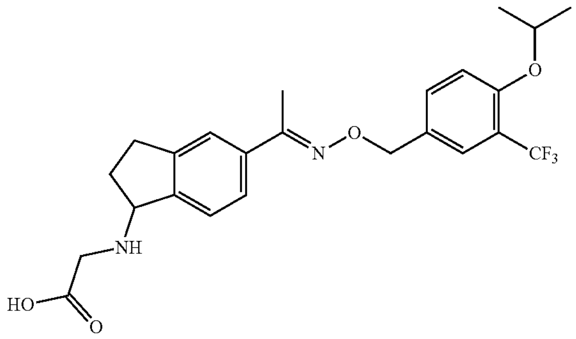
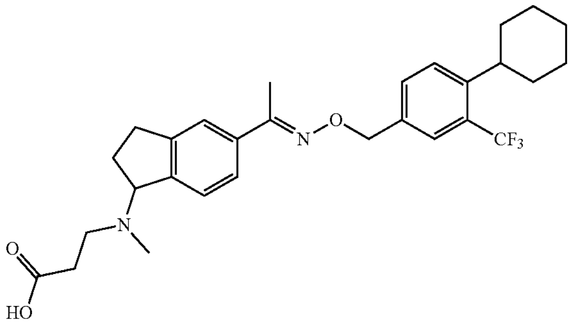
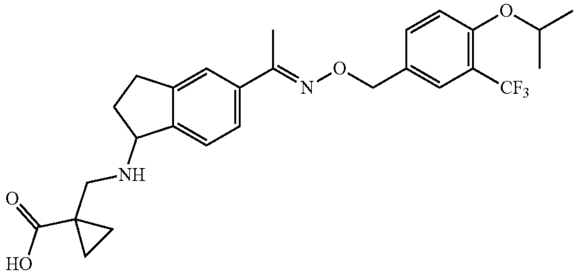
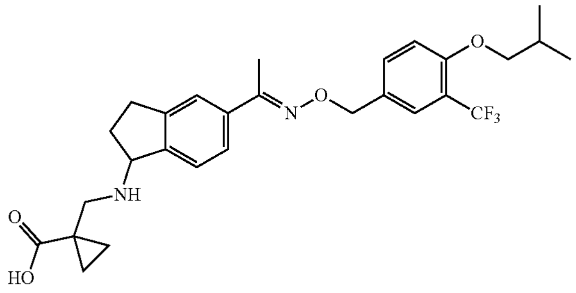

-continued
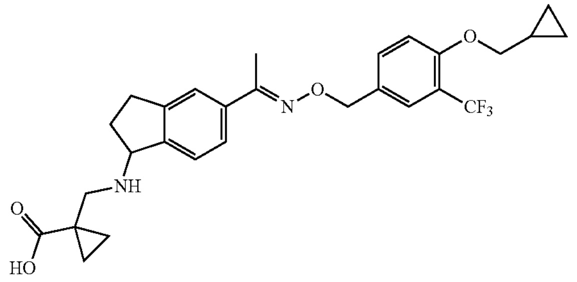
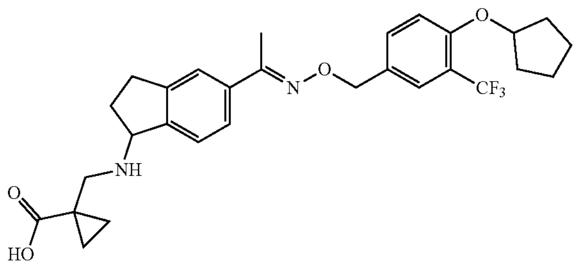
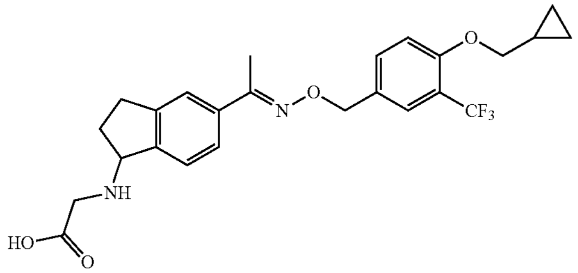
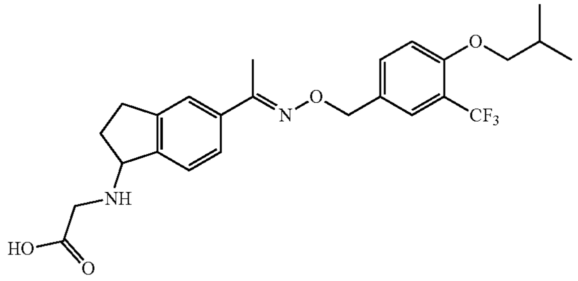
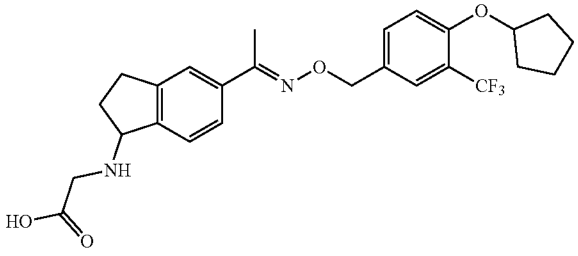
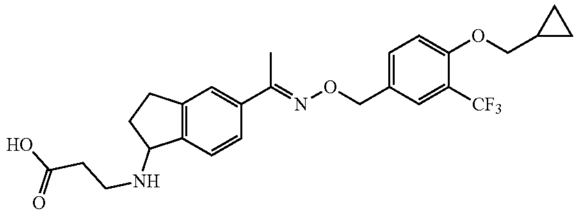
-continued
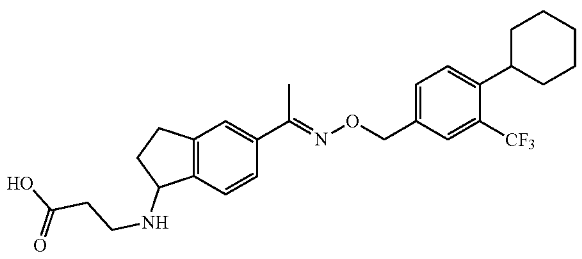
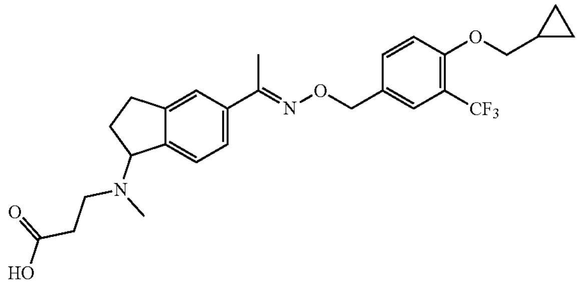
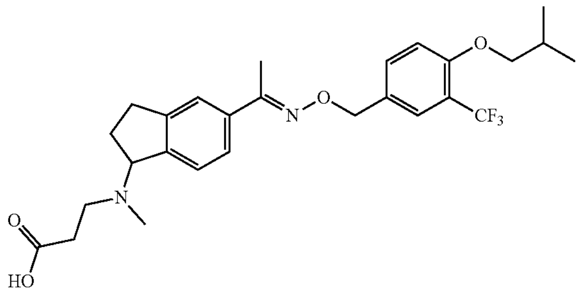
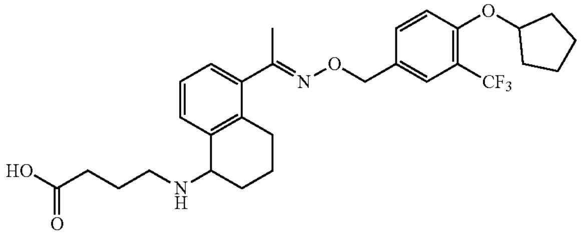
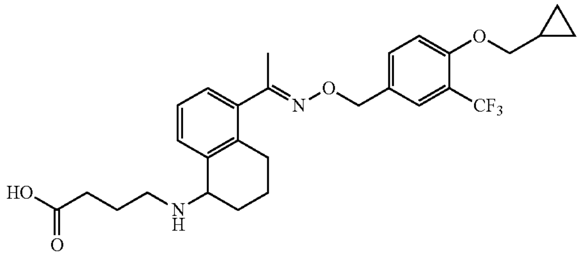
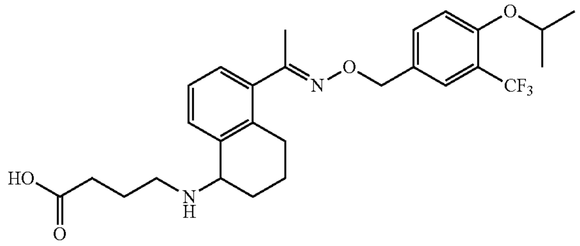

-continued
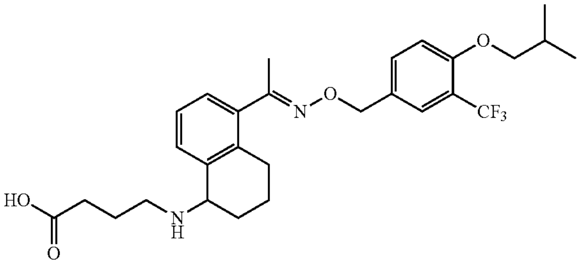
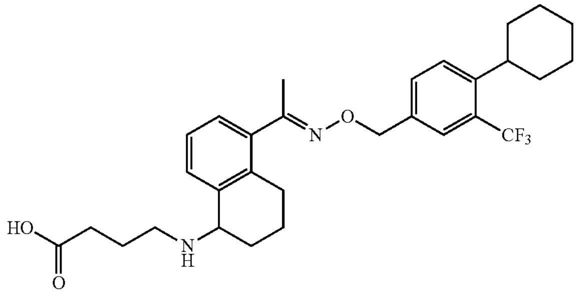
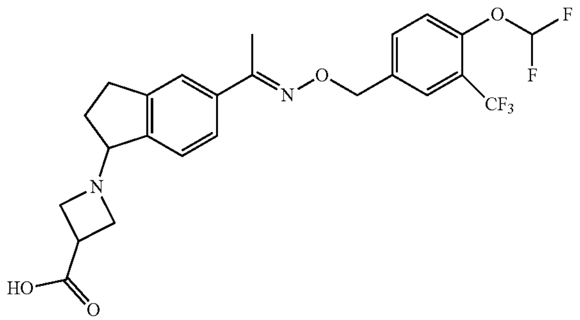
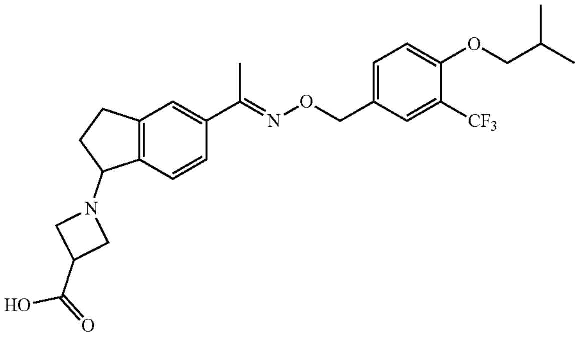
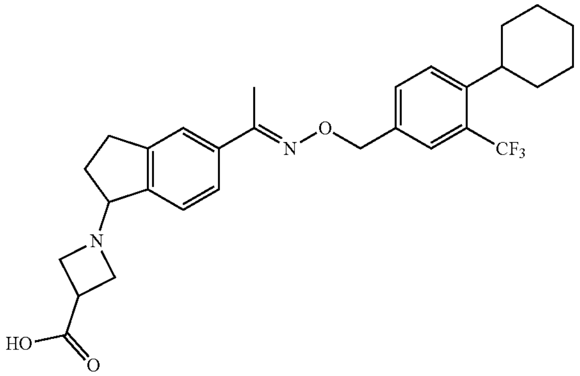
-continued
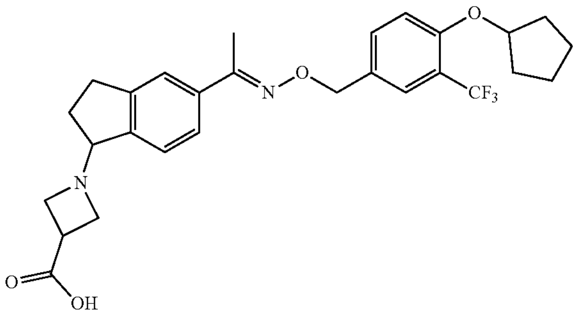
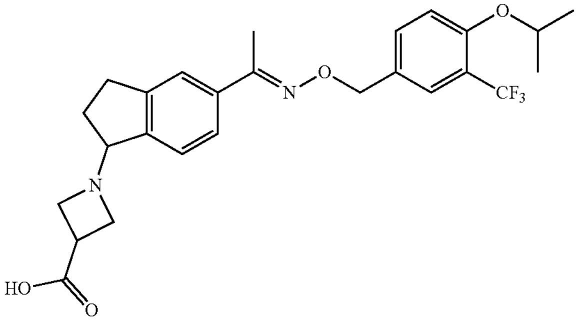
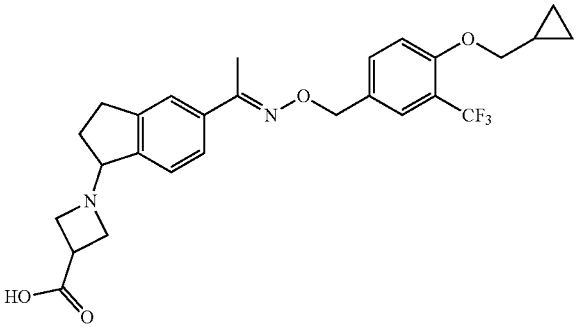
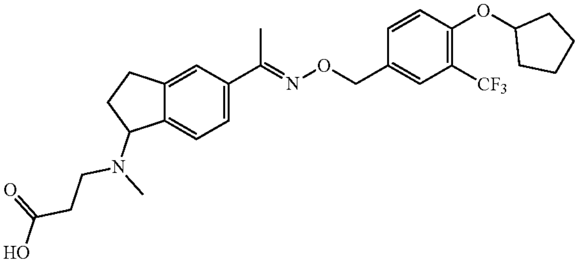
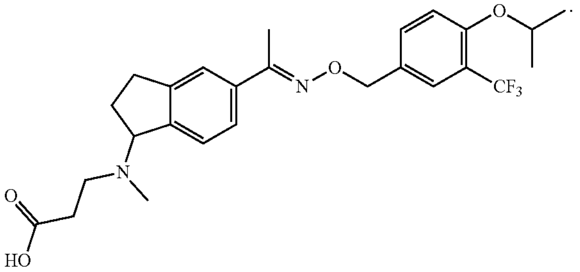
In some embodiments, the present disclosure provides the above compound or a pharmaceutically acceptable salt thereof, wherein the compound is selected from

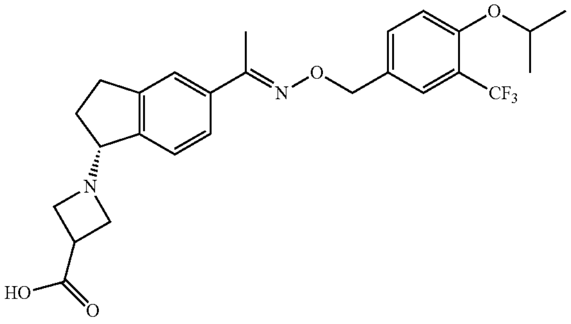
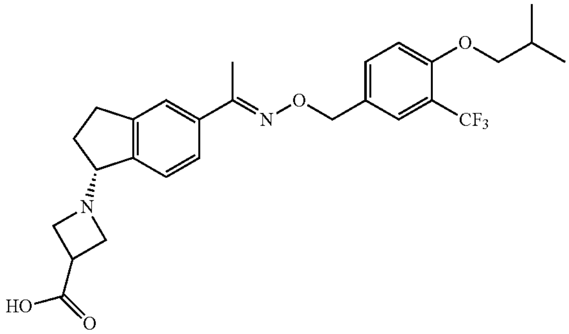
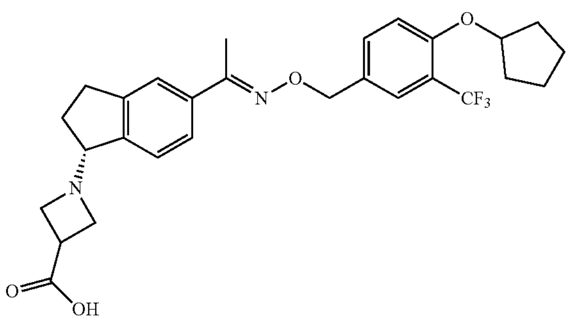
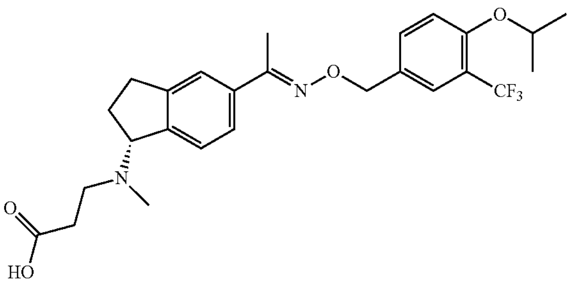
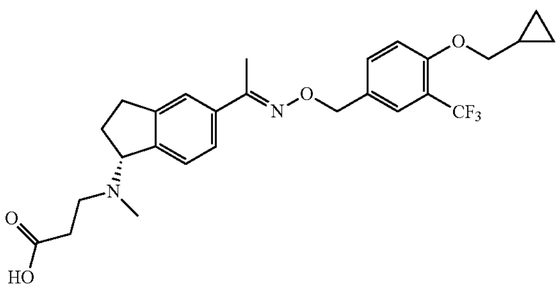
-continued
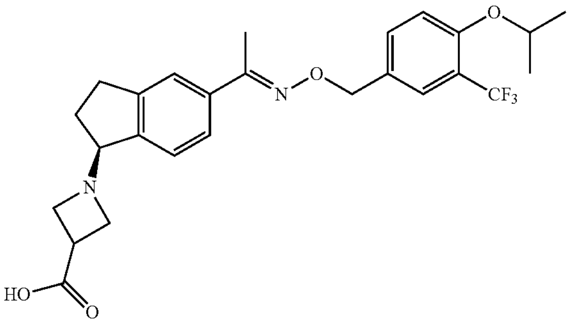
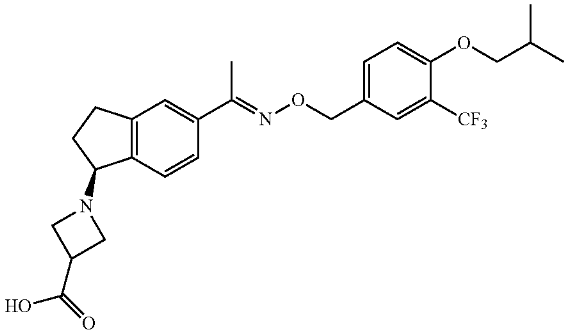
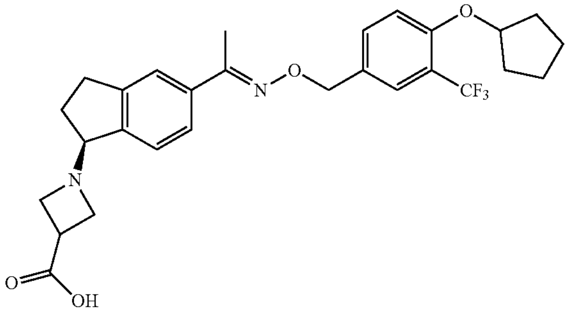
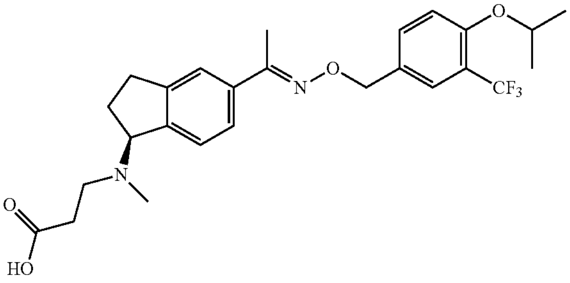
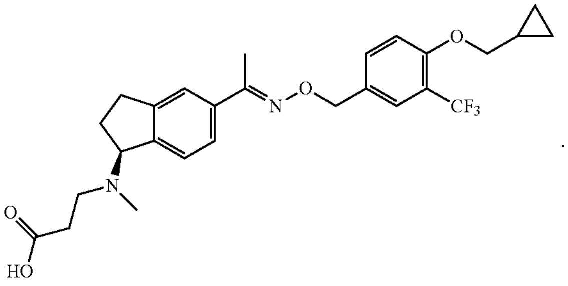
The present disclosure also provides use of the above compound or a pharmaceutically acceptable salt thereof in the manufacture of a medicament for the treatment of ischemic stroke.

Technical Effects

The compound of the present disclosure has remarkable selective $S1P_1$ agonistic activity and good pharmacokinetic properties, can improve area of cerebral infarction in an ischemia-reperfusion model, and has good metabolic stability.

Definition and Term

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Compounds disclosed herein may be present in a specific geometric or stereoisomeric form. The present disclosure contemplates all such compounds, including cis and trans isomers, (−)- and (+)-enantiomers, (R)- and (S)-enantiomers, diastereoisomer, (D)-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Compounds disclosed herein may contain an unnatural proportion of atomic isotopes at one or more of the atoms that make up the compounds. For example, a compound may be labeled with a radioisotope such as tritium ($^3H$), iodine-125 ($^{125}I$) or C-14($^{14}C$). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means that one or more than one hydrogen atoms on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary so long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of variables is a single bond, it means that the two groups linked by the single bond are connected directly. For example, when L in A-L-Z represents a single bond, the structure of A-L-Z is actually A-Z.

Unless otherwise specified, when a group has one or more connectable sites, any one or more sites of the group can be connected to other groups through chemical bonds. Where the connection position of the chemical bond is variable, and there is H atom(s) at a connectable site(s), when the connectable site(s) having H atom(s) is connected to the chemical bond, the number of H atom(s) at this site will correspondingly decrease as the number of the connected chemical bond increases, and the group will become a group of corresponding valence. The chemical bond between the site and other groups can be represented by a straight solid bond (), a straight dashed bond (), or a wavy line

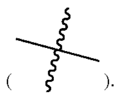

For example, the straight solid bond in —$OCH_3$ indicates that the group is connected to other groups through the oxygen atom in the group; the straight dashed bond in

indicates that the group is connected to other groups through two ends of the nitrogen atom in the group; the wavy line in

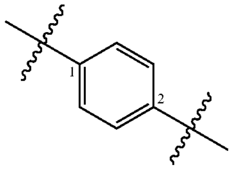 [SMILES: *c1ccc(*)cc1]

indicates that the group is connected to other groups through the 1- and 2-carbon atoms in the phenyl group;

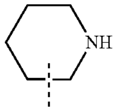

indicates that any connectable site on the piperidinyl group can be connected to other groups through one chemical bond, including at least four connection ways,

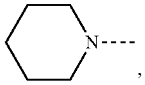 , 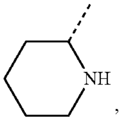 , 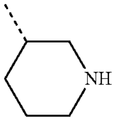 and 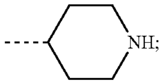 ;

even if a H atom is drawn on —N—,

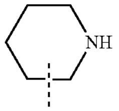

still includes the connection way of

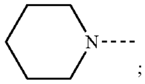 ;

it's just that when one chemical bond is connected, the H at this site will be reduced by one, and the group will become the corresponding monovalent piperidinyl group.

Unless otherwise specified, the term "$C_{1-6}$ alkyl" is used to represent a linear or branched saturated hydrocarbon group composed of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc. It may be monovalent (such as methyl), divalent (such as methylene) or multivalent (such as methenyl). Examples of the $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, and the like.

Unless otherwise specified, the term "$C_{1-4}$ alkyl" is used to represent a linear or branched saturated hydrocarbon group composed of 1 to 4 carbon atoms. The $C_{1-4}$ alkyl includes $C_{1-2}$, $C_{1-3}$, and $C_{2-3}$ alkyl, etc. It may be monovalent (such as methyl), divalent (such as methylene) or multivalent (such as methenyl). Examples of the $C_{1-4}$ alkyl include, but are not limited to, methyl (Me), ethyl (Et), propyl (including n-propyl and isopropyl), butyl (including n-butyl, isobutyl, s-butyl and t-butyl), and the like.

Unless otherwise specified, the term "$C_{1-3}$ alkyl" is used to represent a linear or branched saturated hydrocarbon group composed of 1 to 3 carbon atoms. The $C_{1-3}$ alkyl includes $C_{1-2}$ alkyl, $C_{2-3}$ alkyl, etc. It may be monovalent (such as methyl), divalent (such as methylene) or multivalent (such as methenyl). Examples of the $C_{1-3}$ alkyl include, but are not limited to, methyl (Me), ethyl (Et), propyl (including n-propyl and isopropyl), and the like.

Unless otherwise specified, "$C_{3-6}$ cycloalkyl" is used to refer to a saturated cyclic hydrocarbon group composed of 3 to 6 carbon atoms, which is a single ring system. The $C_{3-6}$ cycloalkyl includes $C_{3-5}$, $C_{4-5}$, and $C_{5-6}$ cycloalkyl and the like. It may be monovalent, divalent or multivalent. Examples of $C_{3-6}$ cycloalkyl groups include, but are not limited to, cyclopropyl, cyclobutyl, cyclopentyl, cyclohexyl, etc.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc.; similarly, n membered to n+m membered indicates that the number of atoms on a ring is n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, also includes any range from n to n+m, for example, 3-12 membered ring includes 3-6 membered ring, 3-9 membered ring, 5-6 membered ring, 5-7 membered ring, 6-7 membered ring, 6-8 membered ring, and 6-10 membered ring, and the like.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

Solvents used in the present disclosure are commercially available.

Compounds are named according to general naming principles in the art or by ChemDraw® software, and commercially available compounds are named with their vendor directory names.

BRIEF DESCRIPTION OF THE DRAWINGS

FIG. 1 is a graph of percentage cerebral infarction.

DETAILED DESCRIPTION OF THE INVENTION

The present disclosure is described in detail below by way of examples, but the examples are not intended to impose any unfavorable limitation on the present disclosure. The compounds of the present disclosure can be prepared by a variety of synthetic methods well known to those skilled in the art, including the specific embodiment listed below, embodiments formed by the specific embodiment listed below in combination with other chemical synthetic methods, and equivalents well known to those skilled in the art. Alternative embodiments include, but are not limited to, the examples of the present disclosure. It will be apparent to those skilled in the art that various changes and modifications can be made to the specific embodiments of the present disclosure without departing from the spirit and scope of the present disclosure.

Intermediate A

A

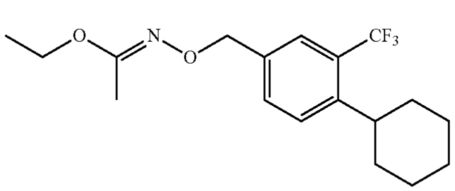

Synthetic Route:

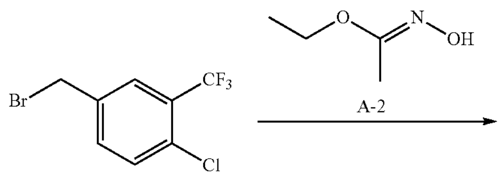

A-1

-continued

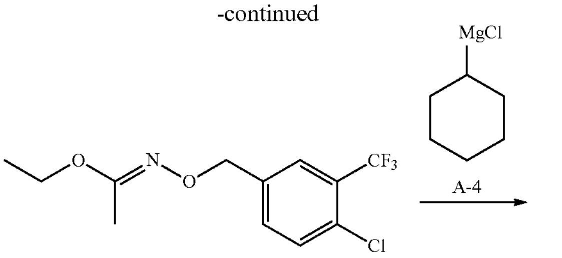

A-3

Intermediate A

Step 1: Synthesis of Compound A-3

Compound A-2 (0.94 g, 9.14 mmol) was dissolved in N,N-dimethylformamide (30 mL), and potassium tert-butoxide (1.03 g, 9.14 mmol) was added. The reaction solution was stirred at 20° C. for 0.5 hours. Intermediate A-1 (2.50 g, 9.14 mmol) dissolved in N,N-dimethylformamide (30 mL) was added to the reaction solution, and the reaction solution was stirred at 20° C. for 12 hours. Water (100 mL) was added to the reaction solution. The mixture was extracted with ethyl acetate (100 mL×3), washed with saturated brine (200 mL×1), dried over anhydrous sodium sulfate, and filtered. The filtrate was concentrated under reduced pressure, and the residue was purified by column chromatography on silica gel (20/1, petroleum ether/ethyl acetate) to give compound A-3.

MS-ESI calculated $[M+H]^+$ 296, found 296.

Step 2: Synthesis of Intermediate A

Zinc chloride (5.81 g, 42.61 mmol) was dissolved in N-methylpyrrolidone (50 mL) at 100° C. under nitrogen atmosphere. The reaction solution was cooled to 25° C., and compound A-4 (4.09 g, 28.41 mmol) was added. The reaction solution was stirred at 25° C. for 10 minutes. The mixture was concentrated under reduced pressure, and compound A-3 (2.10 g, 7.10 mmol) and bis(tri-tert-butylphosphine)palladium (0.36 g, 0.71 mmol) were added. The reaction solution was stirred at 140° C. for 1.3 hours. Water (50 mL) was added to the reaction solution. The mixture was extracted with ethyl acetate (50 mL×3), washed with saturated brine (50 mL×2), dried over anhydrous sodium sulfate, and filtered. The filtrate was concentrated under reduced pressure, and the residue was purified by column chromatography on silica gel (5/1, petroleum ether/ethyl acetate) to give intermediate A.

MS-ESI calculated $[M+H]^+$ 344, found 344.

Intermediate B

B

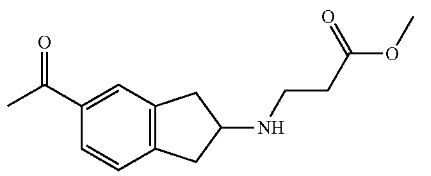

Synthetic Route:

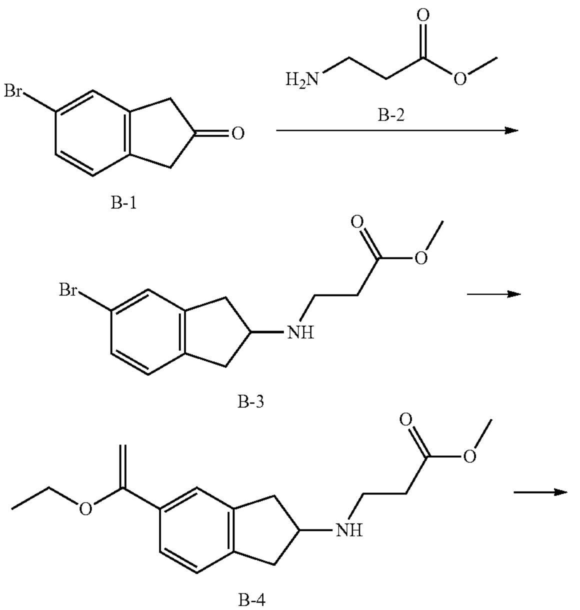

B-1

B-3

B-4

Intermediate B

Step 1: Synthesis of Compound B-3

Compound B-2 hydrochloride (0.40 g, 2.84 mmol) was dissolved in methanol (7.5 mL), and triethylamine (0.29 g, 2.84 mmol) was added. The reaction solution was stirred at 25° C. for 15 minutes. The mixture was cooled in an ice bath to 0° C. Compound B-1 (0.4 g, 1.90 mmol), 2-methylpyridine-N-borane (0.30 g, 2.84 mmol), and acetic acid (1.5 mL) were added to the reaction solution, and the reaction solution was stirred at 25° C. for 1 hour.

Saturated sodium bicarbonate solution (50 mL) was added to the reaction solution. The mixture was extracted with ethyl acetate (25 mL×3), washed with saturated brine (30 mL×1), dried over anhydrous sodium sulfate, and filtered. The filtrate was concentrated under reduced pressure, and the residue was purified by column chromatography on silica gel (1/1, petroleum ether/ethyl acetate) to give compound B-3.

MS-ESI calculated $[M+H]^+$ 298, found 298.

Step 2: Synthesis of Compound B-4

Compound B-3 (0.30 g, 1.01 mmol) was dissolved in toluene (10 mL), and tributyl(1-ethoxyvinyl)stannane (0.73 g, 2.01 mmol) and bis(triphenylphosphine)palladium dichloride (0.07 g, 0.1 mmol) were added. The reaction solution was stirred at 110° C. for 6 h under nitrogen. Saturated potassium fluoride solution (50 mL) was added to the reaction solution. The mixture was extracted with ethyl acetate (25 mL×3), washed with saturated brine (25 mL×1), dried over anhydrous sodium sulfate, and filtered. The filtrate was concentrated under reduced pressure, and the residue was directly used for the next step without purification to give compound B-4.

Step 3: Synthesis of Intermediate B

Compound B-4 (0.20 g, 0.69 mmol) was dissolved in acetone (11 mL), and concentrated hydrochloric acid (0.44 g, 12 mmol) was added. The reaction solution was stirred at 25° C. for 2 hours. Saturated sodium bicarbonate solution (25 mL) was added to the reaction solution. The mixture was extracted with ethyl acetate (30 mL×3), washed with saturated brine (25 mL×1), dried over anhydrous sodium sulfate, and filtered. The filtrate was concentrated under reduced pressure, and the residue was purified by column chromatography on silica gel (0/1, petroleum ether/ethyl acetate) to give intermediate B.

MS-ESI calculated $[M+H]^+$ 262, found 262.

Intermediate C

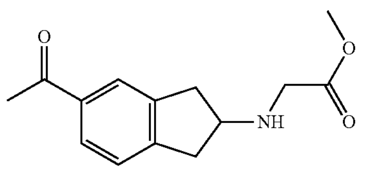

C

Synthetic Route:

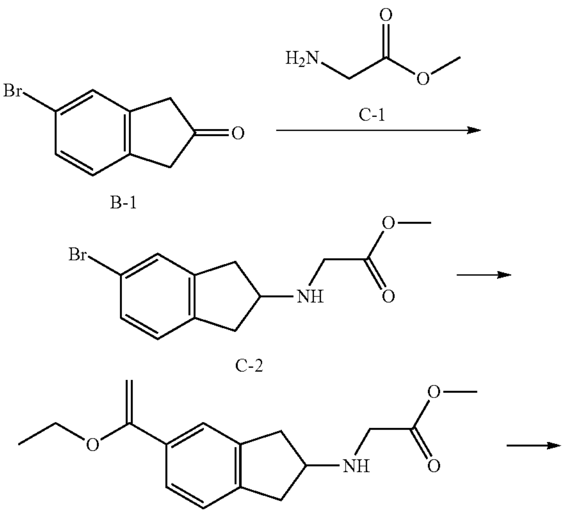

B-1

C-2

C-3

Intermediate C

Step 1: Synthesis of Compound C-2

Compound C-1 hydrochloride (0.31 g, 2.49 mmol) was dissolved in methanol (7.5 mL), and triethylamine (0.25 g, 2.49 mmol) was added. The reaction solution was stirred at 25° C. for 15 minutes. The mixture was cooled in an ice bath to 0° C. Compound B-1 (0.35 g, 1.66 mmol), 2-methylpyridine-N-borane (0.27 g, 2.49 mmol), and acetic acid (1.5 mL) were added to the reaction solution, and the reaction solution was stirred at 25° C. for 1 hour. Saturated sodium bicarbonate solution (50 mL) was added to the reaction solution. The mixture was extracted with ethyl acetate (25 mL×3), washed with saturated brine (30 mL×1), dried over anhydrous sodium sulfate, and filtered. The filtrate was concentrated under reduced pressure, and the residue was purified by column chromatography on silica gel (1/1, petroleum ether/ethyl acetate) to give compound C-2.

$^1H$ NMR (400 MHz, $CD_3OD$) δ=7.33 (s, 1H), 7.25 (d, J=8.0 Hz, 1H), 7.09 (d, J=8.0 Hz, 1H), 3.73 (s, 3H), 3.66-3.58 (m, 1H), 3.45 (s, 2H), 3.17-3.06 (m, 2H), 2.80-2.68 (m, 2H).

Step 2: Synthesis of Compound C-3

Compound C-2 (0.08 g, 0.26 mmol) was dissolved in toluene (10 mL), and tributyl(1-ethoxyvinyl)stannane (0.19 g, 0.53 mmol) and bis(triphenylphosphine)palladium dichloride (0.02 g, 0.03 mmol) were added. The reaction solution was stirred at 110° C. for 6 h under nitrogen. Saturated potassium fluoride solution (50 mL) was added to the reaction solution. The mixture was extracted with ethyl acetate (25 mL×3), washed with saturated brine (25 mL×1), dried over anhydrous sodium sulfate, and filtered. The filtrate was concentrated under reduced pressure, and the residue was directly used for the next step without purification to give the crude product of compound C-3.

Step 3: Synthesis of Intermediate C

The crude product of compound C-3 (0.10 g, 0.36 mmol) was dissolved in acetone (11 mL), and concentrated hydrochloric acid (0.44 g, 12 mmol) was added. The reaction solution was stirred at 25° C. for 2 hours. Saturated sodium bicarbonate solution (25 mL) was added to the reaction solution. The mixture was extracted with ethyl acetate (30 mL×3), washed with saturated brine (25 mL×1), dried over anhydrous sodium sulfate, and filtered. The filtrate was concentrated under reduced pressure, and the residue was purified by column chromatography on silica gel (1/1, petroleum ether/ethyl acetate) to give intermediate C.

MS-ESI calculated $[M+H]^+$ 248, found 248.

Intermediate D

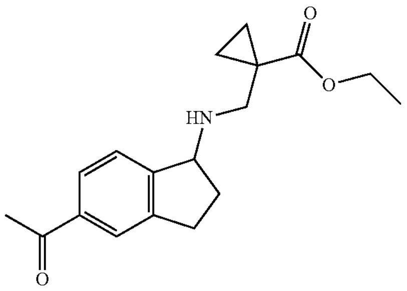

D

Synthetic Route:

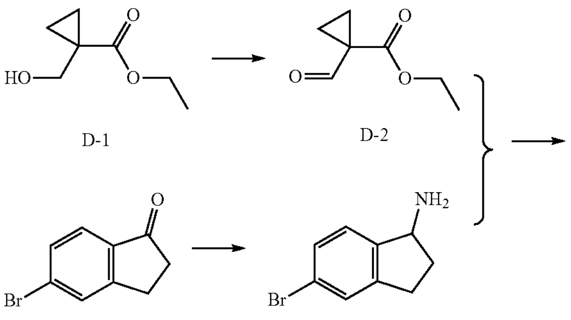

D-1

D-2

D-3

D-4

-continued

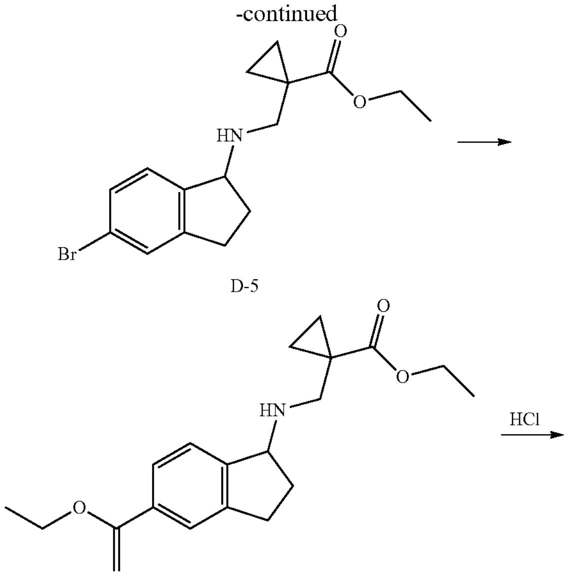

D-5

D-6

Intermediate D

Step 1: Synthesis of Compound D-2

Compound D-1 (0.50 g, 3.47 mmol) was dissolved in dichloromethane (10 mL), and Dess-Martin oxidant (3.24 g, 7.63 mmol) was added. The reaction solution was stirred at 25° C. for 12 hours. Saturated sodium bicarbonate (20 mL) and water (10 mL) were added to the reaction solution at 0° C. The mixture was extracted with dichloromethane (30 mL×3), washed with saturated brine (30 mL×1), dried over anhydrous sodium sulfate, and filtered. The filtrate was concentrated under reduced pressure, and the residue was purified by column chromatography on silica gel (5/1, petroleum ether/ethyl acetate) to give compound D-2.

Step 2: Synthesis of Compound D-4

Compound D-3 (3.00 g, 14.21 mmol) was dissolved in isopropanol (200 mL), and sodium cyanoborohydride (4.47 g, 71.07 mmol) and ammonium acetate (21.91 g, 284.29 mmol) were added. The reaction solution was stirred at 25° C. for 1 hour, then heated to 80° C. and stirred for 11 hours. Water (300 mL) was added to the reaction solution at 25° C. The mixture was extracted with ethyl acetate (100 mL×4), washed with water (150 mL×1), dried over anhydrous sodium sulfate, and filtered. The filtrate was concentrated under reduced pressure, and the residue was purified by column chromatography on silica gel (1/1, petroleum ether/ethyl acetate) to give compound D-4.

MS-ESI calculated $[M-NH_2+H]^+$ 197, found 197.

Step 3: Synthesis of Compound D-5

Compound D-2 (0.17 g, 1.20 mmol) and compound D-4 (0.10 g, 0.47 mmol) were dissolved in dichloromethane (10 mL), and sodium borohydride acetate (0.17 g, 0.80 mmol) and acetic acid (0.05 g, 0.80 mmol) were added. The reaction solution was stirred at 25° C. for 12 hours. The mixture was concentrated under reduced pressure, and saturated sodium bicarbonate was added to the reaction solution. The mixture was extracted with ethyl acetate (30 mL×3), washed with saturated brine (30 mL×1), dried over anhydrous sodium sulfate, and filtered. The filtrate was concentrated under reduced pressure, and the residue was purified by column chromatography on silica gel (1/1, petroleum ether/ethyl acetate) to give compound D-5.

MS-ESI calculated $[M+H]^+$ 338, found 338.

Step 4: Synthesis of Compound D-6

Compound D-5 (0.09 g, 0.27 mmol) was dissolved in toluene (10 mL), and tributyl(1-ethoxyvinyl)stannane (0.19 g, 0.53 mmol) and bis(triphenylphosphine)palladium dichloride (0.02 g, 0.03 mmol) were added. The reaction solution was stirred at 110° C. for 6 h under nitrogen. Saturated potassium fluoride solution (60 mL) was added to the reaction solution. The mixture was extracted with ethyl acetate (30 mL×3), washed with saturated brine (30 mL×1), dried over anhydrous sodium sulfate, and filtered. The filtrate was concentrated under reduced pressure, and the residue was directly used for the next step without purification to give the crude product of compound D-6.

Step 5: Synthesis of Intermediate D

The crude product of compound D-6 (0.12 g, 0.36 mmol) was dissolved in acetone (11 mL), and concentrated hydrochloric acid (0.44 g, 12 mmol) was added. The reaction solution was stirred at 25° C. for 2 hours. Saturated sodium bicarbonate solution (30 mL) was added to the reaction solution. The mixture was extracted with ethyl acetate (40 mL×3), washed with saturated brine (50 mL×1), dried over anhydrous sodium sulfate, and filtered. The filtrate was concentrated under reduced pressure, and the residue was purified by column chromatography on silica gel (1/1, petroleum ether/ethyl acetate) to give intermediate D.

MS-ESI calculated $[M+H]^+$ 302, found 302.

Intermediate E

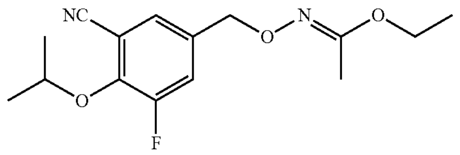

E

Synthetic Route:

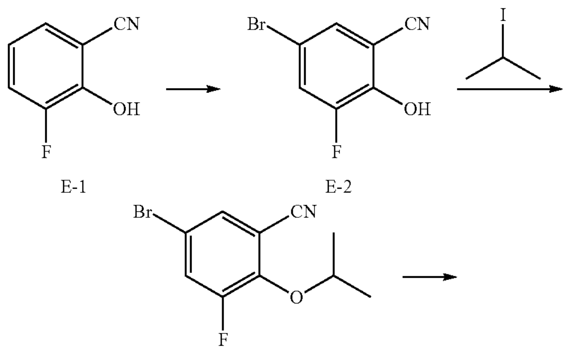

E-1

E-2

E-3

-continued

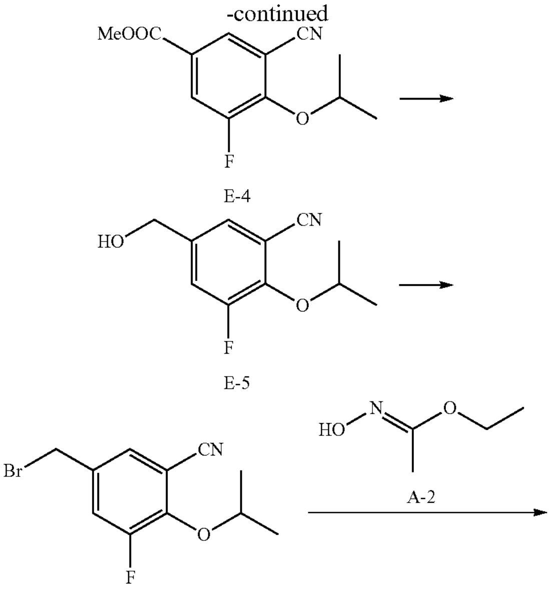

E-4

E-5

A-2

E-6

Intermediate E

Step 1: Synthesis of Compound E-2

Compound E-1 (1.33 g, 9.70 mmol) was dissolved in acetonitrile (40 mL), and NBS (1.73 g, 9.70 mmol) was added. The reaction solution was reacted at 25° C. for 1 hour. The mixture was filtered and the filtrate was concentrated under reduced pressure. The residue was purified by column chromatography on silica gel (3/1, petroleum ether/ethyl acetate) to give compound E-2.

$^1H$ NMR (400 MHz, $CDCl_3$) δ=7.60-7.45 (m, 2H).

Step 2: Synthesis of Compound E-3

Compound E-2 (1.00 g, 4.63 mmol), potassium carbonate (1.92 g, 13.89 mmol) and iodoisopropane (1.57 g, 9.26 mmol) were added into N,N-dimethylformamide (10 mL). The mixture was reacted at 70° C. for 2 hours. The mixture was cooled to 20° C., and filtered. The filtrate was concentrated under reduced pressure. The residue was purified by column chromatography on silica gel (10/1, petroleum ether/ethyl acetate) to give compound E-3.

$^1H$ NMR (400 MHz, $CDCl_3$) δ=7.58-7.41 (m, 2H), 4.82-4.61 (m, 1H), 1.42 (d, J=8.0 Hz, 6H).

Step 3: Synthesis of Compound E-4

Compound E-3 (1.00 g, 3.87 mmol), triethylamine (10 mL) and $Pd(dppf)Cl_2$ (0.57 g, 0.78 mmol) were added to methanol (30 mL) and N,N-dimethylformamide (10 mL) under argon. The reaction mixture was stirred at 80° C. under carbon monoxide (50 psi) for 48 hours. The mixture was cooled to 20° C., and filtered. The filtrate was concentrated under reduced pressure. The residue was purified by column chromatography on silica gel (5/1, petroleum ether/ethyl acetate) to give compound E-4.

Step 4: Synthesis of Compound E-5

The raw material E-4 (0.65 g, 2.74 mmol) was dissolved in tetrahydrofuran (20 mL) under nitrogen atmosphere, and the solution was cooled to 0° C. Lithium borohydride (0.48 g, 21.92 mmol) was added to the reaction solution, and the mixture was reacted at 45° C. for 1 hour. Water (0.7 mL) was added. The mixture was filtered, and the filtrate was concentrated under reduced pressure. The residue was purified by column chromatography on silica gel (3/1, petroleum ether/ethyl acetate) to give compound E-5.

Step 5: Synthesis of Compound E-6

To a solution of compound E-5 (0.52 g, 2.49 mmol) in tetrahydrofuran (10 mL) were added carbon tetrabromide (0.99 g, 2.98 mmol) and triphenylphosphine (0.69 g, 2.61 mmol) under nitrogen atmosphere. The mixture was stirred at 25° C. for 15 hours. The mixture was filtered and the filtrate was concentrated under reduced pressure. The residue was purified by column chromatography on silica gel (5/1, petroleum ether/ethyl acetate) to give compound E-6.

$^1$H NMR (400 MHz, $CDCl_3$) δ=7.41-7.35 (m, 2H), 4.80-4.69 (m, 1H), 4.42 (s, 2H), 1.42 (d, J=4.0 Hz, 6H).

Step 6: Synthesis of Intermediate E

To a solution of the raw material A-2 (0.18 g, 1.76 mmol) in N,N-dimethylformamide (10 mL) was added potassium tert-butoxide (0.20 g, 1.76 mmol) under nitrogen atmosphere. The reaction solution was stirred at 20° C. for 0.5 hours. A solution of intermediate E-6 in N,N-dimethylformamide (2 mL) was added dropwise to the reaction solution, and the reaction solution was stirred at 20° C. for 2 hours. Water (50 mL) was added to the reaction solution. The mixture was extracted with ethyl acetate (30 mL×3), washed with saturated brine (30 mL×1), dried over anhydrous sodium sulfate, and filtered. The filtrate was concentrated under reduced pressure, and the residue was purified by column chromatography on silica gel (10/1, petroleum ether/ethyl acetate) to give compound E.

MS-ESI calculated $[M+H]^+$ 295, found 295.

Intermediate F

F

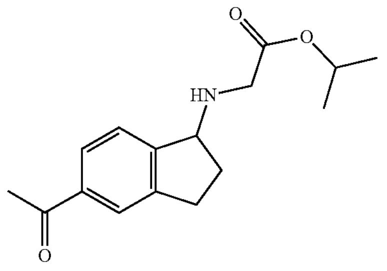

Synthetic Route:

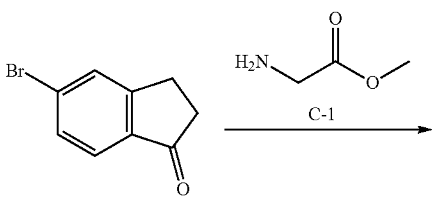

F-1

-continued

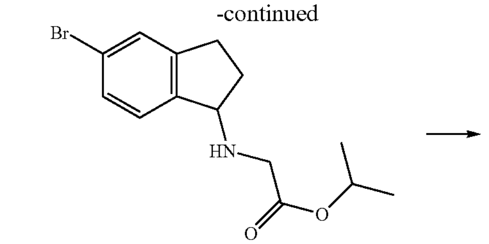

F-2

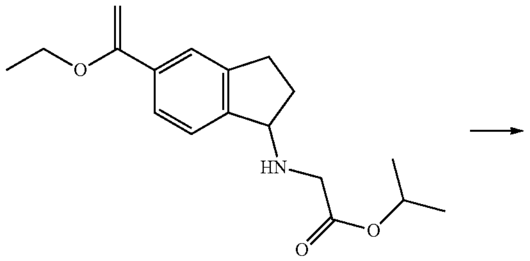

F-3

Intermediate F

Step 1: Synthesis of Compound F-2

Compound C-1 hydrochloride (7.73 g, 61.60 mmol) and triethylamine (7.19 g, 71.07 mmol) were dissolved in tetrahydrofuran (100 mL), and tetraisopropyl titanate (26.93 g, 94.76 mmol) and compound F-1 (10.00 g, 47.38 mmol) were added. The reaction solution was stirred at 65° C. for 12 hours. Methanol (100 mL) and sodium borohydride (3.59 g, 94.76 mmol) were added, and the reaction solution was stirred at 15° C. for 3 hours. Water (100 mL) was added to the reaction solution. The mixture was extracted with ethyl acetate (200 mL×4), washed with saturated brine (100 mL×1), dried over anhydrous sodium sulfate, and filtered. The filtrate was concentrated under reduced pressure, and the residue was purified by column chromatography on silica gel (1/1, petroleum ether/ethyl acetate) to give compound F-2.

MS-ESI calculated $[M+H]^+$ 314, found 314.

Step 2: Synthesis of Compound F-3

Compound F-2 (7.00 g, 22.42 mmol) was dissolved in toluene (100 mL), and tributyl(1-ethoxyvinyl)stannane (16.19 g, 44.84 mmol) and bis(triphenylphosphine)palladium dichloride (1.57 g, 2.24 mmol) were added. The reaction solution was stirred at 110° C. for 12 hours under nitrogen atmosphere. Saturated potassium fluoride solution (200 mL) was added to the reaction solution. The mixture was extracted with ethyl acetate (200 mL×3), washed with saturated brine (100 mL×1), dried over anhydrous sodium sulfate, and filtered. The filtrate was concentrated under reduced pressure, and the residue was directly used for the next step without purification to give compound F-3.

Step 3: Synthesis of Intermediate F

Compound F-3 (5.00 g, 16.48 mmol) was dissolved in acetone (100 mL), and concentrated hydrochloric acid (20 mL, 14.56 mmol) was added. The reaction solution was stirred at 25° C. for 2 hours. Saturated sodium bicarbonate solution (150 mL) was added to the reaction solution. The mixture was extracted with ethyl acetate (100 mL×4), washed with saturated brine (100 mL×1), dried over anhydrous sodium sulfate, and filtered. The filtrate was concentrated under reduced pressure, and the residue was purified by column chromatography on silica gel (1/1, petroleum ether/ethyl acetate) to give intermediate F.

MS-ESI calculated $[M+H]^+$ 276, found 276.

Intermediate G

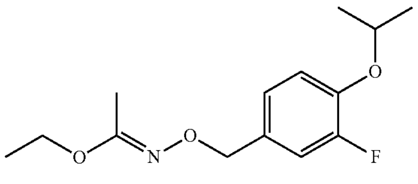

G

Synthetic Route:

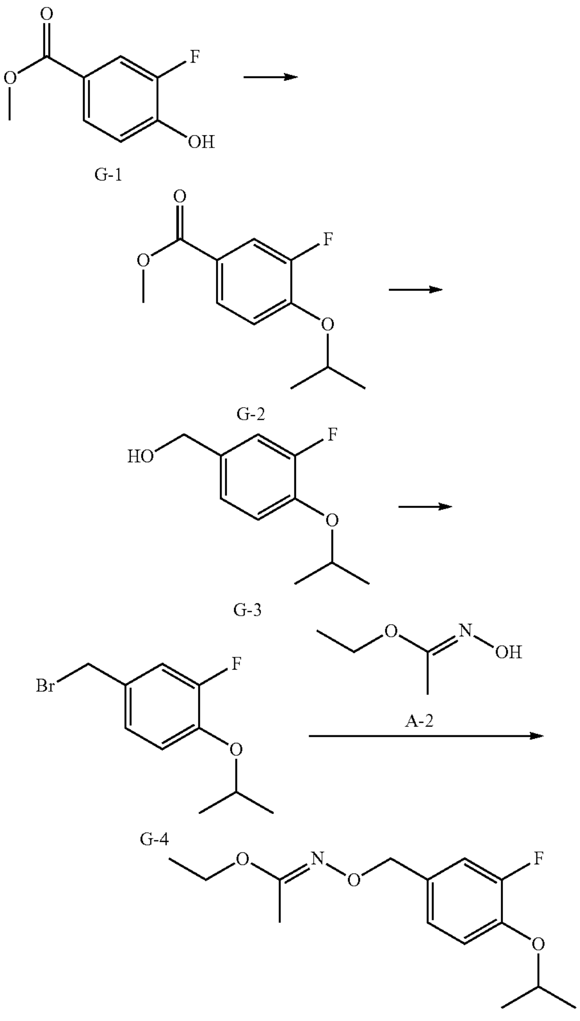

G-1

G-2

G-3

G-4

G

Step 1: Synthesis of Compound G-2

Compound G-1 (4.00 g, 23.51 mmol), iodoisopropane (3.40 g, 19.98 mmol), and potassium carbonate (6.50 g, 47.02 mmol) were dissolved in N,N-dimethylformamide (5 mL). The mixture was stirred at 25° C. for 15 hours. Water (30 mL) was added to the reaction solution. The mixture was extracted with ethyl acetate (30 mL×2), washed successively with water (30 mL×2) and saturated brine (30 mL×2), dried over anhydrous sodium sulfate, and filtered. The filtrate was concentrated under reduced pressure. The residue was purified by column chromatography on silica gel (3/1, petroleum ether/ethyl acetate) to give compound G-2.

MS-ESI calculated $[M+H]^+$ 213, found 213.

$^1$H NMR (400 MHz, DMSO-$d_6$) δ=7.81-7.58 (m, 2H), 7.28 (t, J=8.4 Hz, 1H), 4.84-4.72 (m, 1H), 3.82 (s, 3H), 1.31 (d, J=8.0 Hz, 6H).

Step 2: Synthesis of Compound G-3

Compound G-2 (4.28 g, 20.17 mmol) was dissolved in tetrahydrofuran (50 mL), and lithium borohydride (3.51 g, 161.34 mmol) was added at 0° C. The reaction mixture was stirred at 25° C. for 12 hours. The reaction solution was slowly added dropwise to 100 mL of saturated ammonium chloride solution. The mixture was extracted with ethyl acetate (50 mL×2), washed successively with water (50 mL×2) and saturated brine (50 mL×2), dried over anhydrous sodium sulfate, and filtered. The filtrate was concentrated under reduced pressure. The residue was purified by column chromatography on silica gel (3/1, petroleum ether/ethyl acetate) to give compound G-3.

$^1$H NMR (400 MHz, DMSO-$d_6$) δ=7.14-7.02 (m, 3H), 5.17 (t, J=5.8 Hz, 1H), 4.61-4.51 (m, 1H), 4.41 (d, J=5.8 Hz, 2H), 1.26 (d, J=8.0 Hz, 6H).

Step 3: Synthesis of Compound G-4

Compound G-3 (3.50 g, 19.00 mmol) was dissolved in tetrahydrofuran (50 mL) at 0° C., and carbon tetrabromide (7.56 g, 22.80 mmol) and triphenylphosphine (5.23 g, 19.95 mmol) were added. The mixture was stirred at 25° C. for 15 hours. The mixture was concentrated under reduced pressure, and the residue was purified by column chromatography on silica gel (3/1, petroleum ether/ethyl acetate) to give compound G-4.

$^1$H NMR (400 MHz, DMSO-$d_6$) δ=7.32-7.26 (m, 1H), 7.23-7.17 (m, 1H), 7.17-7.10 (m, 1H), 4.72-4.60 (m, 3H), 1.27 (d, J=8.0 Hz, 6H).

Step 4: Synthesis of Intermediate G

Compound A-2 (1.44 g, 13.99 mmol) was dissolved in N,N-dimethylformamide (5 mL) at 25° C., and potassium tert-butoxide (1.57 g, 13.99 mmol) was added. The mixture was stirred for 40 minutes, and compound G-4 (2.88 g, 11.66 mmol) was added. The reaction solution was stirred for 5 hours. Water (20 mL) was added. The mixture was extracted with ethyl acetate (20 mL×2), washed successively with water (20 mL×2) and saturated brine (20 mL×2), dried over anhydrous sodium sulfate, and filtered. The filtrate was concentrated under reduced pressure. The residue was purified by column chromatography on silica gel (3/1, petroleum ether/ethyl acetate) to give intermediate G.

MS-ESI calculated $[M+H]^+$ 270, found 270.

$^1$H NMR (400 MHz, DMSO-$d_6$) δ=7.21-7.04 (m, 3H), 4.79 (s, 2H), 4.67-4.53 (m, 1H), 3.92 (q, J=8.0 Hz, 2H), 1.87 (s, 3H), 1.27 (d, J=8.0 Hz, 6H), 1.18 (t, J=8.0 Hz, 3H).

Intermediate H

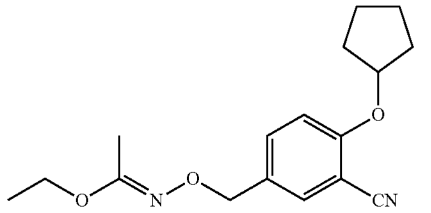

H

Synthetic Route:

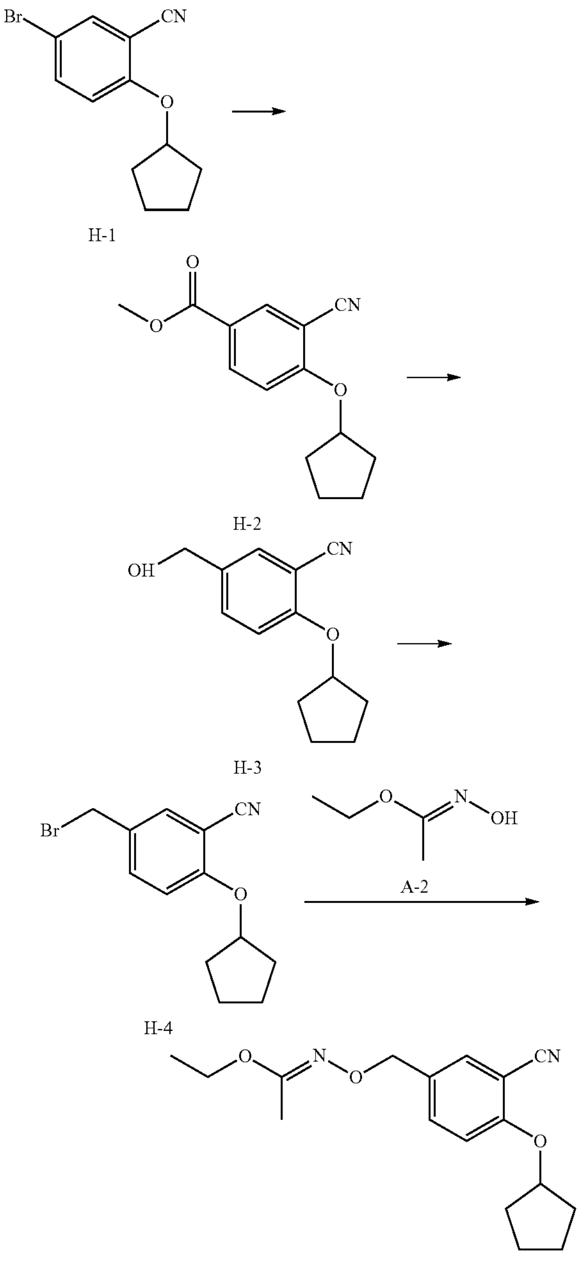

H-1

H-2

H-3

A-2

H-4

H

Step 1: Synthesis of Compound H-2

Compound H-1 (5.70 g, 21.42 mmol) and 1,1-bis(diphenylphosphino)ferrocene palladium chloride (3.13 g, 4.28 mmol) were dissolved in methanol (340 mL), triethylamine (114 mL) and N,N-dimethylformamide (114 mL). The atmosphere in the reaction system was replaced three times with carbon monoxide, and then the reaction solution was heated to 80° C. The reaction was stirred under carbon monoxide atmosphere (50 Psi) for 48 hours. The reaction solution was concentrated under reduced pressure, extracted with ethyl acetate (150 mL×2), washed successively with water (100 mL×2) and saturated brine (100 mL×2), dried over anhydrous sodium sulfate, and filtered. The filtrate was concentrated under reduced pressure. The residue was purified by column chromatography on silica gel (3/1, petroleum ether/ethyl acetate) to give compound H-2.

$^1$H NMR (400 MHz, $CD_3OD$) δ=8.26-8.15 (m, 2H), 7.31-7.20 (m, 1H), 5.11-5.03 (m, 1H), 3.93-3.86 (m, 3H), 2.07-1.69 (m, 8H).

Step 2: Synthesis of Compound H-3

Compound H-2 (1.70 g, 6.93 mmol) was dissolved in tetrahydrofuran (45 mL) at 25° C., and lithium borohydride (1.21 g, 55.45 mmol) was added at 0° C. The reaction solution was stirred at 25° C. for 12 hours. The reaction solution was slowly added dropwise to saturated ammonium chloride solution (200 mL). The mixture was extracted with ethyl acetate (50 mL×2), washed successively with water (20 mL×2) and saturated brine (20 mL×2), dried over anhydrous sodium sulfate, and filtered. The filtrate was concentrated under reduced pressure. The residue was purified by column chromatography on silica gel (3/1, petroleum ether/ethyl acetate) to give compound H-3.

$^1$H NMR (400 MHz, DMSO-$d_6$) δ=7.63-7.50 (m, 2H), 7.19 (d, J=8.6 Hz, 1H), 5.26 (t, J=5.8 Hz, 1H), 4.97 (t, J=5.6 Hz, 1H), 4.43 (d, J=5.8 Hz, 2H), 1.97-1.53 (m, 8H).

Step 3: Synthesis of Compound H-4

Compound H-3 (1.26 g, 5.80 mmol) was dissolved in tetrahydrofuran (20 mL) at 0° C., and carbon tetrabromide (2.31 g, 6.96 mmol) and triphenylphosphine (1.60 g, 6.09 mmol) were added. The reaction solution was stirred to react at 25° C. for 15 hours. The reaction solution was concentrated under reduced pressure, and the residue was purified by column chromatography on silica gel (3/1, petroleum ether/ethyl acetate) to give compound H-4.

$^1$H NMR (400 MHz, DMSO-$d_6$) δ=7.81 (d, J=2.0 Hz, 1H), 7.72 (dd, J=2.4, 8.8 Hz, 1H), 7.25 (d, J=8.8 Hz, 1H), 5.06-4.96 (m, 1H), 4.70 (s, 2H), 1.99-1.61 (m, 8H).

Step 4: Synthesis of Compound H

Compound A-2 (477.02 mg, 4.63 mmol) was dissolved in N,N-dimethylformamide (3 mL), and then potassium tert-butoxide (519.09 mg, 4.63 mmol) was added. The mixture was stirred for 40 minutes and then compound H-4 (1.08 g, 3.85 mmol) was added. The mixture was stirred at 25° C. for 5 hours. Water (10 mL) was added to the reaction solution. The mixture was extracted with ethyl acetate (10 mL×1), washed successively with water (20 mL×2) and saturated brine (20 mL×2), dried over anhydrous sodium sulfate, and filtered. The filtrate was concentrated under reduced pressure. The residue was purified by column chromatography on silica gel (3/1, petroleum ether/ethyl acetate) to give intermediate H.

MS-ESI calculated $[M+H]^+$ 303, found 303.

$^1$H NMR (400 MHz, DMSO-$d_6$) δ=7.67-7.57 (m, 2H), 7.21 (d, J=8.8 Hz, 1H), 4.98 (m, 1H), 4.82 (s, 2H), 3.91 (m, 2H), 2.00-1.89 (m, 2H), 1.87 (s, 3H), 1.78-1.55 (m, 6H), 1.17 (t, J=6.8 Hz, 3H).

Intermediate I

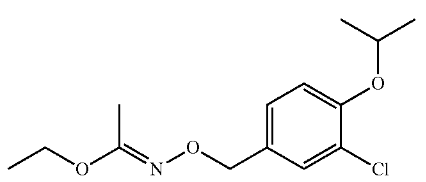

I

Synthetic Route:

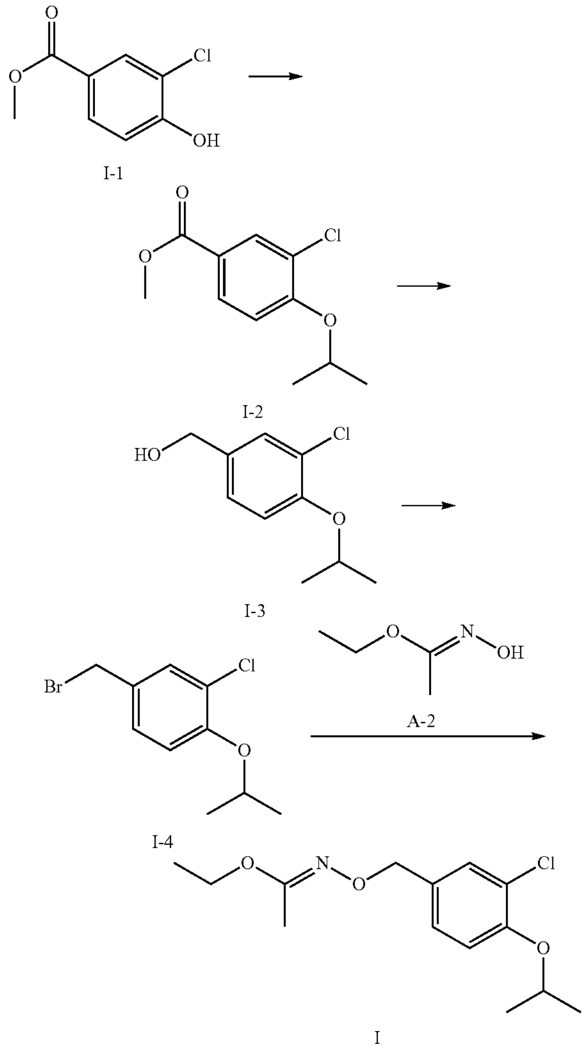

I-1

I-2

I-3

A-2

I-4

I

Step 1: Synthesis of Compound I-2

Compound I-1 (1.00 g, 5.36 mmol), iodoisopropane (774.38 mg, 4.56 mmol) and potassium carbonate (1.48 g, 10.72 mmol) were dissolved in N,N-dimethylformamide (2 mL). The mixture was stirred at 25° C. for 18 hours. Water (30 mL) was added to the reaction solution. The mixture was extracted with ethyl acetate (30 mL×2), washed successively with water (30 mL×2) and saturated brine (30 mL×2), dried over anhydrous sodium sulfate, and filtered. The filtrate was concentrated under reduced pressure. The residue was purified by column chromatography on silica gel (3/1, petroleum ether/ethyl acetate) to give compound I-2.

MS-ESI calculated $[M+H]^+$ 229, found 229.

$^1$H NMR (400 MHz, DMSO-$d_6$) δ=7.94-7.80 (m, 2H), 7.27 (d, J=8.8 Hz, 1H), 4.80 (s, J=6.0 Hz, 1H), 3.82 (s, 3H), 1.32 (d, J=8.0 Hz, 6H).

Step 2: Synthesis of Compound I-3

Compound I-2 (0.90 g, 3.94 mmol) was dissolved in tetrahydrofuran (10 mL) at 25° C., and lithium borohydride (0.69 g, 31.49 mmol) was added at 0° C. The reaction solution was stirred at 25° C. for 12 hours. The reaction solution was slowly added dropwise to 100 mL of saturated ammonium chloride solution. The mixture was extracted with ethyl acetate (50 mL×2), washed successively with water (50 mL×2) and saturated brine (50 mL×2), dried over anhydrous sodium sulfate, and filtered. The filtrate was concentrated under reduced pressure. The residue was purified by column chromatography on silica gel (3/1, petroleum ether/ethyl acetate) to give compound I-3.

$^1$H NMR (400 MHz, DMSO-$d_6$) δ=7.34 (d, J=2.0 Hz, 1H), 7.22-7.16 (m, 1H), 7.09 (d, J=8.6 Hz, 1H), 5.19 (t, J=5.8 Hz, 1H), 4.66-4.55 (m, 1H), 4.41 (d, J=5.8 Hz, 2H), 1.27 (d, J=8.0 Hz, 6H).

Step 3: Synthesis of Compound I-4

Compound I-3 (0.61 g, 3.04 mmol) was dissolved in tetrahydrofuran (10 mL) at 0° C., and carbon tetrabromide (1.21 g, 3.65 mmol) and triphenylphosphine (837.20 mg, 3.19 mmol) were added. The reaction solution was stirred at 25° C. for 15 hours. The mixture was concentrated under reduced pressure. The residue was purified by column chromatography on silica gel (3/1, petroleum ether/ethyl acetate) to give compound I-4.

$^1$H NMR (400 MHz, DMSO-$d_6$) δ=7.51 (d, J=2.4 Hz, 1H), 7.35 (dd, J=2.0, 8.6 Hz, 1H), 7.12 (d, J=8.6 Hz, 1H), 4.73-4.60 (m, 3H), 1.28 (d, J=8.0 Hz, 6H).

Step 4: Synthesis of Intermediate I

Compound A-2 (0.31 g, 3.01 mmol) was dissolved in N,N-dimethylformamide (5 mL), and potassium tert-butoxide (0.34 g, 3.01 mmol) was added. The mixture was stirred for 40 minutes, and then compound I-4 (0.66 g, 2.50 mmol) was added. The mixture was stirred at 25° C. for 5 hours. Water (10 mL) was added to the reaction solution. The mixture was extracted with ethyl acetate (10 mL×2), washed successively with water (10 mL×2) and saturated brine (10 mL×2), dried over anhydrous sodium sulfate, and filtered. The filtrate was concentrated under reduced pressure. The residue was purified by column chromatography on silica gel (3/1, petroleum ether/ethyl acetate) to give intermediate I.

$^1$H NMR (400 MHz, DMSO-$d_6$) δ=7.38 (d, J=2.0 Hz, 1H), 7.25 (dd, J=2.0, 8.4 Hz, 1H), 7.12 (d, J=8.6 Hz, 1H), 4.79 (s, 2H), 4.69-4.60 (m, 1H), 3.97-3.88 (m, 2H), 1.89-1.82 (m, 3H), 1.28 (d, J=6.0 Hz, 6H), 1.22-1.14 (m, 3H).

MS-ESI calculated $[M+H]^+$ 286, found 286.

Intermediate J

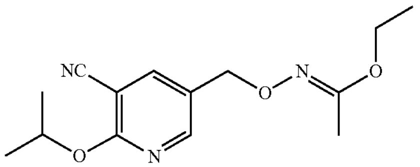

J

Synthetic Route:

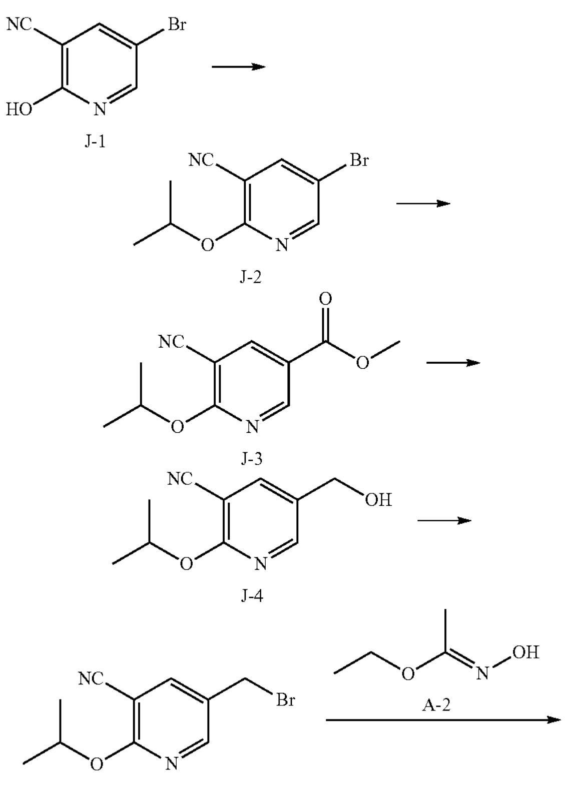

J-1

J-2

J-3

J-4

A-2

J-5

Intermediate J

Step 1: Synthesis of Compound J-2

Compound J-1 (5.00 g, 25.12 mmol), silver carbonate (20.78 g, 75.37 mmol) and iodoisopropane (8.54 g, 50.25 mmol,) were added to toluene (50 mL). The reaction solution was stirred at 50° C. for 1 hour. The mixture was cooled to 20° C., and filtered. The filtrate was concentrated under reduced pressure. The residue was purified by column chromatography on silica gel (10/1, petroleum ether/ethyl acetate) to give compound J-2.

$^1$H NMR (400 MHz, $CDCl_3$) δ=8.28 (d, J=2.4 Hz, 1H), 7.86 (d, J=2.4 Hz, 1H), 5.35-5.22 (m, 1H), 1.32 (d, J=6.4 Hz, 6H).

Step 2: Synthesis of Compound J-3

Compound J-2 (5.00 g, 20.74 mmol), triethylamine (100 mL) and Pd(dppf)$Cl_2$ (3.04 g, 4.15 mmol) were added to methanol (300 mL) and N,N-dimethylformamide (100 mL).

The reaction mixture was stirred at 80° C. under carbon monoxide (50 psi) for 48 hours. The reaction solution was cooled to 20° C., and filtered. The filtrate was concentrated under reduced pressure. The residue was purified by column chromatography on silica gel (5/1, petroleum ether/ethyl acetate) to give compound J-3.

$^1$H NMR (400 MHz, $CDCl_3$) δ=8.95 (d, J=2.0 Hz, 1H), 8.45 (d, J=2.5 Hz, 1H), 5.56-5.47 (m, 1H), 3.94 (s, 3H), 1.43 (d, J=8.0 Hz, 6H).

Step 3: Synthesis of Compound J-4

Under nitrogen atmosphere, compound J-3 (1.00 g, 4.54 mmol) was dissolved in tetrahydrofuran (15 mL), and lithium aluminum tetrahydride (1.72 g, 45.41 mmol) was added at −40° C. The mixture was stirred at −40° C. for 2 hours. Water (1 mL) was added. The mixture was filtered, and the filtrate was concentrated under reduced pressure to give the crude product of compound J-4.

$^1$H NMR (400 MHz, $CDCl_3$) δ=8.32 (d, J=2.5 Hz, 1H), 7.91 (d, J=2.5 Hz, 1H), 5.57-5.37 (m, 1H), 4.43 (s, 2H), 3.94 (s, 1H), 1.41 (d, J=6.4 Hz, 6H).

Step 4: Synthesis of Compound J-5

Under nitrogen atmosphere, to the solution of the crude product of compound J-4 (1.00 g, 5.20 mmol) in tetrahydrofuran (10 mL) were added carbon tetrabromide (2.07 g, 6.24 mmol) and triphenylphosphine (1.43 g, 5.46 mmol). The reaction solution was stirred at 25° C. for 15 hours. The mixture was filtered and the filtrate was concentrated under reduced pressure. The residue was purified by column chromatography on silica gel (10/1, petroleum ether/ethyl acetate) to give compound J-5.

$^1$H NMR (400 MHz, $CDCl_3$) δ=8.25 (d, J=2.4 Hz, 1H), 7.83 (d, J=2.4 Hz, 1H), 5.38-5.15 (m, 1H), 4.35 (s, 2H), 1.42-1.40 (m, 6H).

Step 5: Synthesis of Intermediate J

Under nitrogen atmosphere, to a solution of compound A-2 (0.22 g, 2.16 mmol) in N,N-dimethylformamide (10 mL) was added potassium tert-butoxide (0.24 g, 2.16 mmol). The reaction solution was stirred at 20° C. for 0.5 hours. Then, a solution of compound J-5 in N,N-dimethylformamide (5 mL) was added dropwise to the reaction solution, and the reaction solution was reacted at 20° C. for 2 hours. Water (20 mL) was added. The mixture was extracted with ethyl acetate (50 mL×3), washed with saturated brine (50 mL) and water (50 mL), and concentrated under reduced pressure. The residue was purified by column chromatography on silica gel (10/1, petroleum ether/ethyl acetate) to give intermediate J.

MS-ESI calculated $[M+H]^+$ 278, found 278.

Intermediate K

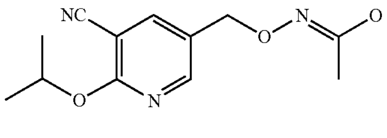

K

Synthetic Route:

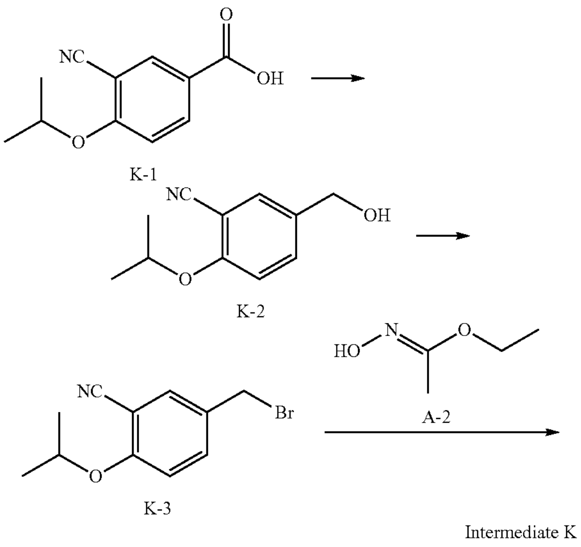

K-1

K-2

K-3

A-2

Intermediate K

Step 1: Synthesis of Compound K-2

Under nitrogen atmosphere, compound K-1 (1.00 g, 4.87 mmol) was dissolved in tetrahydrofuran (10 mL), and boron trifluoride ether solution (0.69 g, 4.87 mmol) and borane tetrahydrofuran solution (9.75 mL, 9.75 mmol) were added successively. The mixture was stirred at 20° C. for 2 hours. Water (50 mL) was added to the reaction solution. The mixture was extracted with ethyl acetate (50 mL×3), washed successively with saturated brine (50 mL) and water (50 mL), and filtered. The filtrate was concentrated under reduced pressure to give the crude product of compound K-2.

Step 2: Synthesis of Compound K-3

Under nitrogen atmosphere, to the solution of the crude product of compound K-2 (1.0 g, 5.23 mmol) in tetrahydrofuran (10 mL) were added carbon tetrabromide (2.08 g, 6.24 mmol) and triphenylphosphine (1.44 g, 5.46 mmol). The reaction solution was reacted at 25° C. for 15 hours. The mixture was filtered and the filtrate was concentrated under reduced pressure. The residue was purified by column chromatography on silica gel (5/1, petroleum ether/ethyl acetate) to give the crude product of compound K-3.

$^1$H NMR (400 MHz, $CDCl_3$) δ=7.58 (d, J=2.0 Hz, 1H), 7.55-7.51 (m, 1H), 6.94 (d, J=9.0 Hz, 1H), 4.71-4.62 (m, 1H), 4.44 (s, 2H), 1.42 (d, J=4.0 Hz, 6H).

Step 3: Synthesis of Intermediate K

Under nitrogen atmosphere, to a solution of compound A-2 (0.89 g, 8.66 mmol) in N,N-dimethylformamide (20 mL) was added potassium tert-butoxide (0.97 g, 8.66 mmol). The reaction solution was reacted at 20° C. for 0.5 hours. Then, a solution of the crude product of compound K-3 (2.00 g, 7.87 mmol) in N,N-dimethylformamide (10 mL) was added dropwise to the reaction solution, and the reaction solution was reacted at 20° C. for 2 hours. Water (50 mL) was added. The mixture was extracted with ethyl acetate (50 mL×3). The combined organic phase was washed with saturated brine (50 mL) and water (50 mL), and filtered. The filtrate was concentrated under reduced pressure, and the residue was purified by column chromatography on silica gel (10/1, petroleum ether/ethyl acetate) to give intermediate K.

$^1$H NMR (400 MHz, $CDCl_3$) δ=7.55 (d, J=2.0 Hz, 1H), 7.48 (dd, J=2.0, 8.0 Hz, 1H), 6.92 (d, J=12.0 Hz, 1H), 4.82 (s, 2H), 4.67-4.61 (m, 1H), 3.97 (q, J=8.0 Hz, 2H), 1.92 (s, 3H), 1.40 (d, J=8.0 Hz, 6H), 1.25 (t, J=8.0 Hz, 3H).

Intermediate L

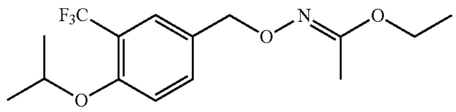

L

Synthetic Route:

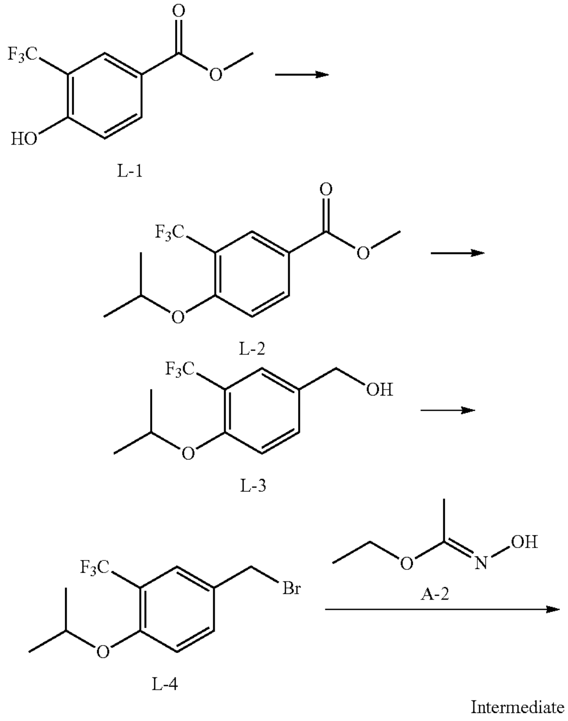

L-1

L-2

L-3

L-4

A-2

Intermediate L

Step 1: Synthesis of Compound L-2

Compound L-1 (4.00 g, 18.17 mmol), potassium carbonate (7.53 g, 54.51 mmol) and iodoisopropane (6.18 g, 36.34 mmol) were added to N,N-dimethylformamide (40 mL). The reaction solution was stirred at 70° C. for 2 hours. The mixture was cooled to 20° C., and filtered. The filtrate was concentrated under reduced pressure. The residue was purified by column chromatography on silica gel (10/1, petroleum ether/ethyl acetate) to give compound L-2.

$^1$H NMR (400 MHz, $CDCl_3$) δ=8.25 (d, J=2.0 Hz, 1H), 8.15 (dd, J=2.0, 8.0 Hz, 1H), 7.01 (d, J=12.0 Hz, 1H), 4.77-4.69 (m, 1H), 3.91 (s, 3H), 1.40 (d, J=8.0 Hz, 6H).

Step 2: Synthesis of Compound L-3

Under nitrogen atmosphere, compound L-2 (1.00 g, 3.81 mmol) was dissolved in tetrahydrofuran (20 mL), and lithium borohydride (0.66 g, 30.51 mmol) was added at 20° C. The mixture was reacted at 50° C. for 14 hours. The mixture was filtered and the filtrate was concentrated under reduced pressure. The residue was purified by column chromatography on silica gel (3/1, petroleum ether/ethyl acetate) to give compound L-3.

$^1$H NMR (400 MHz, $CDCl_3$) δ=7.56 (d, J=1.6 Hz, 1H), 7.46 (dd, J=2.0, 8.0 Hz, 1H), 6.99 (d, J=8.0 Hz, 1H), 4.69-4.61 (m, 3H), 1.34 (br s, 1H), 1.36 (d, J=6.0 Hz, 6H).

Step 3: Synthesis of Compound L-4

Under nitrogen atmosphere, to a solution of the raw material L-3 (0.90 g, 3.46 mmol) in tetrahydrofuran (15 mL) were added carbon tetrabromide (1.53 g, 4.61 mmol) and triphenylphosphine (1.06 g, 4.03 mmol). The reaction solution was reacted at 25° C. for 15 hours. The mixture was filtered and the filtrate was concentrated under reduced pressure. The residue was purified by column chromatography on silica gel (5/1, petroleum ether/ethyl acetate) to give compound L-4.

Step 4: Synthesis of Intermediate L

Under nitrogen atmosphere, to a solution of compound A-2 (0.21 g, 2.02 mmol) in N,N-dimethylformamide (5 mL) was added potassium tert-butoxide (0.23 g, 2.02 mmol). The reaction solution was stirred at 20° C. for 0.5 hours. Then, a solution of compound L-4 (0.50 g, 1.68 mmol, 1 eq) in N,N-dimethylformamide (1 mL) was added dropwise to the reaction solution, and the reaction solution was reacted at 20° C. for 2 hours. Water (50 mL) was added to the reaction solution. The mixture was extracted with ethyl acetate (50 mL×3), washed successively with saturated brine (50 mL) and water (50 mL), and concentrated under reduced pressure. The residue was purified by column chromatography on silica gel (10/1, petroleum ether/ethyl acetate) to give intermediate L.

MS-ESI calculated [M+H]$^+$ 320, found 320.

Intermediate M

M

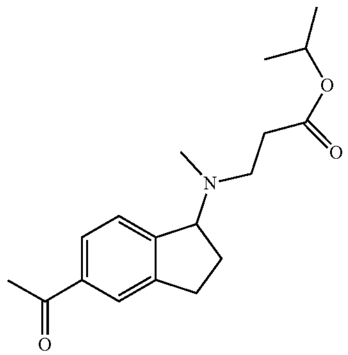

Synthetic Route:

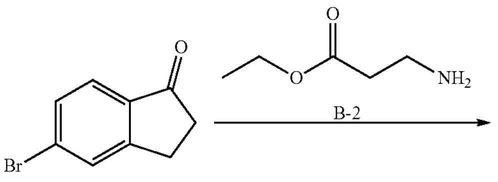

F-1

-continued

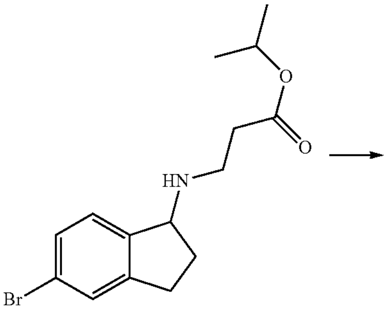

M-1

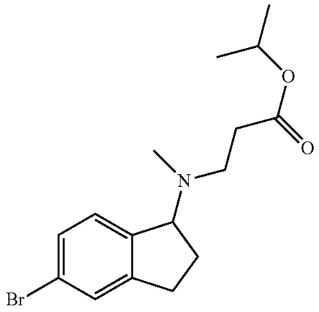

M-2

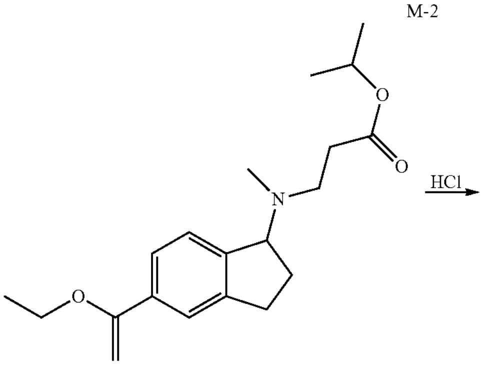

M-3

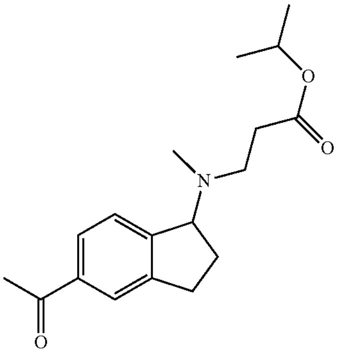

M

Step 1: Synthesis of Compound M-1

Compound F-1 (5.50 g, 26.06 mmol) and compound B-2 hydrochloride (5.20 g, 33.88 mmol) were dissolved in tetrahydrofuran (60 mL). Isopropyl titanate (14.81 g, 52.12 mmol) and triethylamine (3.96 g, 39.09 mmol) were added to the reaction solution. The reaction solution was reacted at 65° C. for 12 hours. After the reaction was completed, the mixture was cooled to 20° C., and methanol (60 mL) and sodium borohydride (1.97 g, 52.12 mmol) were added to the reaction solution. The mixture was reacted at 15° C. for 3 hours. Water (150 mL) was added to the reaction solution. The mixture was extracted with ethyl acetate (250 mL×3), washed with saturated brine (250 mL) and water (250 mL), and concentrated under reduced pressure to give compound M-1.

MS-ESI calculated $[M+H]^+$ 328, found 328.

Step 2: Synthesis of Compound M-2

Under nitrogen atmosphere, to a solution of compound M-1 (0.1 g, 0.31 mmol) in formic acid (10 mL) was added formaldehyde (0.12 g, 1.53 mmol). The reaction solution was reacted at 60° C. for 15 hours. The mixture was concentrated under reduced pressure to give the crude product of compound M-2.

MS-ESI calculated $[M+H]^+$ 342, found 342.

Step 3: Synthesis of Compound M-3

Under nitrogen atmosphere, the crude product of compound M-2 (0.86 g, 2.53 mmol) was dissolved in toluene (10 mL), and tributyl(1-ethoxyvinyl)stannane (1.72 g, 45.41 mmol) and bis(triphenylphosphine)palladium dichloride (0.18 g, 0.25 mmol) were added. The mixture was reacted at 110° C. for 14 hours. The mixture was filtered and the filtrate was concentrated under reduced pressure. The residue was purified by column chromatography on silica gel (1/1, petroleum ether/ethyl acetate) to give compound M-3.

$^1H$ NMR (400 MHz, $CDCl_3$) δ=7.46-7.39 (m, 2H), 7.23-7.19 (m, 1H), 5.01-4.92 (m, 1H), 4.54 (d, J=2.0 Hz, 1H), 4.35 (t, J=8.0 Hz, 1H), 4.10 (d, J=2.4 Hz, 1H), 3.86 (q, J=8.0 Hz, 2H), 2.97-2.82 (m, 1H), 2.79-2.65 (m, 3H), 2.49-2.36 (m, 2H), 2.19-2.07 (m, 3H), 2.07-1.90 (m, 2H), 1.62-1.55 (m, 1H), 1.37 (t, J=8.0 Hz, 2H), 1.21-1.15 (m, 6H).

Step 4: Synthesis of Intermediate M

To a solution of compound M-3 (0.20 g, 0.60 mmol) in acetone (6 mL) was added concentrated hydrochloric acid (1.2 mL, 14.40 mmol), and the reaction solution was reacted at 25° C. for 2 hours. Water (15 mL) was added to the reaction solution, and sodium bicarbonate solution was added to adjust the pH to 8. The mixture was extracted with ethyl acetate (20 mL×3), washed with saturated brine (20 mL) and water (20 mL), and concentrated under reduced pressure to give intermediate M.

MS-ESI calculated $[M+H]^+$ 304, found 304.

Intermediate N

N

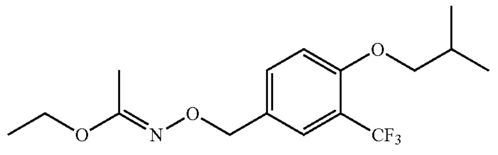

Synthetic Route:

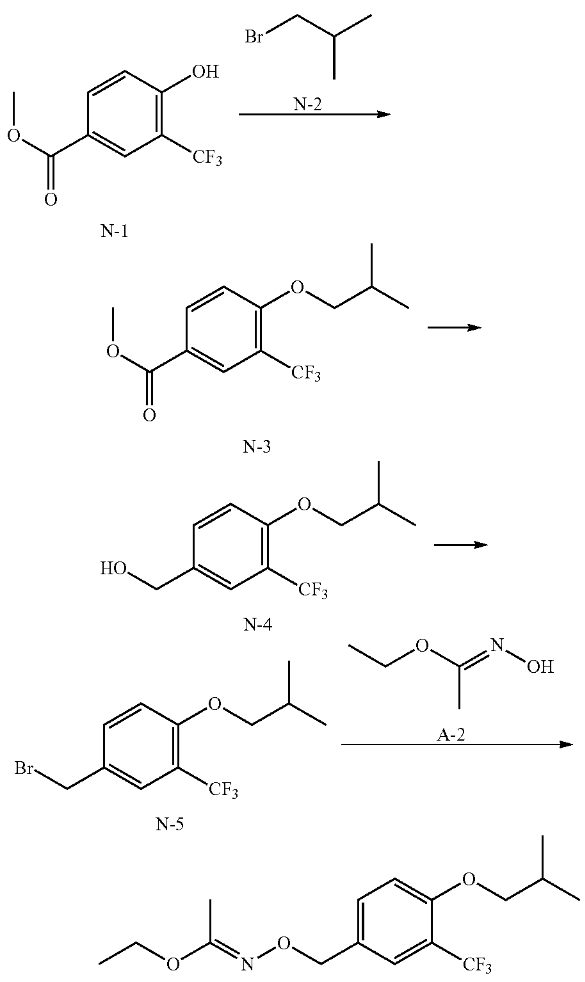

N-1

N-3

N-4

N-5

N

Step 1: Synthesis of Compound N-3

Compound N-1 (3.50 g, 15.9 mmol) was dissolved in N,N-dimethylformamide (35 mL), and potassium carbonate (6.59 g, 47.7 mmol) and compound N-2 (4.36 g, 31.8 mmol) were added to the reaction solution. The reaction mixture was reacted at 85° C. for 2 hours. Water (100 mL) was added to the reaction solution. The mixture was extracted with ethyl acetate (100 mL×3). The combined organic phase was dried over anhydrous sodium sulfate, and filtered. The filtrate was concentrated under reduced pressure. The crude product was purified by column chromatography on silica gel (petroleum ether/ethyl acetate, 1/0, V/V) to give compound N-3.

MS-ESI calculated $[M+H]^+$ 277, found 277.

Step 2: Synthesis of Compound N-4

Lithium aluminum hydride (717 mg, 18.9 mmol) was dissolved in tetrahydrofuran (30 mL), and a solution of compound N-3 (3.48 g, 12.6 mmol) in tetrahydrofuran (15 mL) was added dropwise to the reaction mixture at 0° C. under nitrogen atmosphere. The reaction mixture was stirred at 0~10° C. for 1 hour. Water (0.72 mL), 10% aqueous sodium hydroxide solution (0.72 mL), and water (2.16 mL) were added successively to the reaction solution, and the reaction mixture was stirred at 15° C. for 0.5 h. The suspension was filtered, and the filter cake was washed with ethyl acetate (50 mL×1). The organic phase was washed with saturated brine (40 mL×1), dried over anhydrous sodium sulfate, and filtered. The filtrate was concentrated under reduced pressure to give compound N-4.

$^1$H NMR (400 MHz, $CD_3Cl$) δ=7.57 (s, 1H), 7.46 (br d, J=8.4 Hz, 1H), 6.96 (d, J=8.4 Hz, 1H), 4.65 (s, 2H), 3.81 (d, J=6.4 Hz, 2H), 2.22-2.07 (m, 1H), 1.05 (d, J=6.8 Hz, 6H).

Step 3: Synthesis of Compound N-5

Compound N-4 (3.11 g, 12.5 mmol) was dissolved in tetrahydrofuran (30 mL), and carbon tetrabromide (5.40 g, 16.3 mmol) and triphenylphosphine (3.61 g, 13.8 mmol) were added. The mixture was stirred at 25° C. for 12 hours. The mixture was concentrated under reduced pressure, and the residue was purified by column chromatography on silica gel (petroleum ether/ethyl acetate, 1/0~40/1, V/V) to give compound N-5.

$^1$H NMR (400 MHz, $CD_3Cl$) δ=7.60 (d, J=2.1 Hz, 1H), 7.53-7.48 (m, 1H), 6.94 (d, J=8.5 Hz, 1H), 4.49 (s, 2H), 3.82 (d, J=6.3 Hz, 2H), 2.21-2.09 (m, 1H), 1.05 (d, J=6.8 Hz, 6H).

Step 4: Synthesis of Intermediate N

Compound A-2 (1.54 g, 14.0 mmol) was dissolved in tetrahydrofuran (20 mL), and a solution of potassium tert-butoxide in tetrahydrofuran (1 M, 30.0 mL) was added dropwise at 0° C. The reaction mixture was stirred at 0~5° C. for 1 hour. A solution of compound N-5 (4.65 g, 15.0 mmol) in tetrahydrofuran (20 mL) was added dropwise, and the reaction solution was stirred at 0-20° C. for 1 hour. Saturated aqueous ammonium chloride solution (100 mL) was added. The mixture was extracted with ethyl acetate (100 mL×2), dried over anhydrous sodium sulfate, and filtered. The filtrate was concentrated under reduced pressure. The residue was purified by column chromatography on silica gel (petroleum ether/ethyl acetate, 1/0~20/1, V/V) to give intermediate N.

MS-ESI calculated [M+H]$^+$ 334, found 334.

Intermediate O

O

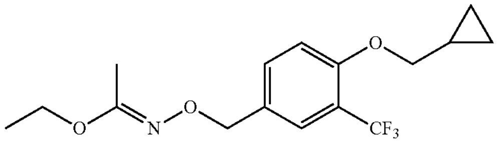

Synthetic Route:

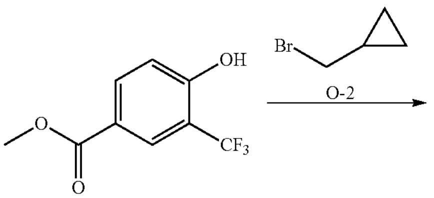

O-1

-continued

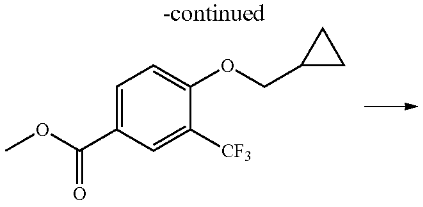

O-3

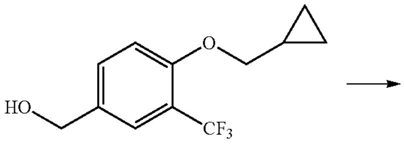

O-4

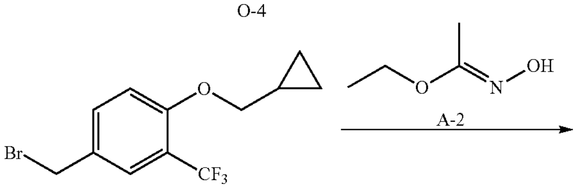

O-5

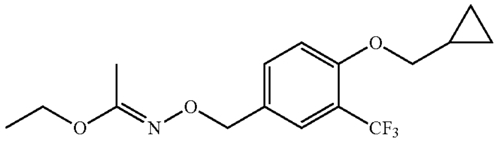

O

Step 1: Synthesis of Compound O-3

Compound O-1 (5.00 g, 22.7 mmol) was dissolved in N,N-dimethylformamide (50 mL), and potassium carbonate (12.6 g, 90.9 mmol) and bromoethylcyclopropane O-2 (1.57 g, 9.26 mmol) were added to the reaction solution. The reaction mixture was reacted at 70° C. for 12 hours. Water (80 mL) was added to the reaction solution. The mixture was extracted with ethyl acetate (50 mL×2). The combined organic phase was dried over anhydrous sodium sulfate (10 g), and filtered. The filtrate was concentrated under reduced pressure. The crude product was purified by column chromatography on silica gel (petroleum ether/ethyl acetate, 1/0 to 40/1, V/V) to give the crude product of compound O-3.

MS-ESI calculated [M+H]$^+$ 275, found 275.

Step 2: Synthesis of Compound O-4

Lithium aluminum hydride (1.39 g, 36.7 mmol) was dissolved in tetrahydrofuran (60 mL) under nitrogen atmosphere, and a solution of the crude product of compound O-3 (6.7 g, 24.43 mmol) in tetrahydrofuran (30 mL) was added dropwise to the reaction mixture at 0° C. The reaction mixture was stirred at 10° C. for 1 hour. Water (1.39 mL), 10% aqueous sodium hydroxide solution (1.39 mL), and water (4.17 mL) were added successively to the reaction solution. The reaction mixture was stirred at 10° C. for 0.5 h. The suspension was filtered, and the filter cake was washed with ethyl acetate (30 mL×2). The organic phase was washed with saturated brine (60 mL×1), dried over anhydrous sodium sulfate, and filtered. The filtrate was concentrated under reduced pressure to give compound O-4.

$^1$H NMR (400 MHz, $CD_3Cl$) δ=7.55 (s, 1H), 7.44 (d, J=8.0 Hz, 1H), 6.95 (br d, J=8.4 Hz, 1H), 4.62 (s, 2H), 3.93 (d, J=6.4 Hz, 2H), 1.30-1.25 (m, 1H), 0.67-0.59 (m, 2H), 0.44-0.35 (m, 2H).

Step 3: Synthesis of Compound O-5

Compound O-4 (5.37 g, 21.8 mmol) was dissolved in tetrahydrofuran (50 mL), and carbon tetrabromide (8.68 g, 26.2 mmol) and triphenylphosphine (6.01 g, 22.9 mmol) were added to the system. The mixture was stirred at 25° C. for 12 hours. The reaction solution was concentrated under reduced pressure, and the resulting residue was purified by column chromatography on silica gel (petroleum ether/ethyl acetate, 1/0~40/1, V/V) to give compound O-5.

$^1$H NMR (400 MHz, $CD_3Cl$) δ=7.62-7.58 (m, 1H), 7.53-7.47 (m, 1H), 6.94 (d, J=8.6 Hz, 1H), 4.49 (s, 2H), 3.95 (d, J=6.6 Hz, 2H), 1.31-1.26 (m, 1H), 0.67-0.61 (m, 2H), 0.43-0.37 (m, 2H).

Step 4: Synthesis of Intermediate O

Compound A-2 (1.40 g, 13.6 mmol) was dissolved in tetrahydrofuran (30 mL), and a solution of potassium tert-butoxide in tetrahydrofuran (1 M, 27.17 mL) was added dropwise at 0° C. The reaction solution was stirred at 0° C. for 1 hour. Then, a solution of compound O-5 (4.20 g, 13.6 mmol) in tetrahydrofuran (30 mL) was added dropwise, and the mixture was stirred at 15° C. for another 12 hours. Saturated aqueous ammonium chloride solution (50 mL) was added to the system. The mixture was extracted with ethyl acetate (50 mL×2), dried over anhydrous sodium sulfate, and filtered. The filtrate was concentrated under reduced pressure, and the resulting residue was purified by column chromatography on silica gel (petroleum ether/ethyl acetate, 40/1, V/V) to give intermediate O.

MS-ESI calculated [M+H]$^+$ 332, found 332.

Intermediate P

P

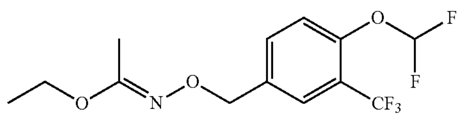

Synthetic Route:

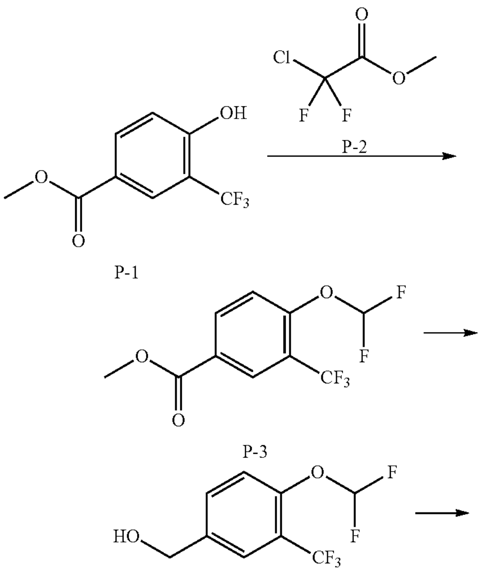

P-1

P-3

P-4

-continued

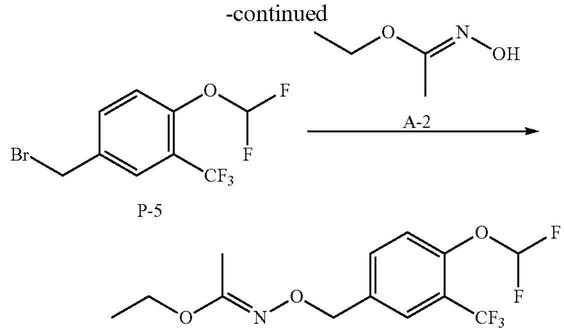

P-5

P

Step 1: Synthesis of Compound P-3

Compound P-1 (1 g, 4.54 mmol), compound P-2 (787.69 mg, 5.45 mmol) and potassium carbonate (941.69 mg, 6.81 mmol) were added to N,N-dimethylformamide (10 mL), and the mixture was then heated to 65° C. to react for 14 hours. The reaction solution was cooled to room temperature, and then water (10 mL) was added. The mixture was extracted with ethyl acetate (10 mL×3). The combined organic phase was dried over anhydrous sodium sulfate, and filtered. The filtrate was concentrated to give compound P-3.

MS-ESI calculated [M+H]$^+$ 271, found 271.

Step 2: Synthesis of Compound P-4

Under nitrogen atmosphere, lithium aluminum tetrahydride (168.59 mg, 4.44 mmol) was dissolved in 10 mL of tetrahydrofuran at 0° C., and compound P-3 (800 mg, 2.96 mmol) in tetrahydrofuran (10 mL) was added dropwise to the reaction system. Then the mixture was reacted at 0-25° C. for 1 hour. Water (0.1 mL), 10% aqueous sodium hydroxide solution (0.1 mL) and water (0.3 mL) were added successively to the system to quench the reaction. The mixture was stirred at 25° C. for 0.5 hours, and then anhydrous sodium sulfate was added. The mixture was filtered and the filtrate was concentrated to give compound P-4.

$^1$H NMR (400 MHz, $CD_3Cl$) δ=7.70-7.53 (m, 1H), 7.47 (d, J=8.6 Hz, 1H), 7.27-7.17 (m, 1H), 6.66-6.23 (m, 1H), 4.65 (s, 2H), 2.04 (s, 1H).

Step 3: Synthesis of Compound P-5

Compound P-4 (415 mg, 1.71 mmol) was dissolved in tetrahydrofuran (4 mL), and carbon tetrabromide (682.04 mg, 2.06 mmol) and triphenylphosphine (472 mg, 1.8 mmol) were added. The mixture was stirred at 25° C. for 12 hours. The reaction solution was directly concentrated under reduced pressure to give compound P-5.

$^1$H NMR (400 MHz, $CD_3Cl$) δ=7.62 (d, J=2.1 Hz, 1H), 7.55-7.48 (m, 1H), 7.28-7.16 (m, 1H), 6.67-6.23 (m, 1H), 4.48-4.29 (m, 2H).

Step 4: Synthesis of Intermediate P

Compound A-2 (150.77 mg, 1.46 mmol) was dissolved in tetrahydrofuran (2 mL), and potassium tert-butoxide (328.13 mg, 2.92 mmol) was added at 0° C. The mixture was then dissolved in tetrahydrofuran (2 mL) at 0-5° C. and the solution was reacted for 1 hour. Then a solution of compound P-5 (446 mg, 1.46 mmol) in tetrahydrofuran (2 mL)

was slowly added dropwise to the reaction solution, and the mixture was reacted at 0-20° C. for 12 hours. After the reaction was completed, the mixture was quenched by adding 10 mL of aqueous ammonium chloride solution (10 mL). The mixture was extracted with ethyl acetate (10 mL×3). The combined organic phase was dried over anhydrous sodium sulfate, and filtered. The filtrate was concentrated to give intermediate P.

MS-ESI calculated $[M+H]^+$ 328, found 328.

Intermediate Q

Q

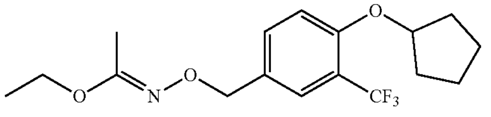

Synthetic Route:

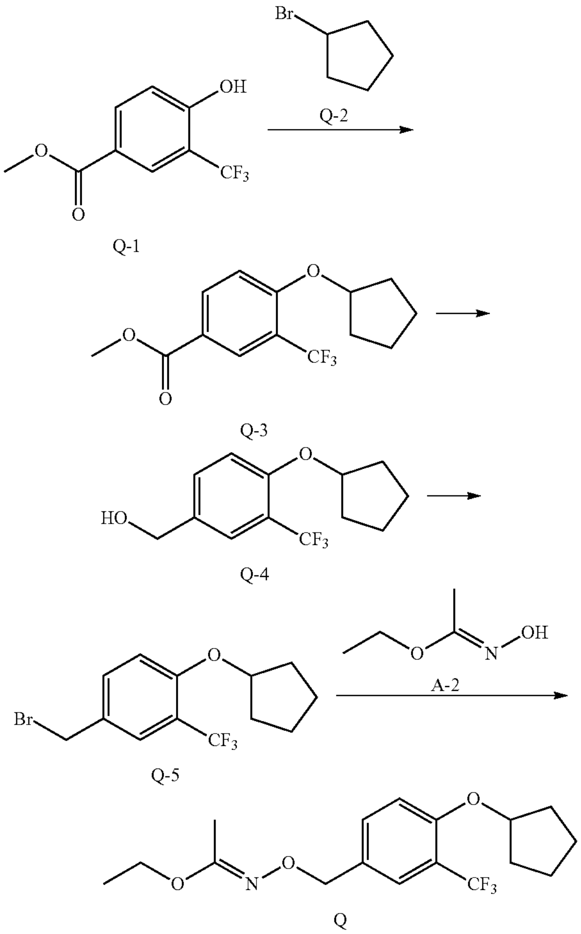

Q-1
Q-3
Q-4
Q-5
Q

Step 1: Synthesis of Compound Q-3

Compound Q-1 (5.50 g, 25.0 mmol) was dissolved in N,N-dimethylformamide (55 mL), and potassium carbonate (13.0 g, 93.9 mmol) and bromocyclopentane Q-2 (10.5 g, 70.4 mmol) were added to the reaction solution. The reaction mixture was reacted at 70° C. for 2 hours. The solvent was removed under reduced pressure, and water (100 mL) was added to the residue. The mixture was extracted with ethyl acetate (100 ml×3), and the organic phase was washed with saturated sodium chloride (50 ml×2). The combined organic phase was dried over anhydrous sodium sulfate, and filtered. The filtrate was concentrated under reduced pressure to give compound Q-3.

$^1$H NMR (400 MHz, $CD_3Cl$) δ=8.25 (d, J=2.1 Hz, 1H), 8.19-8.12 (m, 1H), 7.01 (d, J=8.7 Hz, 1H), 4.98-4.91 (m, 1H), 3.91 (s, 3H), 1.99-1.77 (m, 6H), 1.74-1.60 (m, 2H).

Step 2: Synthesis of Compound Q-4

Lithium aluminum hydride (1.52 g, 40.0 mmol) was dissolved in tetrahydrofuran (75 ml), and a solution of compound Q-3 (7.70 g, 26.7 mmol) in tetrahydrofuran (25 mL) was added dropwise to the reaction mixture at 0° C. under nitrogen atmosphere. The reaction mixture was stirred at 0-25° C. for 1 hour. The batches of intermediate Q-3 (700 mg) were combined, and water (1.5 mL), 15% aqueous sodium hydroxide solution (1.5 mL) and water (4.6 mL) were successively added dropwise to the reaction solution. The reaction mixture was stirred at 15° C. for 0.5 h. The mixture was filtered, and the filter cake was washed with ethyl acetate (50 mL). The organic phase was washed with saturated brine (40 mL), dried over anhydrous sodium sulfate, and filtered. The filtrate was concentrated under reduced pressure to give compound Q-4.

$^1$H NMR (400 MHz, $CD_3Cl$) δ=7.56 (d, J=1.8 Hz, 1H), 7.49-7.42 (m, 1H), 6.98 (d, J=8.6 Hz, 1H), 4.92-4.84 (m, 1H), 4.64 (s, 2H), 1.94-1.86 (m, 4H), 1.85-1.82 (m, 2H), 1.70-1.59 (m, 2H).

Step 3: Synthesis of Compound Q-5

Compound Q-4 (7.00 g, 26.9 mmol) was dissolved in tetrahydrofuran (80 mL), and carbon tetrabromide (10.7 g, 32.3 mmol) and triphenylphosphine (7.41 g, 28.2 mmol) were added. The mixture was stirred at 25° C. for 12 hours. The mixture was concentrated under reduced pressure, and the residue was purified by column chromatography on silica gel (petroleum ether/ethyl acetate=40/1~10/1, V/V) to give compound Q-5.

$^1$H NMR (400 MHz, $CD_3Cl$) δ=7.58 (d, J=2.0 Hz, 1H), 7.52-7.45 (m, 1H), 6.95 (d, J=8.6 Hz, 1H), 4.93-4.83 (m, 1H), 4.49 (s, 2H), 1.96-1.77 (m, 6H), 1.71-1.59 (m, 2H).

Step 4: Synthesis of Intermediate Q

Compound A-2 (2.13 g, 20.6 mmol) was dissolved in tetrahydrofuran (70 mL), and potassium tert-butoxide (4.63 g, 41.3 mL) was added in batches at 0° C. The reaction mixture was stirred at 0° C. for 1 hour, and a solution of compound 5 (6.67 g, 20.6 mmol) in tetrahydrofuran (70 mL) was then added dropwise. The reaction solution was stirred at 0-20° C. for 12 hours. Saturated aqueous ammonium chloride solution (105 mL) was added, and the mixture was extracted with ethyl acetate (100 mL×2). The organic phases were combined, dried over anhydrous sodium sulfate, and filtered. The filtrate was concentrated under reduced pressure. The residue was purified by column chromatography on silica gel (petroleum ether/ethyl acetate=40/1~10/1, V/V) to give intermediate Q.

MS-ESI calculated $[M+H]^+$ 346, found 346.

Intermediate R

R

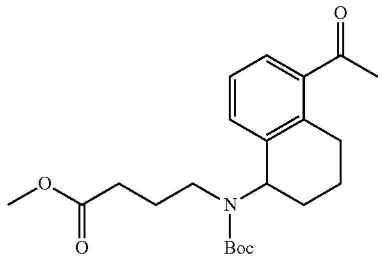

Synthetic Route:

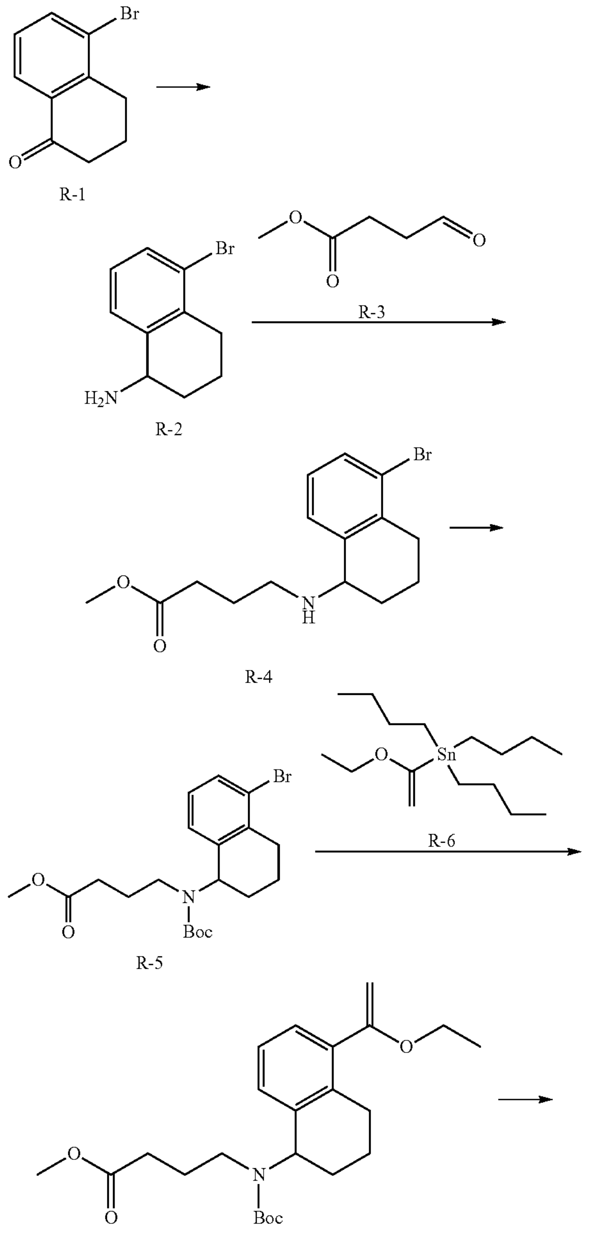

R-1
R-2
R-4
R-5
R-7

-continued

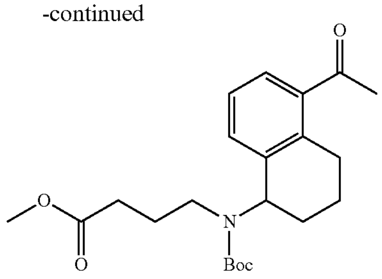

R

Step 1: Synthesis of Compound R-2

Compound R-1 (8.00 g, 35.5 mmol) was dissolved in isopropanol (50 mL), and sodium cyanoborohydride (11.2 g, 178 mmol) and ammonium acetate (54.8 g, 711 mmol) were added to the reaction solution. The mixture was stirred at 15° C. for 4 hours, and then stirred at 90° C. for another 12 hours. The reaction solution was cooled to room temperature and poured into cold water (500 mL). The mixture was adjusted to a pH of 9 with aqueous sodium hydroxide solution. The mixture was extracted with dichloromethane (200 mL×2). The combined organic phase was dried over anhydrous sodium sulfate, and filtered. The filtrate was concentrated under reduced pressure to give compound R-2.

Step 2: Synthesis of R-4 Formate

Compound R-2 (8.4 g, 29.8 mmol), compound R-3 (4.85 g, 41.8 mmol) and glacial acetic acid (1.71 mL, 29.8 mmol) were dissolved in dichloromethane (100 mL), and the reaction mixture was stirred at 25° C. for 1 h. Sodium borohydride acetate (19.0 g, 89.5 mmol) was then added to the reaction mixture, and the mixture was stirred at 30° C. for 12 hours. Water was added to the reaction solution (150 mL), and the mixture was extracted with dichloromethane (100 mL×2). The combined organic phase was dried over anhydrous sodium sulfate (30 g), and filtered. The filtrate was concentrated under reduced pressure to give a crude product. The crude product was separated by high performance liquid chromatography (Column: Phenomenex lμna C18 250×50 mm×10 μm; Mobile phase: 0.225% aqueous formic acid-acetonitrile; Gradient: 15%-45% acetonitrile, 15 min) to give compound R-4 formate.

MS-ESI calculated $[M+H]^+$ 326 and 328, found 326 and 328.

Step 3: Synthesis of Compound R-5

Compound R-4 formate (1.67 g, 3.77 mmol) was dissolved in dichloromethane (25 mL), and triethylamine (2.10 mL, 15.1 mmol) and di-tert-butyl dicarbonate (1.23 g, 5.66 mmol) were added to the reaction solution. The reaction mixture was stirred at 25° C. for 12 hours. Water (30 mL) was added to the reaction solution. The mixture was extracted with dichloromethane (20 mL×2). The combined organic phase was dried over anhydrous sodium sulfate (10 g), and filtered. The filtrate was concentrated under reduced pressure to give a residue. The residue was purified by column chromatography on silica gel (petroleum ether/ethyl acetate, 50/1~20/1, V/V) to give compound R-5.

MS-ESI calculated $[M+H]^+$ 426 and 428, found 426 and 428.

Step 4: Synthesis of Compound R-7

Compound R-5 (940 mg, 2.20 mmol), bis(triphenylphosphine)palladium dichloride (155 mg, 220 μmol) and compound R-6 (5.43 mmol, 1.83 mL) were dissolved in toluene (15 mL). The atmosphere was replaced three times with nitrogen gas. The reaction mixture was stirred at 110° C. under nitrogen atmosphere for 6 hours. Saturated potassium fluoride aqueous solution (50 mL) was added to the reaction solution at 20° C., and the reaction mixture was stirred for 1 hour. The reaction mixture was filtered, and extracted with ethyl acetate (40 mL×2). The combined organic phase was dried over anhydrous sodium sulfate, and filtered. The filtrate was concentrated under reduced pressure to give the crude product of compound R-7.

MS-ESI calculated $[M+H]^+$ 418, found 418.

Step 5: Synthesis of Intermediate R

The crude product of compound R-7 (1.80 g, 4.31 mmol) was dissolved in acetone (30 mL), and hydrochloric acid (1 M, 6.47 mL) was added to the reaction solution. The reaction mixture was stirred at 15° C. for 10 minutes. Saturated aqueous sodium bicarbonate solution (50 mL) was added to the reaction solution, and the mixture was extracted with dichloromethane (40 mL×2). The combined organic phase was dried over anhydrous sodium sulfate, and filtered. The filtrate was concentrated under reduced pressure. The crude product was purified by column chromatography on silica gel (petroleum ether/ethyl acetate, 20/1~5/1, V/V) to give intermediate R.

MS-ESI calculated $[M+Na]^+$ 412, found 412.

Intermediate S

S

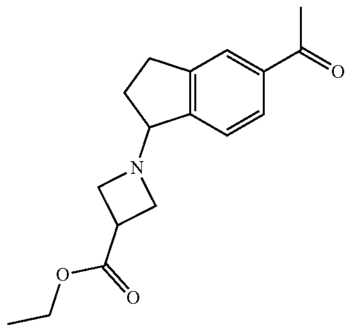

Synthetic Route:

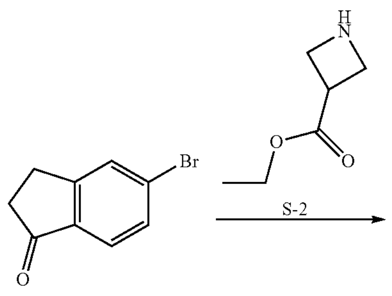

D-3

-continued

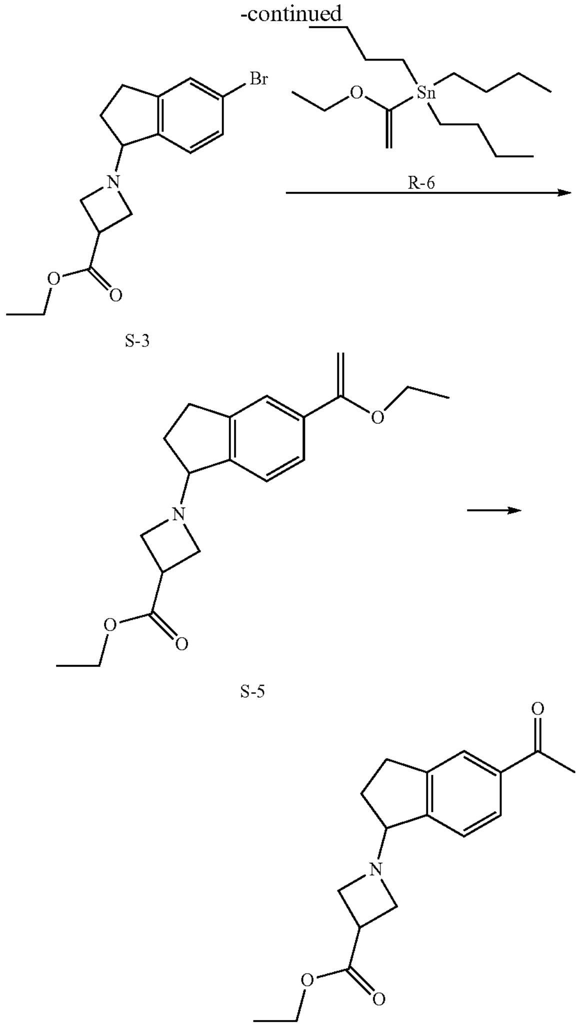

S-3

S-5

S

Step 1: Synthesis of Compound S-3

Compound S-2 (2.47 g, 14.9 mmol) was dissolved in dichloromethane (20 mL), and triethylamine (2.08 mL, 14.9 mmol) was added to the reaction solution. The reaction mixture was stirred at 25° C. for 0.5 hours. Compound D-3 (3.00 g, 14.2 mmol) and acetic acid (3.25 mL, 56.9 mmol) were added. The reaction mixture was stirred at 25° C. for 0.5 hours. Sodium borohydride acetate (7.53 g, 35.5 mmol) was added to the reaction solution. The reaction mixture was stirred at 25° C. for 12 hours. Saturated aqueous sodium bicarbonate solution (100 mL) was added to the reaction solution, and the mixture was extracted with dichloromethane (100 mL×3). The combined organic phase was washed with saturated brine (100 mL×1), dried over anhydrous sodium sulfate, and filtered. The filtrate was concentrated under reduced pressure. The crude product was purified by column chromatography on silica gel (petroleum ether/ethyl acetate, 20/1 to 2/1, V/V) to give compound S-3.

MS-ESI calculated $[M+H]^+$ 324 and 326, found 324 and 326.

$^1H$ NMR (400 MHz, $CD_3Cl$) δ=7.38 (s, 1H), 7.30-7.25 (m, 1H), 7.13 (d, J=8.0 Hz, 1H), 4.19-4.13 (m, 2H), 3.88-3.80 (m, 1H), 3.64-3.57 (m, 1H), 3.56-3.49 (m, 1H), 3.46 (t,

J=7.2 Hz, 1H), 3.41-3.35 (m, 1H), 3.35-3.27 (m, 1H), 3.10-2.98 (m, 1H), 2.84-2.73 (m, 1H), 2.16-2.07 (m, 1H), 1.98-1.88 (m, 1H), 1.29-1.26 (m, 3H).

Step 2: Synthesis of Compound S-5

Compound S-3 (1.50 g, 4.63 mmol), bis(triphenylphosphine)palladium dichloride (325 mg, 463 μmol) and compound R-6 (9.25 mmol, 3.12 mL) were dissolved in toluene (20 mL), and the atmosphere was replaced three times with nitrogen gas. The reaction mixture was stirred at 110° C. under nitrogen atmosphere for 6 hours. Saturated potassium fluoride aqueous solution (50 mL) was added to the reaction solution at 20° C. The reaction mixture was filtered and extracted with ethyl acetate (50 mL×2). The combined organic phase was dried over anhydrous sodium sulfate (10 g), and filtered. The filtrate was concentrated under reduced pressure. The crude product was purified by column chromatography on silica gel (petroleum ether/ethyl acetate, 5/1 to 3/1, V/V) to give compound S-5.

MS-ESI calculated $[M+H]^+$ 316, found 316.

Step 3: Synthesis of Intermediate S

Compound S-5 (250 mg, 793 μmol) was dissolved in acetone (40 mL), and hydrochloric acid (12 M, 2.64 mL) was added to the reaction solution. The reaction mixture was stirred at 20° C. for 1 hour. Saturated aqueous sodium bicarbonate solution (30 mL) was added to the reaction solution, and the mixture was extracted with dichloromethane (30 mL×3). The combined organic phase was dried over anhydrous sodium sulfate, and filtered. The filtrate was concentrated under reduced pressure, and the crude product was separated by thin-layer chromatography (petroleum ether/ethyl acetate, 1/1, V/V) to give intermediate S.

MS-ESI calculated $[M+H]^+$ 288, found 288.

$^1H$ NMR (400 MHz, $CD_3Cl$) δ=7.85 (br d, J=4.6 Hz, 2H), 7.38 (br d, J=7.7 Hz, 1H), 4.00 (br s, 1H), 3.74-3.61 (m, 2H), 3.57 (br d, J=6.7 Hz, 1H), 3.46 (br d, J=7.2 Hz, 1H), 3.41-3.33 (m, 1H), 3.19-3.04 (m, 2H), 2.93-2.81 (m, 2H), 2.59 (s, 3H), 2.23-2.14 (m, 1H), 2.02-1.98 (m, 1H), 1.30-1.27 (m, 3H).

Intermediate T

T

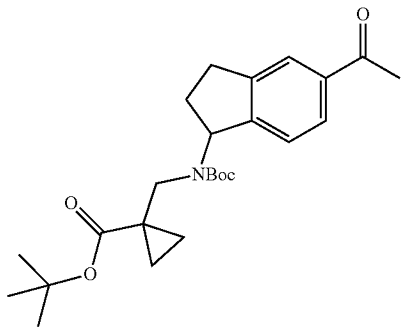

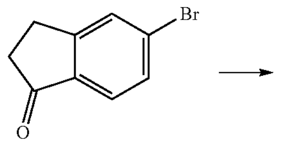

D-3

-continued

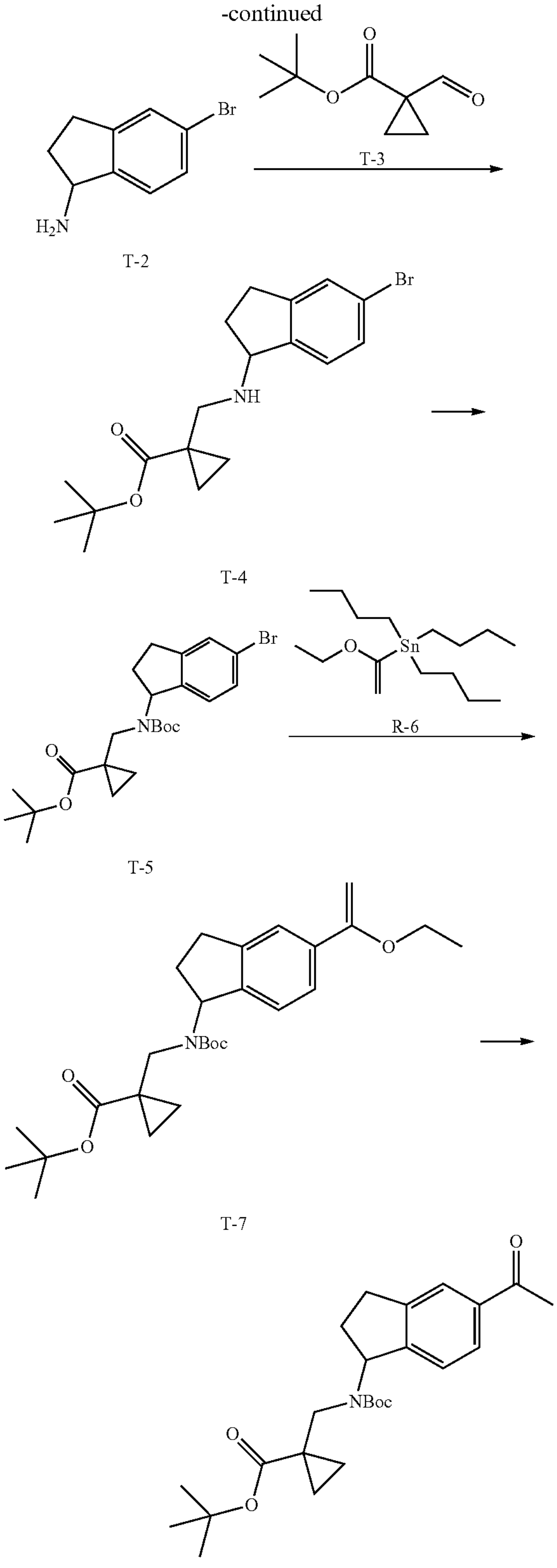

T-2

T-4

T-5

T-7

T

Step 1: Synthesis of Compound T-2

Compound D-3 (5.00 g, 23.69 mmol) was dissolved in methanol (75 mL), and ammonium formate (15 g, 237.88 mmol) was added. The mixture was stirred at 25° C. for 1 hour, and sodium cyanoborohydride (4.5 g, 71.61 mmol) was added to the system. The system was heated to 60° C. and stirred for 2 hours. The reaction solution was concentrated under reduced pressure to remove part of the solvent, and then water (20 mL) was added to the system. The mixture was extracted with dichloromethane (50 mL×3). The combined organic phase was washed with water (50 mL×2), dried over anhydrous sodium sulfate, and filtered. The filtrate was concentrated under reduced pressure to give a residue. A solution of hydrogen chloride in ethyl acetate (3 mL, 4 M) was added to the residue. The mixture was stirred at 30° C. for 0.5 hours, and then filtered to give a solid. The solid was dissolved in water, and the pH was adjusted to 9 with 5% aqueous sodium carbonate solution. The aqueous phase was extracted with ethyl acetate (150 mL×3). The combined organic phase was washed with water (50 mL×2), dried over anhydrous sodium sulfate, and filtered. The filtrate was directly concentrated under reduced pressure to give compound T-2.

Step 2: Synthesis of Compound T-4

Compound T-2 (1.37 g, 6.34 mmol) and compound T-3 (2.16 g, 12.68 mmol) were dissolved in dichloromethane (35 mL), and acetic acid (380.87 mg, 6.34 mmol) was added. The mixture was stirred at 25° C. for 10 hours, and sodium borohydride acetate (4.03 g, 19.03 mmol) was added to the system. The mixture was stirred at 25° C. for 3 hours. 10% aqueous sodium bicarbonate solution (10 mL) was added to the reaction solution, and the mixture was extracted with dichloromethane (10 mL×3). The combined organic phase was washed with saturated brine (10 mL×2), dried over anhydrous sodium sulfate, and filtered. The filtrate was concentrated under reduced pressure to give the crude product of compound T-4.

MS-ESI calculated $[M+H]^+$ 366 and 368, found 366 and 368.

Step 3: Synthesis of Compound T-5

The crude product of compound T-4 (3.8 g, 10.37 mmol) was dissolved in dichloromethane (120 mL), and triethylamine (3.15 g, 31.12 mmol) and di-tert-butyl dicarbonate (3.40 g, 15.56 mmol) were added. The mixture was stirred at 25° C. for 12 hours. Water (20 mL) was added to the reaction solution, and the mixture was extracted with dichloromethane (20 mL×2). The combined organic phase was dried over anhydrous sodium sulfate, and filtered. The filtrate was concentrated under reduced pressure to give a crude product, and the crude product was purified by column chromatography on silica gel (petroleum ether/ethyl acetate, 40/1~10/1, V/V) to give compound T-5.

Step 4: Synthesis of Compound T-7

Compound T-5 (2.3 g, 4.93 mmol) was dissolved in toluene (25 mL) under nitrogen atmosphere, and tributyl(1-ethoxyvinyl)stannane (5.24 μg, 14.51 mmol) and bis(triphenylphosphine)palladium dichloride (0.35 g, 0.49 mmol) were added. The reaction solution was stirred at 110° C. for 6 hours. Saturated aqueous potassium fluoride solution (100 mL) was added to the reaction solution and the mixture was stirred at 20° C. for 1 hour. The reaction system was filtered, and the filtrate was extracted with ethyl acetate (100 mL×2). The combined organic phase was dried over anhydrous sodium sulfate and filtered. The filtrate was concentrated under reduced pressure to give the crude product of compound T-7.

MS-ESI calculated $[M+H]^+$ 458, found 458.

Step 5: Synthesis of Intermediate T

The crude product of compound T-7 (2.52 g, 5.51 mmol) was dissolved in dichloromethane (25 mL), and acetic acid (25 mL, 437.12 mmol) was added. The reaction solution was stirred at 25° C. for 2 hours. The reaction solution was concentrated under reduced pressure to remove part of the solvent, and 10% aqueous sodium bicarbonate solution (50 mL) was added. The mixture was extracted with ethyl acetate (60 mL×3). The combined organic phase was washed sequentially with water (50 mL) and saturated brine (100 mL), dried over anhydrous sodium sulfate, and filtered. The filtrate was concentrated under reduced pressure to give intermediate T as a residue.

MS-ESI calculated $[M+H]^+$ 288, found 288.

Intermediate U

U

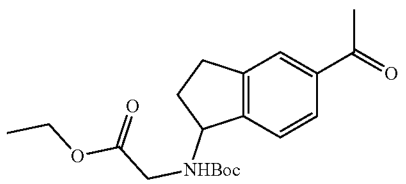

Synthetic Route:

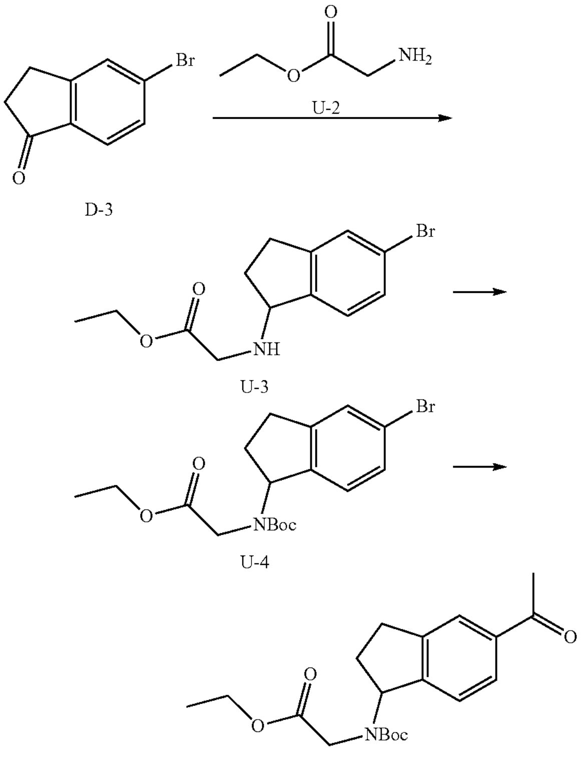

D-3

U-2

U-3

U-4

U

Step 1: Synthesis of Compound U-3

Compound U-2 (13.2 g, 94.8 mmol) was dissolved in dichloromethane (100 mL), and triethylamine (6.59 mL, 47.4 mmol) was added dropwise. The mixture was stirred at 20° C. for 30 minutes, and then compound D-3 (10.0 g, 47.4 mmol) and acetic acid (8.13 mL, 142 mmol) were added to the system. The mixture was stirred at 20° C. for 30 minutes, and sodium borohydride acetate (30.1 g, 142 mmol) was added. The reaction solution was stirred at 20° C. for 12 hours. Water (50 mL) was added to the reaction solution, and the mixture was extracted with ethyl acetate (50 mL×3). The combined organic phase was washed with saturated aqueous sodium chloride solution (50 mL×2), dried over anhydrous sodium sulfate, and filtered. The filtrate was concentrated under reduced pressure to give a residue. The residue was purified by column chromatography on silica gel (1/1, petroleum ether/ethyl acetate, V/V) to give compound U-3.

MS-ESI calculated $[M+H]^+$ 298 and 300, found 298 and 300.

Step 2: Synthesis of Compound U-4

Compound U-3 (10.5 g, 35.1 mmol) was dissolved in dichloromethane (100 mL), and di-tert-butyl dicarbonate (9.18 g, 42.1 mmol) and triethylamine (14.6 mL, 105 mmol) were added to the system. The mixture was stirred at 25° C. for 8 hours. Water (50 mL) was added to the reaction solution. The mixture was extracted with dichloromethane (50 mL×2). The combined organic phase was washed with saturated aqueous sodium chloride solution (20 mL×2), dried over anhydrous sodium sulfate, and filtered. The filtrate was concentrated under reduced pressure to give a residue. The obtained residue was purified by column chromatography on silica gel (5/1, petroleum ether/ethyl acetate, V/V) to give compound U-4.

MS-ESI calculated $[M+Na]^+$ 420 and 422, found 420 and 422.

Step 3: Synthesis of Intermediate U

Compound U-4 (2.00 g, 5.02 mmol), vinyl n-butyl ether (1.94 mL, 15.1 mmol), palladium acetate (56.4 mg, 251 μmol), 1,3-bis(diphenylphosphino)propane (207 mg, 502 μmol) and triethylamine (839 μL, 6.03 mmol) were dissolved in 1-butyl-3-methylimidazolium tetrafluoroborate (8 mL). The atmosphere was replaced three times with nitrogen. The mixture was stirred at 110° C. under nitrogen for 12 hours. Water (50 mL) was added to the reaction solution, and the mixture was extracted with ethyl acetate (50 mL×3). The combined organic phase was washed with saturated aqueous sodium chloride solution (50 mL×2), dried over anhydrous sodium sulfate, and filtered. The filtrate was concentrated under reduced pressure, and the resulting residue was purified by column chromatography on silica gel (3/1, petroleum ether/ethyl acetate, V/V) to give intermediate U.

MS-ESI calculated $[M-100+H]^+$ 262, found 262.

Intermediate V

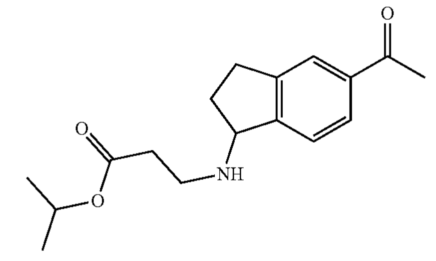

V

Synthetic Route:

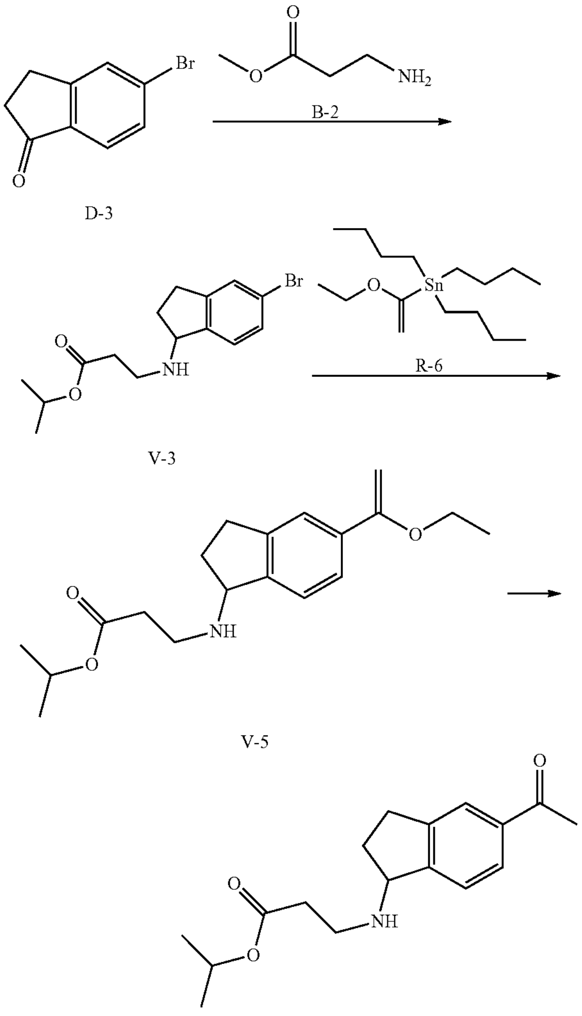

D-3

V-3

V-5

V

Step 1: Synthesis of Compound V-3

Compound B-2 (3.97 g, 28.43 mmol), compound D-3 (5 g, 23.69 mmol) and triethylamine (9.89 mL, 71.07 mmol) were dissolved in tetrahydrofuran (50 mL), and tetraisopropyl titanate (13.47 g, 47.38 mmol) was added dropwise. The mixture was stirred at 65° C. for 12 hours, and then methanol (10 mL), acetic acid (10 mL) and sodium cyanoborohydride (2.98 g, 47.38 mmol) were added to the system. The mixture was stirred at 25° C. for 2 hours. Water (100 mL) was added to the reaction solution and the mixture was stirred for 0.5 hours. The reaction solution was filtered through celite, and the filtrate was extracted with ethyl acetate (50 mL×3). The combined organic phase was washed with saturated aqueous sodium chloride solution (100 mL×1), dried over anhydrous sodium sulfate, and filtered. The filtrate was concentrated under reduced pressure to give a residue. The residue was purified by column chromatography on silica gel (2/1, petroleum ether/ethyl acetate, V/V) to give compound V-3.

Step 2: Synthesis of Compound V-5

Compound V-3 (2.00 g, 6.13 mmol), bis(triphenylphosphine)palladium dichloride (430 mg, 613 μmol) and compound R-6 (14.5 mmol, 4.91 mL) were dissolved in toluene (20 mL), and the atmosphere was replaced three times with nitrogen. The reaction mixture was stirred at 110° C. under nitrogen atmosphere for 6 hours. Saturated potassium fluoride aqueous solution (200 mL) was added to the reaction solution at 20° C. The mixture was filtered and extracted with ethyl acetate (200 mL×2). The combined organic phase was dried over anhydrous sodium sulfate, and filtered. The filtrate was concentrated under reduced pressure to give compound V-5.

MS-ESI calculated $[M+H]^+$ 318, found 318.

Step 3: Synthesis of Intermediate V

Compound V-5 (2.00 g, 6.30 μmol) was dissolved in acetone (40 mL), and hydrochloric acid (1 M, 12.6 mL) was added to the reaction solution. The reaction mixture was stirred at 25° C. for 2 hours. Saturated aqueous sodium bicarbonate solution (300 mL) was added to the reaction solution, and the mixture was extracted with dichloromethane (100 mL×3). The combined organic phase was dried over anhydrous sodium sulfate, and filtered. The filtrate was concentrated under reduced pressure, and purified by column chromatography on silica gel (petroleum ether/ethyl acetate, 5/1~2/1, V/V) to give intermediate V.

MS-ESI calculated $[M+H]^+$ 290, found 290.

Example 1

1

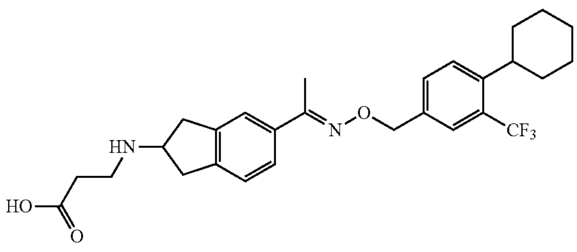

Synthetic Route:

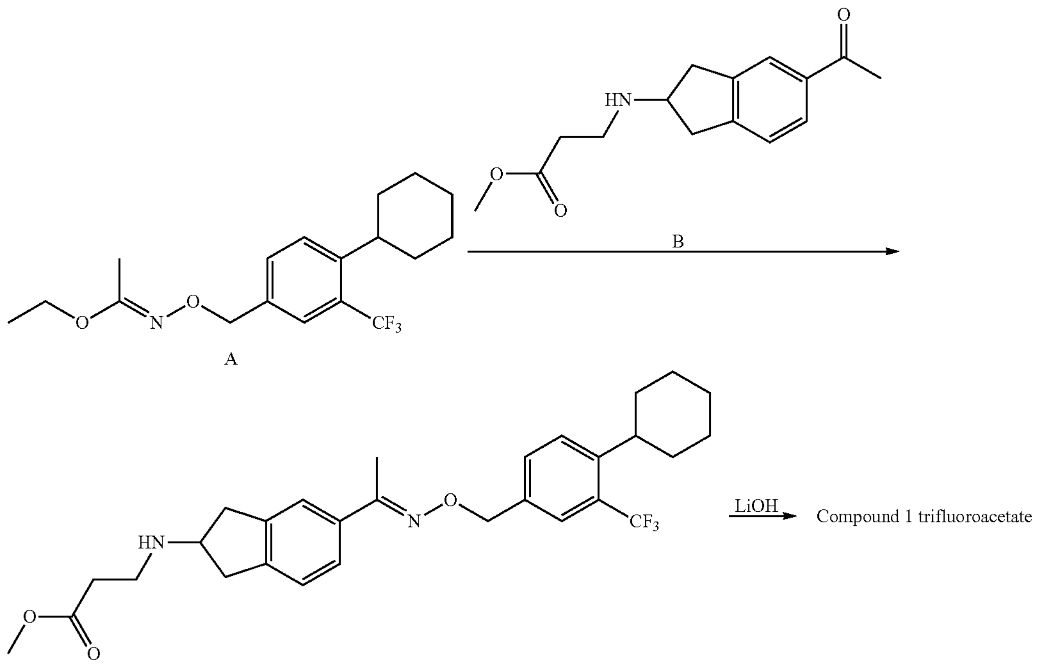

Step 1: Synthesis of Compound 1-1

Intermediate A (0.26 g, 0.75 mmol) was dissolved in methanol (10 mL), and hydrogen chloride/ethyl acetate (3.11 mL, 12.44 mmol) was added. The reaction solution was stirred at 25° C. for 0.5 hours. Triethylamine (1.01 g, 9.95 mmol) and intermediate B (0.13 g, 0.50 mmol) were added to the reaction solution, and the reaction solution was stirred at 60° C. for 12 hours. The reaction solution was concentrated under reduced pressure, and the residue was purified by column chromatography on silica gel (10/1, dichloromethane/methanol) to give compound 1-1.

MS-ESI calculated $[M+H]^+$ 517, found 517.

Step 2: Synthesis of Compound 1 Trifluoroacetate

Compound 1-1 (0.16 g, 0.31 mmol) was dissolved in tetrahydrofuran (5 mL) and water (1 mL), and lithium hydroxide monohydrate (0.26 g, 6.19 mmol) was added. The reaction solution was stirred at 25° C. for 12 hours. 1 M hydrochloric acid was added to the reaction solution until the pH was 4. The reaction solution was concentrated under reduced pressure, and the obtained crude product was separated by preparative high performance liquid chromatography (Column: Boston Green ODS 150×30 mm×5 m; Mobile phase: 0.075% trifluoroacetic acid in water-acetonitrile; Gradient: 49%-79% acetonitrile, 8 min) to give compound 1 trifluoroacetate.

MS-ESI calculated $[M+H]^+$ 503, found 503.

$^1H$ NMR (400 MHz, $CD_3OD$) δ=7.64 (s, 1H), 7.60-7.57 (m, 2H), 7.55-7.51 (m, 2H), 7.31-7.27 (m, 2H), 5.21 (s, 2H), 4.16-4.07 (m, 1H), 3.48-3.39 (m, 2H), 3.20-3.10 (m, 2H), 2.96-2.88 (m, 1H), 2.65 (t, J=8.0 Hz, 2H), 2.25 (s, 3H), 1.90-1.75 (m, 6H), 1.58-1.34 (m, 6H).

Example 2

2

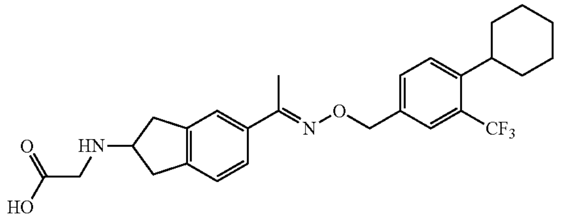

Synthetic Route:

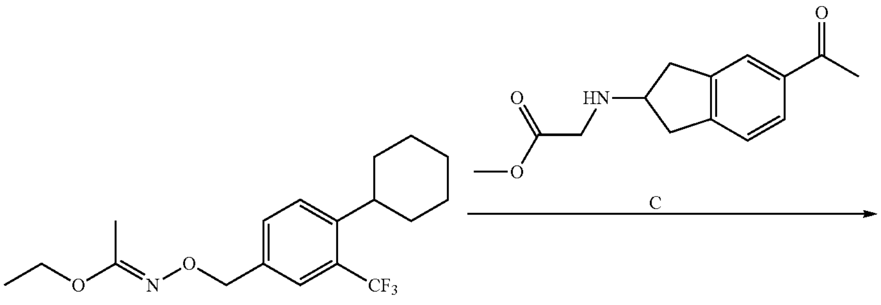

A

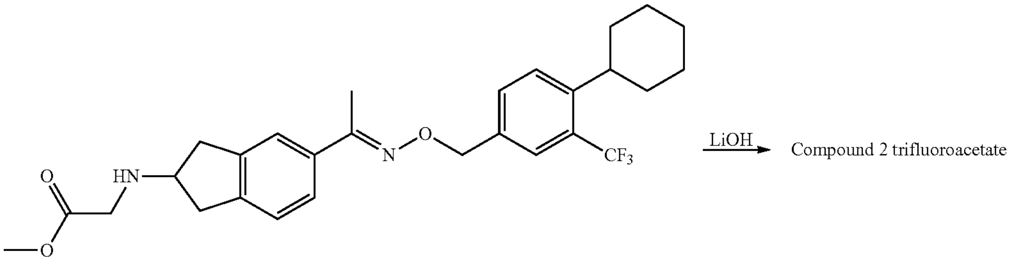

2-1

Step 1: Synthesis of Compound 2-1

Intermediate A (0.04 g, 0.12 mmol) was dissolved in methanol (10 mL), and hydrogen chloride/ethyl acetate (0.51 mL, 2.02 mmol) was added. The reaction solution was stirred at 25° C. for 0.5 hours. Triethylamine (0.16 g, 1.62 mmol) and intermediate C (0.02 g, 0.08 mmol) were added to the reaction solution, and the reaction solution was stirred at 60° C. for 12 hours. The reaction solution was concentrated under reduced pressure, and the residue was purified by column chromatography on silica gel (1/1, petroleum ether/ethyl acetate) to give compound 2-1.

$^1H$ NMR (400 MHz, $CD_3OD$) δ=7.64 (s, 1H), 7.61-7.56 (m, 1H), 7.55-7.51 (m, 1H), 7.47 (s, 1H), 7.41 (d, J=8.0 Hz, 1H), 7.18 (d, J=8.0 Hz, 1H), 5.19 (s, 2H), 3.73 (s, 3H), 3.66-3.59 (m, 1H), 3.46 (s, 2H), 3.18-3.11 (m, 2H), 2.96-2.88 (m, 1H), 2.81-2.73 (m, 2H), 2.25-2.21 (m, 3H), 1.89-1.83 (m, 2H), 1.80-1.76 (m, 1H), 1.81-1.74 (m, 2H), 1.58-1.48 (m, 2H), 1.41-1.28 (m, 3H).

Step 2: Synthesis of Compound 2 Trifluoroacetate

Compound 2-1 (0.03 g, 0.05 mmol) was dissolved in tetrahydrofuran (4 mL) and water (1 mL), and lithium hydroxide monohydrate (0.04 g, 1.00 mmol) was added. The reaction solution was stirred at 25° C. for 12 hours. 1 M hydrochloric acid was added to the reaction solution until the pH was 4. The reaction solution was concentrated under reduced pressure, and the obtained crude product was separated by preparative high performance liquid chromatography (Column: Boston Green ODS 150×30 mm×5 m; Mobile phase: 0.075% trifluoroacetic acid in water-acetonitrile; Gradient: 50%-80% acetonitrile, 8 min) to give compound 2 trifluoroacetate.

MS-ESI calculated $[M+H]^+$ 489, found 489.

$^1H$ NMR (400 MHz, $CD_3OD$) δ=7.64 (s, 1H), 7.57 (s, 2H), 7.54-7.50 (m, 2H), 7.27 (d, J=7.8 Hz, 1H), 5.20 (s, 2H), 4.16-4.06 (m, 1H), 3.79 (s, 2H), 3.45-3.37 (m, 2H), 3.18-3.09 (m, 2H), 2.96-2.87 (m, 1H), 2.24 (s, 3H), 1.90-1.82 (m, 2H), 1.81-1.74 (m, 3H), 1.55-1.34 (m, 5H).

Example 3

3

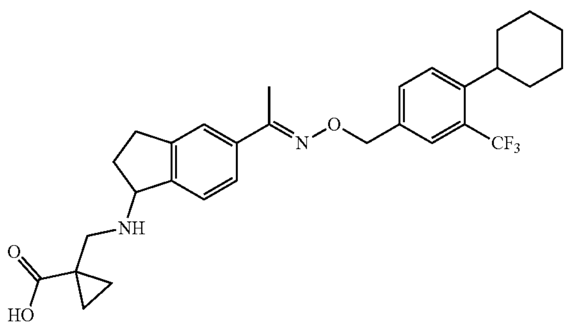

Synthetic Route:

stirred at 25° C. for 0.5 hours. Triethylamine (0.34 g, 3.32 mmol) and intermediate D (0.05 g, 0.17 mmol) were added to the reaction solution, and the reaction solution was stirred at 60° C. for 12 hours. The reaction solution was concentrated under reduced pressure, and the residue was purified by column chromatography on silica gel (10/1, dichloromethane/methanol) to give compound 3-1.

MS-ESI calculated $[M+H]^+$ 558, found 558.

Step 2: Synthesis of Compound 3 Trifluoroacetate

Compound 3-1 (0.04 g, 0.06 mmol) was dissolved in tetrahydrofuran (4 mL), methanol (2 mL) and water (1 mL), and sodium hydroxide (0.56 g, 14 mmol) was added. The reaction solution was stirred at 60° C. for 2 hours. 12 M hydrochloric acid was added to the reaction solution until the pH was 4. The reaction solution was concentrated under reduced pressure, and the obtained crude product was separated by preparative high performance liquid chromatography (Column: Boston Green ODS 150x30 mmx5 m; Mobile phase: 0.075% trifluoroacetic acid in water-acetonitrile; Gradient: 53%-83% acetonitrile, 8 min) to give compound 3 trifluoroacetate.

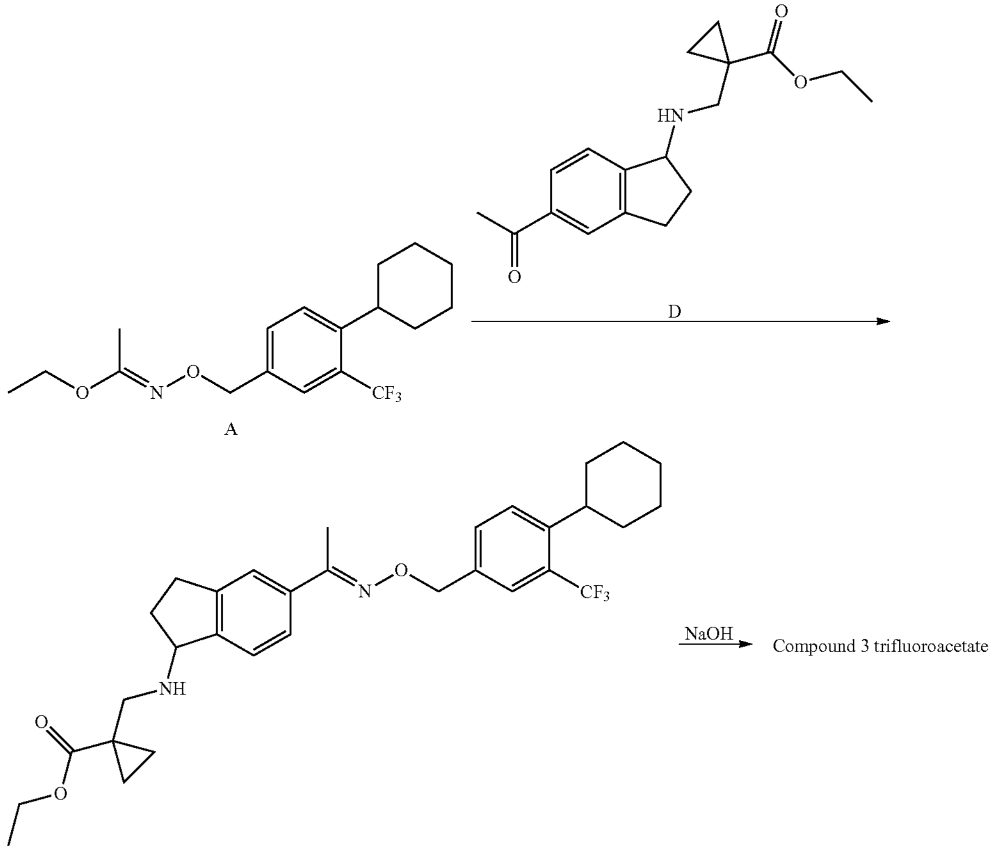

3-1

Step 1: Synthesis of Compound 3-1

Intermediate A (0.09 g, 0.25 mmol) was dissolved in methanol (10 mL), and hydrogen chloride/ethyl acetate (1.04 mL, 4.15 mmol) was added. The reaction solution was MS-ESI calculated $[M+H]^+$ 529, found 529.

$^1H$ NMR (400 MHz, $CD_3OD$) δ=7.67-7.52 (m, 6H), 5.23 (s, 2H), 3.17-3.20 (m, 2H), 3.08-2.86 (m, 2H), 2.67-2.55 (m, 1H), 2.31-2.40 (m, 1H), 2.27 (s, 3H), 1.91-1.73 (m, 5H), 1.60-1.28 (m, 9H), 0.97-1.11 (m, 2H).

Example 4

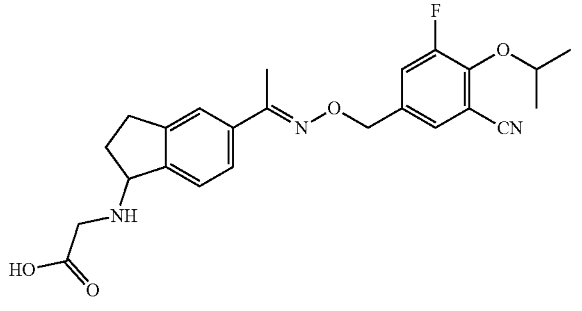

Synthetic Route:

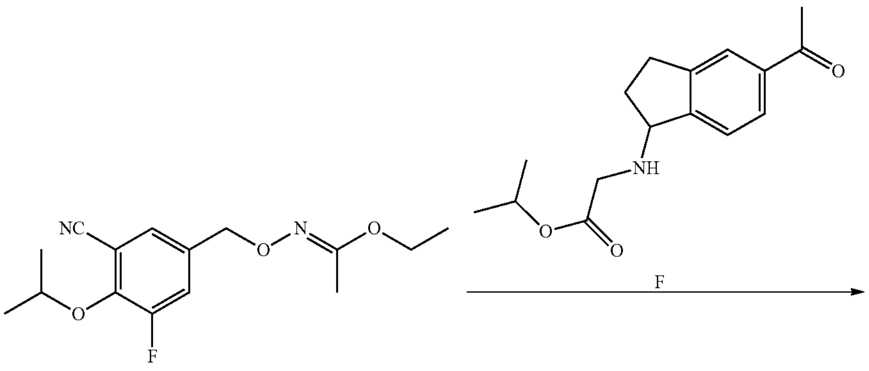

E

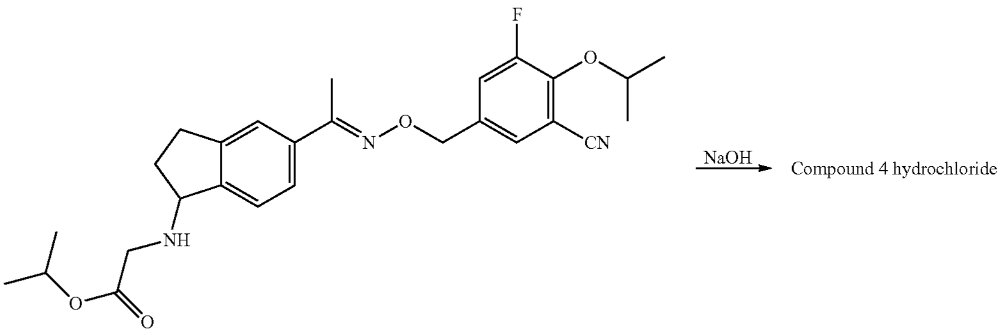

4-1

Step 1: Synthesis of Compound 4-1

Under nitrogen atmosphere, a solution of intermediate E (0.15 g, 0.51 mmol) in methanol (8 mL) was added to hydrochloric acid/ethyl acetate (3.25 mL, 13.02 mmol), and the reaction solution was stirred at 25° C. for 0.5 hours. Triethylamine (0.93 g, 9.17 mmol) was added dropwise to the reaction solution, and intermediate F (0.11 g, 0.41 mmol) was added. The reaction solution was stirred at 60° C. for 14 hours. The mixture was concentrated under reduced pressure, and the residue was purified by column chromatography on silica gel (1/1, petroleum ether/ethyl acetate) to give compound 4-1.

Step 2: Synthesis of Compound 4 Hydrochloride

Under nitrogen atmosphere, compound 4-1 (0.15 g, 0.31 mmol) was dissolved in tetrahydrofuran (10 mL) and water (2 mL), and sodium hydroxide (0.97 g, 24.12 mmol) was added. The mixture was stirred at 60° C. for 2 hours. The reaction solution was concentrated under reduced pressure, and the crude product was separated by high performance liquid chromatography (Column: Phenomenex Luna C18 150×30 mm×5 m; Mobile phase: 0.05% hydrochloric acid in water-acetonitrile; Gradient: 29%-49% acetonitrile, 7 min) to give compound 4 hydrochloride.

MS-ESI calculated $[M+H]^+$ 440, found 440.

$^1H$ NMR (400 MHz, $CD_3OD$) δ=7.68-7.48 (m, 6H), 5.19 (s, 2H), 4.72-4.65 (m, 1H), 3.83 (s, 2H), 3.26-3.16 (m, 1H), 3.06-2.96 (m, 1H), 2.64-2.54 (m, 1H), 2.30-2.24 (m, 4H), 1.37 (d, J=4.0 Hz, 6H).

Example 5

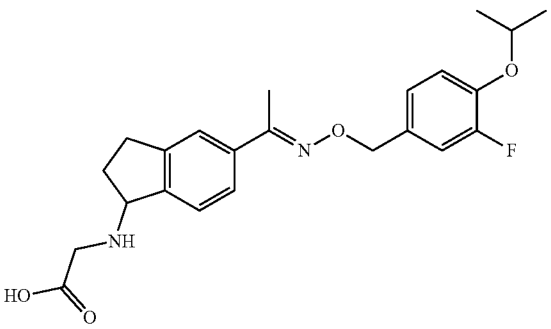

Synthetic Route:

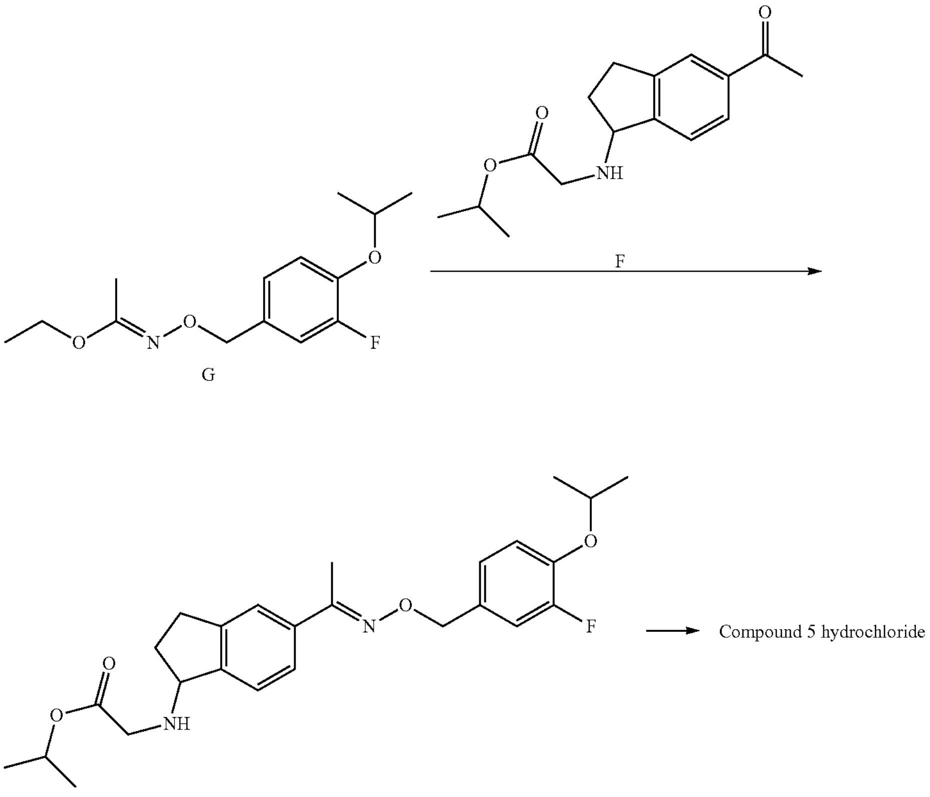

G 5-1

Step 1: Synthesis of Compound 5-1

Intermediate G (1.00 g, 3.71 mmol) was dissolved in methanol (60 mL), and hydrochloric acid/ethyl acetate (15.47 mL, 61.89 mmol) was added. The mixture was stirred at 25° C. for 0.5 hours. Intermediate F (0.68 g, 2.48 mmol) and triethylamine (5.01 g, 49.51 mmol) were added, and the reaction solution was heated to 60° C. and stirred for 12 hours. The reaction solution was concentrated under reduced pressure. The residue was purified by column chromatography on silica gel (1/1, petroleum ether/ethyl acetate) to give compound 5-1.

$^1$H NMR (400 MHz, DMSO-$d_6$) δ=7.52-7.44 (m, 2H), 7.33 (d, J=7.8 Hz, 1H), 7.17-7.12 (m, 3H), 5.10 (s, 2H), 4.94 (s, J=6.2 Hz, 1H), 4.65-4.55 (m, 2H), 4.48 (s, 2H), 4.16 (t, J=6.4 Hz, 1H), 2.98-2.87 (m, 1H), 2.73 (t, J=7.6, 15.6 Hz, 1H), 2.30-2.22 (m, 1H), 2.20 (s, 3H), 1.81-1.72 (m, 1H), 1.28-1.27 (m, 6H), 1.19 (d, J=8.0 Hz, 6H).

Step 2: Synthesis of Compound 5 Hydrochloride

Compound 5-1 (0.24 g, 0.53 mmol) was dissolved in tetrahydrofuran (8.5 mL) and water (2 mL), and sodium hydroxide (1.00 g, 24.91 mmol) was added. The reaction solution was heated to 60° C. and stirred for 2 hours. 1 M dilute hydrochloric acid (5 mL) was added dropwise to the reaction solution to adjust the pH of the reaction solution to 4. The mixture was extracted with ethyl acetate (10 mL×2), washed with saturated brine (10 mL×2), dried over anhydrous sodium sulfate, and filtered. The filtrate was concentrated under reduced pressure. The crude product was separated by preparative high performance liquid chromatography (Column: Venusil ASB Phenyl 150×30 mm×5 m; Mobile phase: 0.05% hydrochloric acid in water-acetonitrile; Gradient: 35%-65% acetonitrile, 9 min) to give compound 5 hydrochloride.

MS-ESI calculated [M+Na]$^+$ 437, found 437.

$^1$H NMR (400 MHz, DMSO-$d_6$) δ=7.70 (d, J=7.8 Hz, 1H), 7.63-7.51 (m, 2H), 7.23 (d, J=12 Hz, 1H), 7.18-7.12 (m, 2H), 5.11 (s, 2H), 4.82-4.74 (m, 1H), 4.68-4.55 (m, 1H), 3.83-3.69 (m, 2H), 3.20-3.08 (m, 1H), 2.91-2.81 (m, 1H), 2.47-2.36 (m, 1H), 2.28-2.22 (m, 1H), 2.21 (s, 3H), 1.27 (d, J=8.0 Hz, 6H).

Example 6

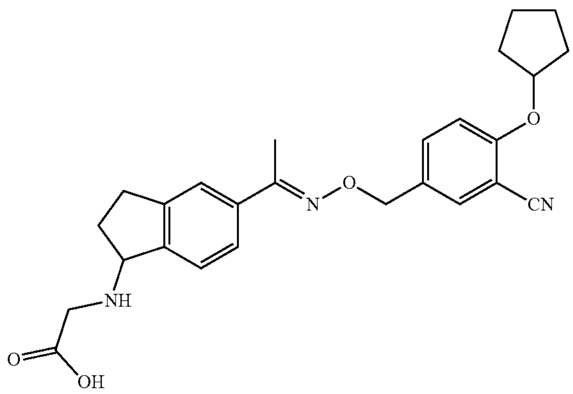

Synthetic Route:

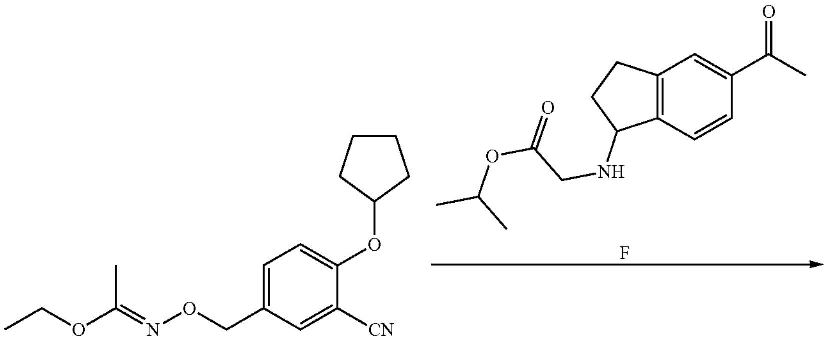

H

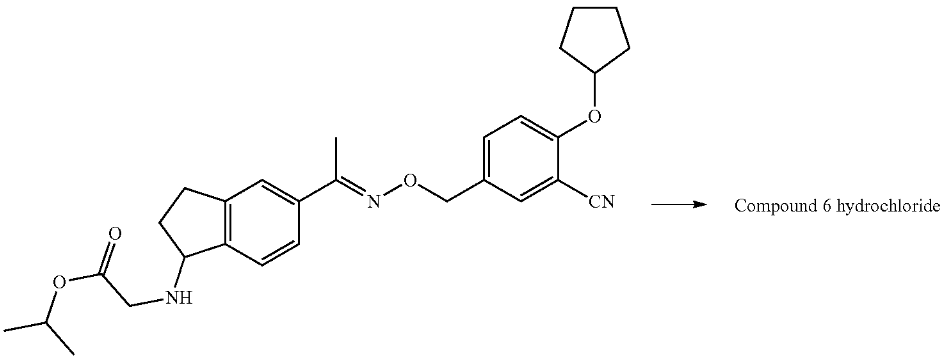

6-1

Step 1: Synthesis of Compound 6-1

Intermediate H (870.00 mg, 2.88 mmol) was dissolved in methanol (50 mL), and then hydrochloric acid/ethyl acetate (11.99 mL, 47.95 mmol) was added. The mixture was stirred at 25° C. for 0.5 hours. Intermediate F (0.53 g, 1.92 mmol) and triethylamine (3.88 g, 38.36 mmol) were added, and the reaction solution was stirred at 60° C. for 12 hours. The mixture was concentrated under reduced pressure. The residue was purified by column chromatography on silica gel (1/1, petroleum ether/ethyl acetate) to give compound 6-1.

MS-ESI calculated $[M+H]^+$ 490, found 490.

$^1$H NMR (400 MHz, DMSO-$d_6$) δ=7.76-7.63 (m, 2H), 7.51-7.40 (m, 2H), 7.33 (d, J=7.8 Hz, 1H), 7.25 (d, J=8.8 Hz, 1H), 5.12 (s, 2H), 5.03-4.92 (m, 2H), 4.16 (t, J=6.4 Hz, 1H), 4.03 (q, J=8.0 Hz, 1H), 2.98-2.87 (m, 1H), 2.77-2.68 (m, 1H), 2.29-2.21 (m, 1H), 2.19 (s, 3H), 2.01-1.88 (m, 4H), 1.78-1.69 (m, 5H), 1.64-1.57 (m, 2H), 1.20 (d, J=4.0 Hz, 6H).

Step 2: Synthesis of Compound 6 Hydrochloride

Compound 6-1 was dissolved in tetrahydrofuran (2 mL) and water (0.4 mL), and sodium hydroxide (193.53 mg, 4.84 mmol) was added. The reaction solution was stirred at 60° C. for 2 hours. 1 M dilute hydrochloric acid (1 mL) was added dropwise until the pH of the reaction solution was 4. The mixture was filtered, and the filter cake was washed with methanol (5 mL×3), and dried in vacuum to give compound 6 hydrochloride.

MS-ESI calculated $[M+H]^+$ 448, found 448.

$^1$H NMR (400 MHz, $CD_3OD$) δ=7.67-7.60 (m, 4H), 7.58-7.53 (m, 1H), 7.16 (d, J=8.8 Hz, 1H), 5.15 (s, 2H), 5.01-4.94 (m, 2H), 4.58 (s, 3H), 3.50 (d, J=2.8 Hz, 2H), 3.24-3.15 (m, 1H), 3.05-2.96 (m, 1H), 2.63-2.52 (m, 1H), 2.26 (s, 3H), 2.06-1.93 (m, 3H), 1.91-1.80 (m, 5H).

Example 7

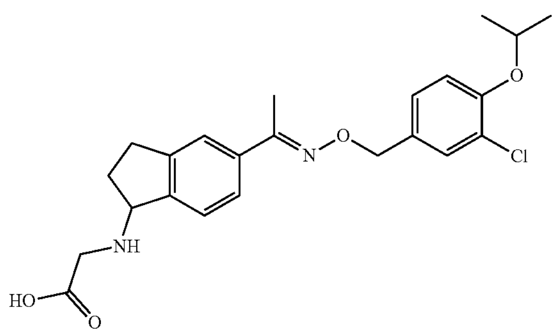

7

Synthetic Route:

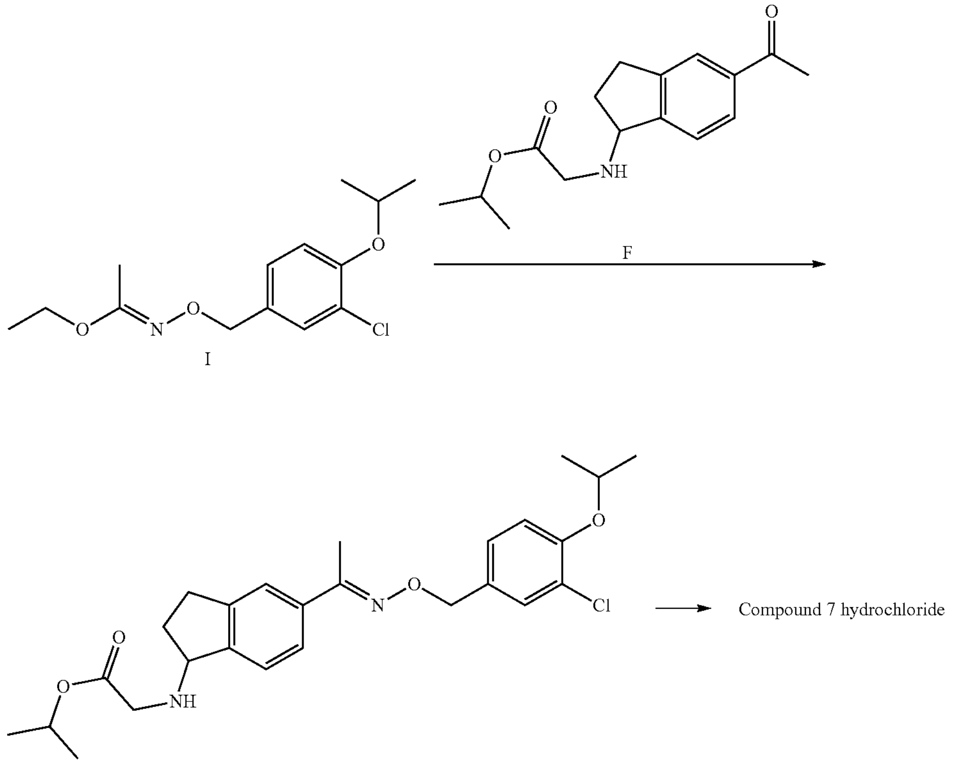

I 7-1

Step 1: Synthesis of Compound 7-1

Intermediate I (0.15 g, 0.53 mmol) was dissolved in methanol (8.5 mL), and hydrochloric acid/ethyl acetate (2.19 mL, 8.75 mmol) was added. The mixture was stirred at 25° C. for 0.5 hours. Intermediate F (0.096 g, 0.35 mmol) and triethylamine (0.71 g, 7.00 mmol) were added, and the reaction solution was heated to 60° C. and stirred for 12 hours. The reaction solution was concentrated under reduced pressure, and the residue was purified by column chromatography on silica gel (1/1, petroleum ether/ethyl acetate) to give compound 7-1.

$^1$H NMR (400 MHz, DMSO-$d_6$) δ=7.50-7.43 (m, 2H), 7.37-7.27 (m, 2H), 7.24-7.19 (m, 1H), 7.16-7.09 (m, 1H), 5.09 (s, 1H), 5.00-4.87 (m, 1H), 4.67-4.60 (m, 1H), 4.47 (s, 1H), 4.19-4.08 (m, 1H), 4.03 (q, J=8.0 Hz, 1H), 3.17 (d, J=4.0 Hz, 1H), 3.06 (s, 1H), 2.98-2.85 (m, 1H), 2.80-2.65 (m, 1H), 2.04-1.94 (m, 2H), 1.28 (d, J=8.0 Hz, 6H).

Step 2: Synthesis of Compound 7 Hydrochloride

Compound 7-1 (0.08 mg, 0.17 mmol) was dissolved in tetrahydrofuran (3 mL) and water (0.6 mL), and sodium hydroxide (0.32 g, 8.00 mmol) was added. The reaction solution was stirred at 60° C. for 2 hours. 1 M dilute hydrochloric acid (1.5 mL) was added dropwise to the reaction solution to adjust the pH of the reaction solution to 4. The mixture was filtered, and the filter cake was washed with methanol (5 mL×3). The filter cake was collected, and dried under vacuum to give compound 7 hydrochloride.

$^1$H NMR (400 MHz, $CD_3OD$) δ=7.69-7.52 (m, 3H), 7.45-7.35 (m, 1H), 7.32-7.24 (m, 1H), 7.10-7.00 (m, 1H), 5.16-5.06 (m, 2H), 4.66-4.55 (m, 4H), 3.55-3.46 (m, 2H), 3.05-2.92 (m, 1H), 2.60-2.50 (m, 1H), 2.25 (s, 3H), 1.35-1.32 (m, 6H).

Example 8

8

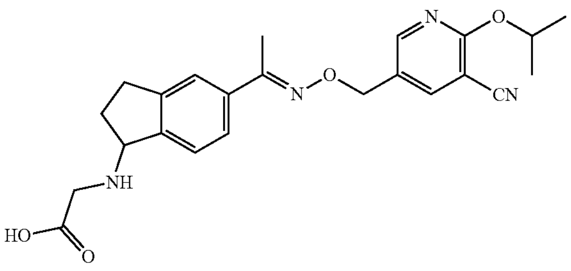

Synthetic Route:

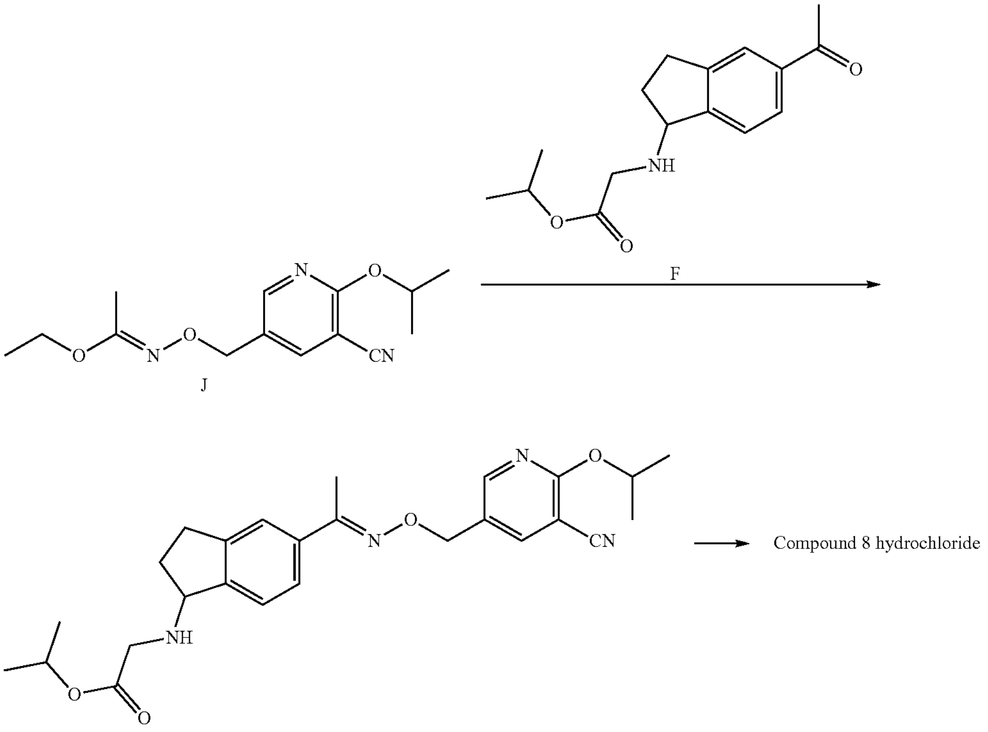

F

J 8-1

Compound 8 hydrochloride

Step 1: Synthesis of Compound 8-1

Under nitrogen atmosphere, to a solution of intermediate J (0.15 g, 0.54 mmol) in methanol (10 mL) was added hydrochloric acid/ethyl acetate (2.70 mL, 10.82 mmol), and the reaction solution was stirred at 20° C. for 0.5 hours. Triethylamine (0.99 g, 9.74 mmol) was added dropwise to the reaction solution, and intermediate F (0.12 g, 0.43 mmol) was added. The reaction solution was stirred at 60° C. for 14 hours. The mixture was concentrated under reduced pressure, and the residue was purified by column chromatography on silica gel (1/1, petroleum ether/ethyl acetate) to give compound 8-1.

MS-ESI calculated $[M+H]^+$ 465, found 465.

Step 2: Synthesis of Compound 8 Hydrochloride

Under nitrogen atmosphere, compound 8-1 (0.15 g, 0.32 mmol) was dissolved in tetrahydrofuran (10 mL) and water (2 mL), and sodium hydroxide (1.00 g, 25.00 mmol) was added. The reaction solution was stirred at 60° C. for 2 hours. The reaction solution was concentrated under reduced pressure. The crude product was separated by high performance liquid chromatography (Column: Phenomenex Luna C18 150×30 mm×5 m; Mobile phase: 0.05% hydrochloric acid in water-acetonitrile; Gradient: 40%-70% acetonitrile, 9 min) to give compound 8 hydrochloride.

$^1$H NMR (400 MHz, $CD_3OD$) δ=8.43 (d, J=4.0 Hz, 1H), 8.10 (d, J=2.0 Hz, 1H), 7.68-7.63 (m, 2H), 7.59 (s, 1H), 5.50-5.40 (m, 1H), 5.18 (s, 2H), 3.95 (s, 2H), 3.28-3.18 (m, 1H), 3.07-2.97 (m, 1H), 2.68-2.55 (m, 1H), 2.31-2.23 (m, 5H), 1.39 (d, J=8.0 Hz, 6H).

Example 9

9

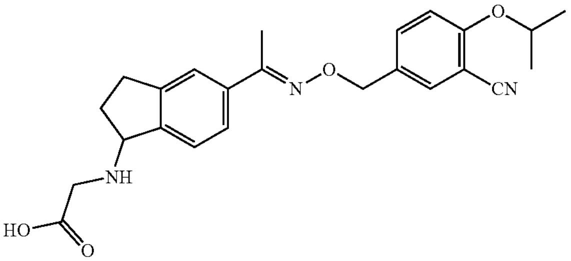

Synthetic Route:

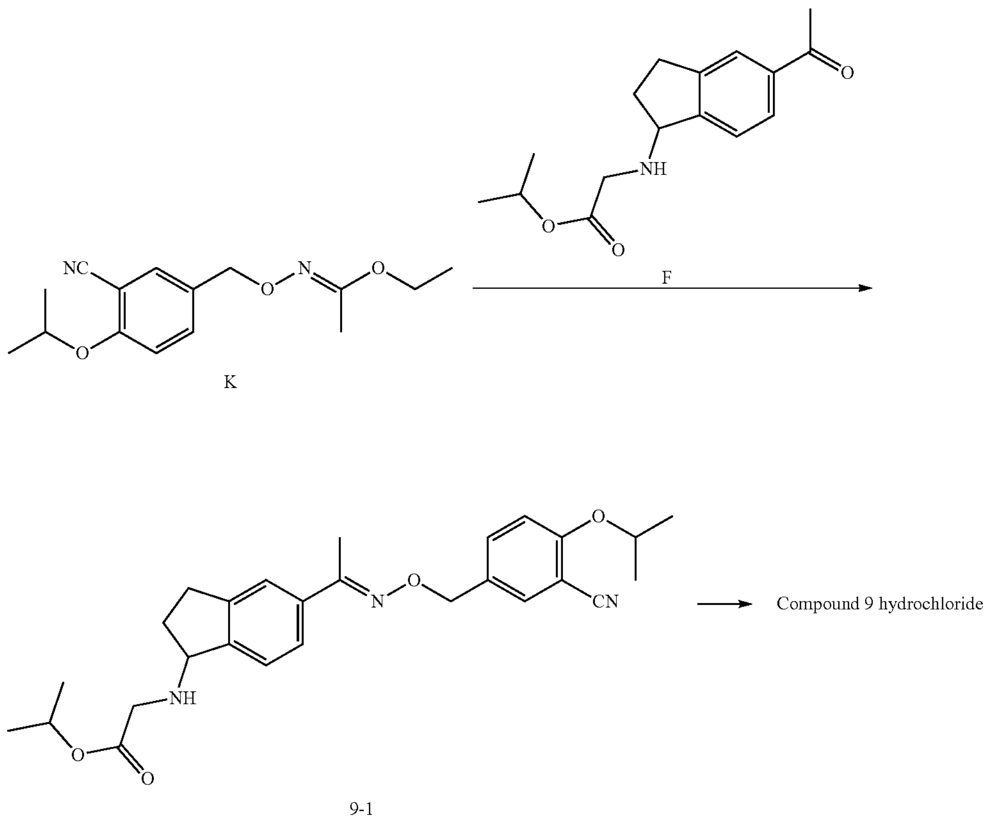

Step 1: Synthesis of Compound 9-1

Under nitrogen atmosphere, to a solution of intermediate K (0.20 g, 0.72 mmol) in methanol (10 mL) was added hydrochloric acid/ethyl acetate (3.62 mL, 3.62 mL), and the reaction solution was reacted at 20° C. for 0.5 hours. Triethylamine (1.32 g, 13.03 mmol) was added dropwise to the reaction solution, and intermediate F (0.16 g, 0.58 mmol) was added. The reaction solution was reacted at 60° C. for 14 hours. The mixture was concentrated under reduced pressure, and the residue was purified by column chromatography on silica gel (1/1, petroleum ether/ethyl acetate) to give compound 9-1.

MS-ESI calculated $[M+H]^+$ 464, found 464.

Step 2: Synthesis of Compound 9 Hydrochloride

Under nitrogen atmosphere, compound 9-1 (0.05 g, 0.11 mmol) was dissolved in tetrahydrofuran (5 mL) and water (1 mL), and sodium hydroxide (0.25 g, 6.26 mmol) was added. The mixture was reacted at 60° C. for 2 hours. The reaction solution was concentrated, and the resulting crude product was separated by high performance liquid chromatography (Column: Phenomenex Luna C18 150×30 mm×5 m; Mobile phase: 0.05% hydrochloric acid in water-acetonitrile; Gradient: 35%-65% acetonitrile, 9 min) to give compound 9 hydrochloride.

MS-ESI calculated $[M+H]^+$ 422, found 422.

$^1H$ NMR (400 MHz, $CD_3OD$) δ=7.68-7.65 (m, 2H), 7.64-7.63 (m, 2H), 7.57 (d, J=8.0 Hz, 1H), 7.17 (d, J=8.0 Hz, 1H), 5.15 (s, 2H), 4.80-4.73 (m, 1H), 3.92 (s, 2H), 3.25-3.18 (m, 2H), 3.06-2.99 (m, 1H), 2.65-2.55 (m, 1H), 2.33-2.23 (m, 4H), 1.38 (d, J=6.0 Hz, 6H).

Example 10

10

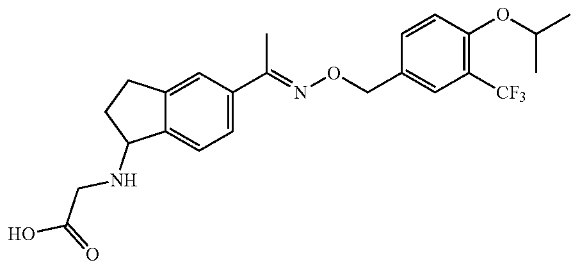

Synthetic Route:

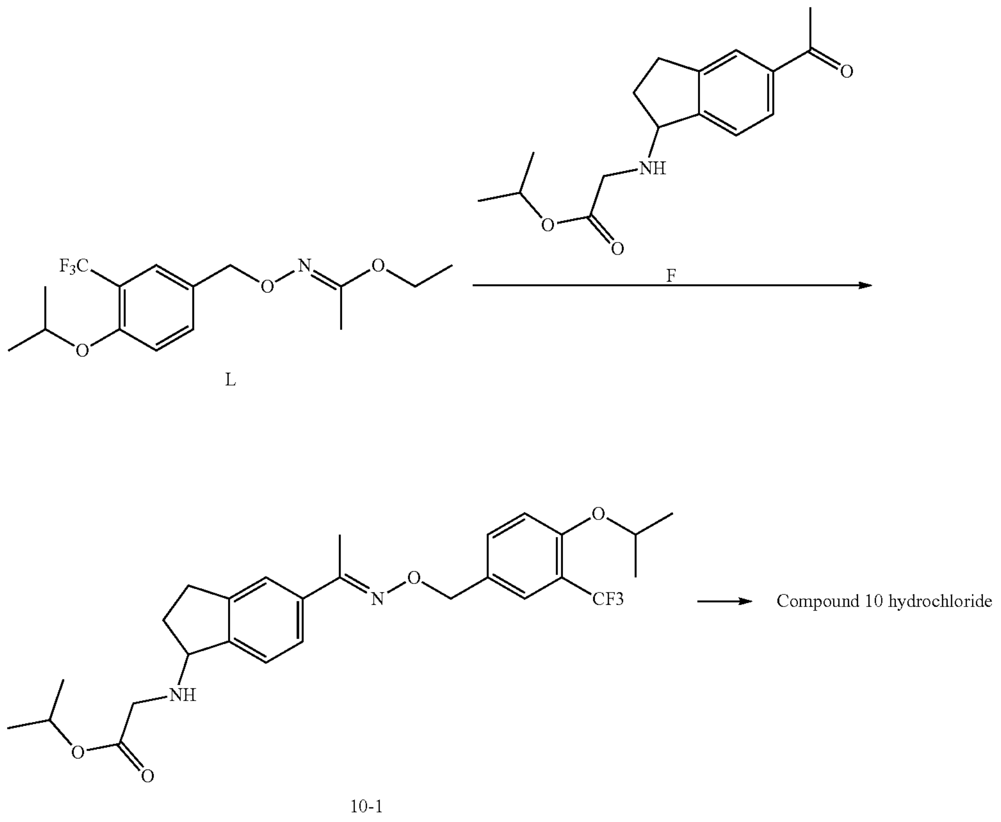

Step 1: Synthesis of Compound 10-1

Under nitrogen atmosphere, to a solution of intermediate L (0.10 g, 0.31 mmol) in methanol (8 mL) was added hydrochloric acid/ethyl acetate (2 mL, 8 mmol), and the reaction solution was reacted at 25° C. for 0.5 hours. Triethylamine (0.57 g, 5.64 mmol) was added dropwise to the reaction solution, and intermediate F (0.07 g, 0.25 mmol) was added. The reaction solution was reacted at 60° C. for 14 hours. The reaction solution was directly concentrated under reduced pressure, and the residue was purified by column chromatography on silica gel (1/1, petroleum ether/ethyl acetate) to give compound 10-1.

Step 2: Synthesis of Compound 10 Hydrochloride

Under nitrogen atmosphere, intermediate 10-1 (0.10 g, 0.20 mmol) was dissolved in tetrahydrofuran (10 mL) and water (2 mL), and sodium hydroxide (0.61 g, 15.28 mmol) was added. The reaction solution was reacted at 60° C. for 2 hours. The reaction solution was concentrated, and the resulting crude product was separated by high performance liquid chromatography (Column: Phenomenex Luna C18 150×30 mm×5 m; Mobile phase: 0.05% hydrochloric acid in water-acetonitrile; Gradient: 29%-49% acetonitrile, 7 min) to give compound 10 hydrochloride.

MS-ESI calculated $[M+Na]^+$ 487, found 487.

$^1H$ NMR (400 MHz, $CD_3OD$) δ=7.69-7.54 (m, 5H), 7.16 (br d, J=8.0 Hz, 1H), 5.17 (s, 2H), 4.77-4.70 (m, 1H), 3.91 (s, 2H), 3.26-3.19 (m, 2H), 3.03 (s, 1H), 2.62-2.55 (m, 1H), 2.32-2.22 (m, 4H), 1.34 (d, J=8.0 Hz, 6H).

Example 11

11

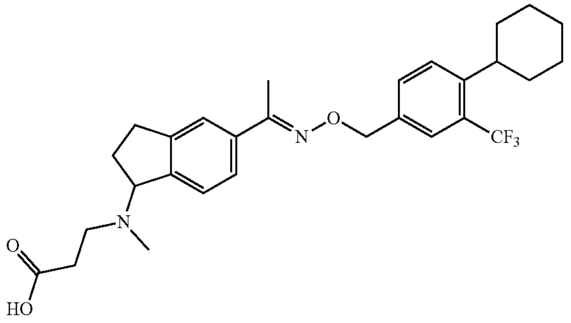

Synthetic Route:

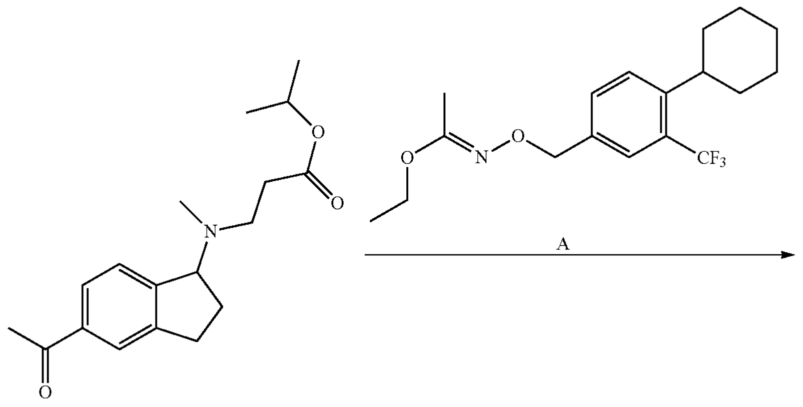

M

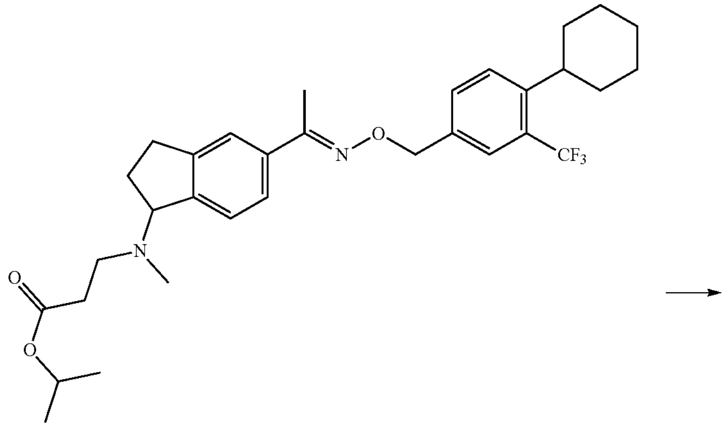

Compound 11 trifluoroacetate 11-1

Step 1: Synthesis of Compound 11-1

Under the protection of nitrogen, to a solution of intermediate A (0.15 g, 0.44 mmol) in methanol (10 mL) was added hydrochloric acid/ethyl acetate (3.01 mL, 12.03 mmol), and the reaction solution was reacted at 20° C. for 0.5 hours. Triethylamine (0.80 g, 7.86 mmol) was added dropwise to the reaction solution, and intermediate M (0.11 g, 0.35 mmol) was added. The reaction solution was reacted at 60° C. for 14 hours. The mixture was concentrated under reduced pressure, and the residue was purified by column chromatography on silica gel (1/1, petroleum ether/ethyl acetate) to give compound 11-1.

MS-ESI calculated $[M+H]^+$ 559, found 559.

Step 2: Synthesis of Compound 11 Trifluoroacetate

Under nitrogen atmosphere, compound 11-1 (0.10 g, 0.18 mmol) was dissolved in tetrahydrofuran (10 mL) and water (2 mL), and sodium hydroxide (0.50 g, 12.50 mmol) was added. The mixture was reacted at 60° C. for 2 hours. After the reaction was completed, the reaction solution was concentrated, and the resulting crude product was separated by high performance liquid chromatography (Column: Boston Green ODS 150×30 mm×5 m; Mobile phase: 0.075% trifluoroacetic acid in water-acetonitrile; Gradient: 40%-70% acetonitrile, 9 min) to give compound 11 trifluoroacetate.

MS-ESI calculated $[M+H]^+$ 517, found 517.

$^1H$ NMR (400 MHz, $CD_3OD$) δ=7.70 (s, 1H), 7.66 (s, 2H), 7.64-7.59 (m, 2H), 7.57-7.53 (m, 1H), 5.25 (s, 2H), 5.16-5.06 (m, 1H), 3.26-3.15 (m, 3H), 3.13-2.98 (m, 1H), 2.95-2.84 (m, 2H), 2.77-2.74 (m, 2H), 2.63-2.41 (m, 2H), 2.29 (s, 3H), 1.94-1.73 (m, 5H), 1.60-1.35 (m, 6H).

Example 12

12

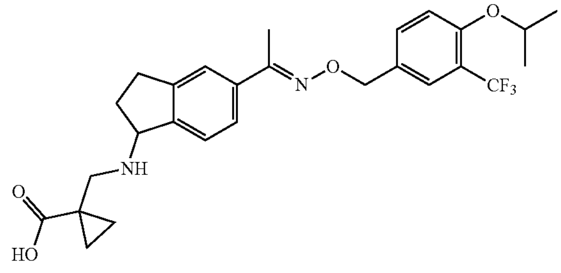

Synthetic Route:

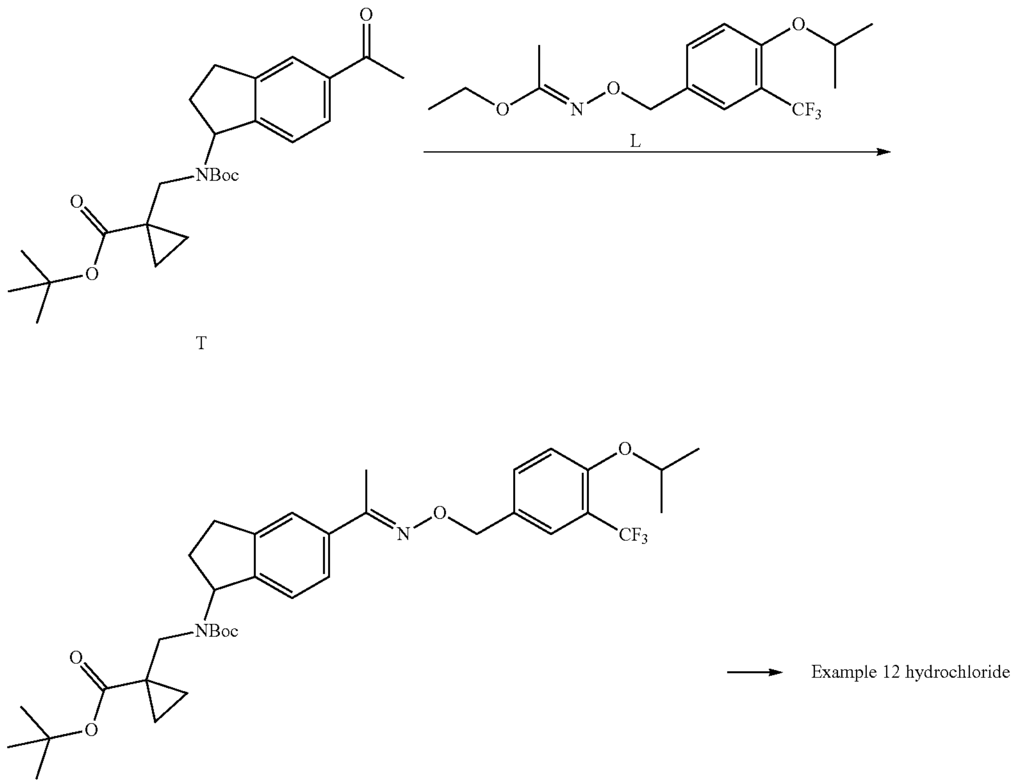

Step 1: Synthesis of Compound 12-1

Intermediate L (149 mg, 466 μmol) was dissolved in methanol (15 mL), and then hydrochloric acid/ethyl acetate (1.46 mL, 4 M) was added dropwise to the reaction solution. The reaction solution was reacted at 20° C. for 0.5 hours. Triethylamine (471 mg, 4.66 mmol) was added dropwise to the reaction solution, and intermediate T (100 mg, 233 μmol) was added. The reaction solution was reacted at 60° C. for 5 hours. The reaction solution was concentrated under reduced pressure to give the crude product of compound 12-1.

MS-ESI calculated $[M-Boc+H]^+$ 561, found 561.

Step 2: Synthesis of Compound 12 Hydrochloride

The crude product of compound 12-1 (175 mg, 265 μmol) was dissolved in ethyl acetate (4 mL), and then hydrochloric acid/ethyl acetate (1.66 mL, 4 M) was added dropwise to the reaction solution. The mixture was reacted at 25° C. for 12 hours. After the reaction was completed, the reaction solution was adjusted to a pH of 6 with 1 M aqueous hydrochloric acid solution, and then concentrated under reduced pressure. The resulting crude product was separated by high performance liquid chromatography (Column: 3_Phenomenex Luna C18 75*30 mm*3 μm; Mobile phase: 0.05% hydrochloric acid in water-acetonitrile; Gradient: 38%-58% acetonitrile, 6.5 min) to give compound 12 hydrochloride.

MS-ESI calculated $[M+H]^+$ 505, found 505.

$^1H$ NMR (400 MHz, $CD_3OD$) δ=7.68-7.55 (m, 5H), 7.21-7.11 (m, 1H), 5.17 (s, 2H), 4.78-4.71 (m, 1H), 3.23-3.14 (m, 3H), 3.08-2.97 (m, 1H), 2.69-2.55 (m, 2H), 2.44-2.21 (m, 4H), 1.41 (br d, J=3.2 Hz, 2H), 1.34 (d, J=6.0 Hz, 6H), 1.13-1.02 (m, 2H).

Example 13

13

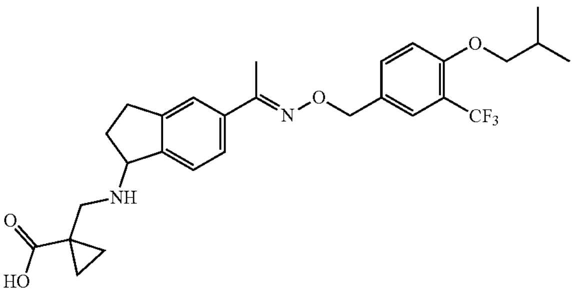

Synthetic Route:

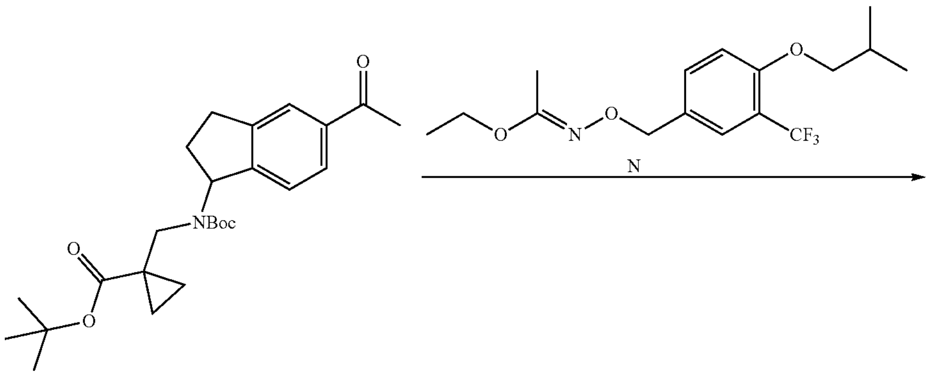

T

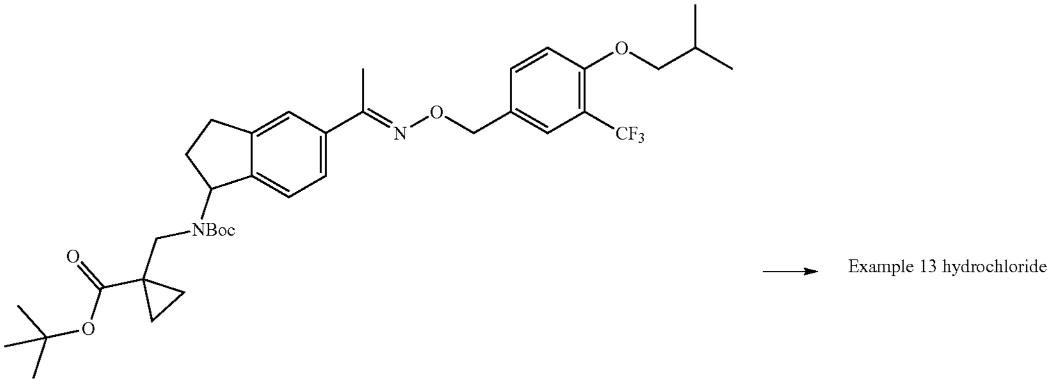

13-1

Step 1: Synthesis of Compound 13-1

Intermediate N (155 mg, 466 μmol) was dissolved in methanol (15 mL), and then hydrochloric acid/ethyl acetate (1.46 mL, 4 M) was added dropwise to the reaction solution. The reaction solution was reacted at 20° C. for 0.5 hours. Triethylamine (471 mg, 4.66 mmol) was added dropwise to the reaction solution, and intermediate T (100 mg, 233 μmol) was added. The reaction solution was reacted at 60° C. for 5 hours. The reaction solution was concentrated under reduced pressure to give the crude product of compound 13-1.

MS-ESI calculated $[M-Boc+H]^+$ 575, found 575.

Step 2: Synthesis of Compound 13 Hydrochloride

The crude product of compound 13-1 (183 mg, 271 μmol) was dissolved in ethyl acetate (4 mL), and then hydrochloric acid/ethyl acetate (1.69 mL, 4 M) was added dropwise to the reaction solution. The mixture was reacted at 25° C. for 12 hours. After the reaction was completed, the reaction solution was adjusted to a pH of 6 with 1 M aqueous hydrochloric acid solution, and then concentrated under reduced pressure. The resulting crude product was separated by high performance liquid chromatography (Column: 3_Phenomenex Luna C18 75*30 mm*3 m; Mobile phase: 0.05% hydrochloric acid in water-acetonitrile; Gradient: 41%-61% acetonitrile, 6.5 min) to give compound 13 hydrochloride.

MS-ESI calculated $[M+H]^+$ 519, found 519.

$^1H$ NMR (400 MHz, $CD_3OD$) δ=7.68-7.56 (m, 5H), 7.12 (d, J=8.4 Hz, 1H), 5.17 (s, 2H), 4.91 (br d, J=4.0 Hz, 2H), 3.86 (d, J=6.0 Hz, 2H), 3.25-3.17 (m, 3H), 3.08-2.97 (m, 1H), 2.64-2.56 (m, 1H), 2.44-2.31 (m, 1H), 2.25 (s, 3H), 2.16-2.05 (m, 1H), 1.41 (d, J=3.4 Hz, 2H), 1.13-1.02 (m, 8H).

Example 14

14

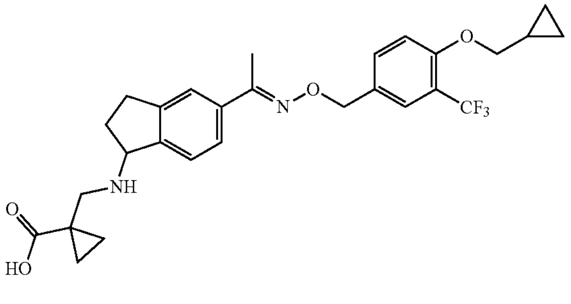

Synthetic Route:

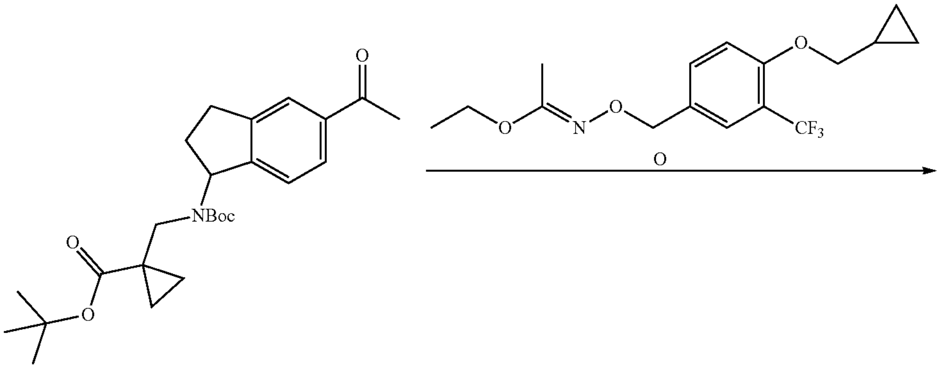

T

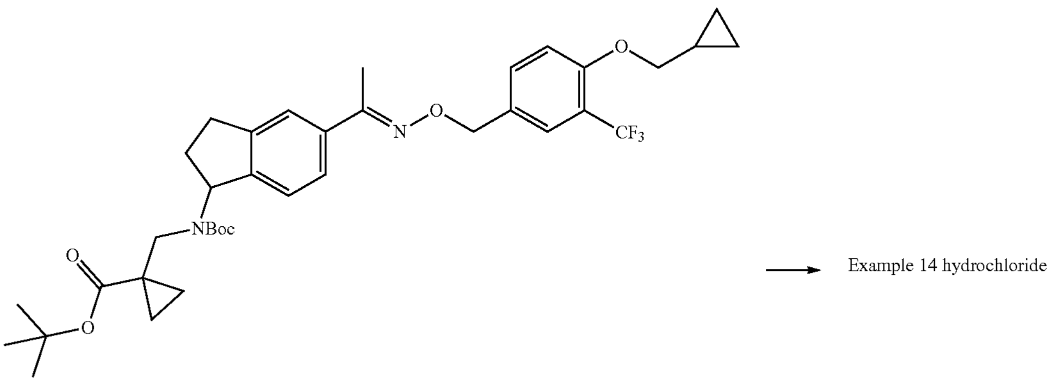

14-1

Step 1: Synthesis of Compound 14-1

Intermediate O (154 mg, 466 μmol) was dissolved in methanol (15 mL), and then hydrochloric acid/ethyl acetate (1.46 mL, 4 M) was added dropwise to the reaction solution. The reaction solution was reacted at 20° C. for 0.5 hours. Triethylamine (471 mg, 4.66 mmol) was added dropwise to the reaction solution, and intermediate T (100 mg, 233 μmol) was added. The reaction solution was reacted at 60° C. for 5 hours. The reaction solution was concentrated under reduced pressure to give the crude product of compound 14-1.

MS-ESI calculated $[M-Boc+H]^+$ 573, found 573.

Step 2: Synthesis of Compound 14 Hydrochloride

The crude product of compound 14-1 (169 mg, 251 μmol) was dissolved in ethyl acetate (4 mL), and then hydrochloric acid/ethyl acetate (1.57 mL, 4 M) was added dropwise to the reaction solution. The mixture was reacted at 25° C. for 12 hours. After the reaction was completed, the reaction solution was adjusted to a pH of 6 with 1 M aqueous hydrochloric acid solution, and then concentrated under reduced pressure. The resulting crude product was separated by high performance liquid chromatography (Column: 3_Phenomenex Luna C18 75*30 mm*3 μm; Mobile phase: 0.05% hydrochloric acid in water-acetonitrile; Gradient: 38%-58% acetonitrile, 6.5 min) to give compound 14 hydrochloride.

MS-ESI calculated $[M+H]^+$ 517, found 517.

$^1H$ NMR (400 MHz, $CD_3OD$) δ=7.69-7.54 (m, 5H), 7.12 (d, J=8.4 Hz, 1H), 5.17 (s, 2H), 4.93-4.89 (m, 2H), 3.97 (d, J=6.5 Hz, 2H), 3.19 (s, 2H), 3.08-2.97 (m, 1H), 2.65-2.55 (m, 1H), 2.45-2.32 (m, 1H), 2.25 (s, 3H), 1.46-1.37 (m, 2H), 1.34-1.21 (m, 1H), 1.18-1.00 (m, 2H), 0.65-0.56 (m, 2H), 0.43-0.34 (m, 2H).

Example 15

15

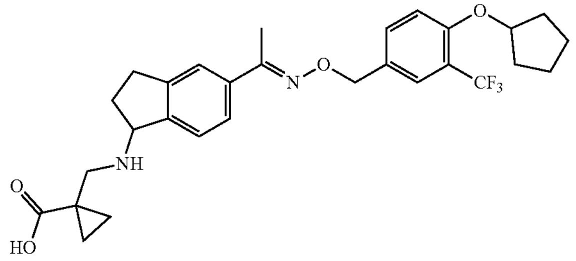

Synthetic Route:

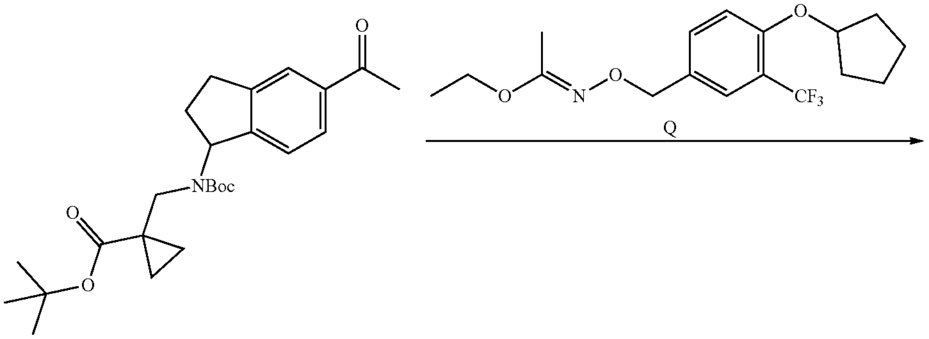

T

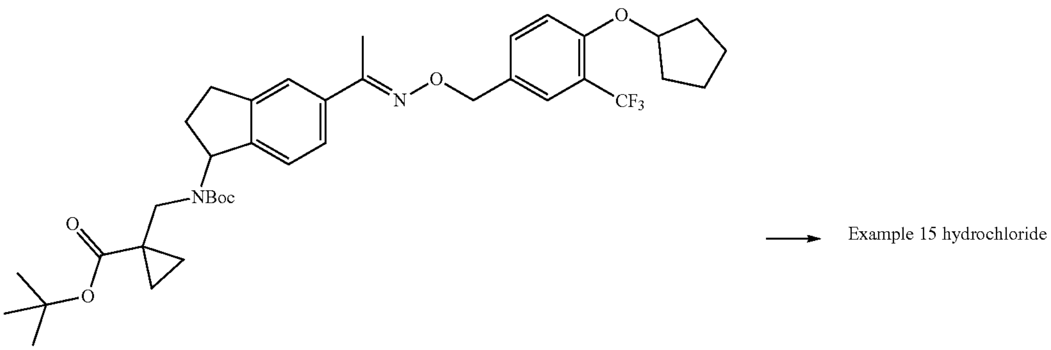

15-1

Step 1: Synthesis of Compound 15-1

Intermediate Q (86.8 mg, 251 μmol) was dissolved in methanol (10 mL), and then hydrochloric acid/ethyl acetate (785 μL, 4 M) was added dropwise to the reaction solution. The reaction solution was reacted at 20° C. for 0.5 hours. Triethylamine (254 mg, 2.51 mmol) was added dropwise to the reaction solution, and intermediate T (54.0 mg, 126 μmol) was added. The reaction solution was reacted at 60° C. for 5 hours. The reaction solution was concentrated under reduced pressure to give the crude product of compound 15-1.

MS-ESI calculated $[M\text{-}Boc+H]^+$ 587, found 587.

Step 2: Synthesis of Compound 15 Hydrochloride

The crude product of compound 15-1 (112 mg, 163 μmol) was dissolved in ethyl acetate (2 mL), and hydrochloric acid/ethyl acetate (1.02 mL, 4 M) was added. The mixture was reacted at 25° C. for 12 hours. After the reaction was completed, the reaction solution was adjusted to a pH of 6 with 1 M aqueous hydrochloric acid solution, and then concentrated under reduced pressure. The resulting crude product was separated by high performance liquid chromatography (Column: 3_Phenomenex Luna C18 75*30 mm*3 m; Mobile phase: 0.05% hydrochloric acid in water-acetonitrile; Gradient: 42%-62% acetonitrile, 6.5 min) to give compound 15 hydrochloride.

MS-ESI calculated $[M+H]^+$ 531, found 531.

$^1H$ NMR (400 MHz, $CD_3OD$) δ=7.77-7.45 (m, 5H), 7.22-7.07 (m, 1H), 5.17 (s, 2H), 4.96 (br s, 2H), 3.19 (br s, 3H), 3.10-2.97 (m, 1H), 2.65-2.56 (m, 1H), 2.46-2.32 (m, 1H), 2.25 (s, 3H), 2.01-1.74 (m, 6H), 1.66 (br s, 2H), 1.51-1.23 (m, 3H), 1.17-0.98 (m, 2H).

Example 16

16

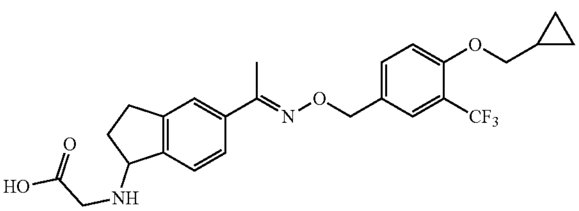

Synthetic Route:

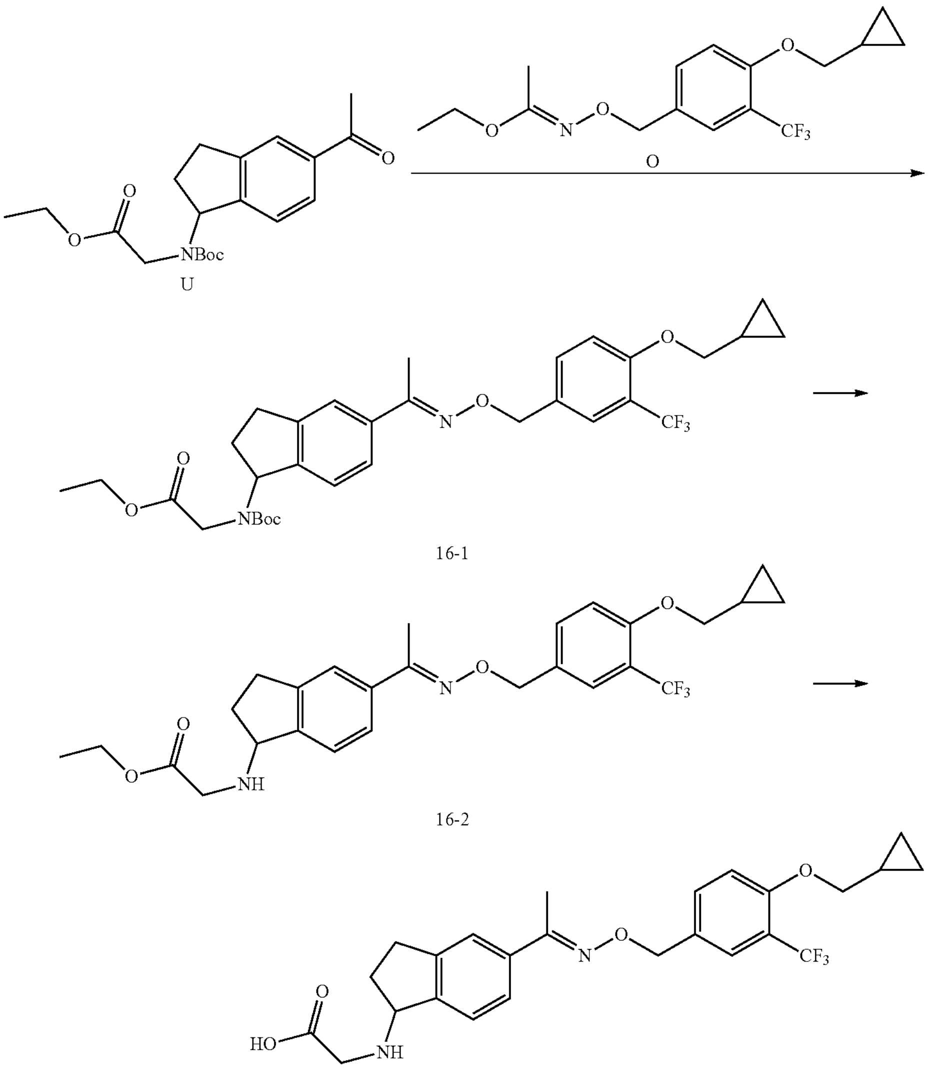

U 16-1

16-2

16

Step 1: Synthesis of Compound 16-1

Intermediate O (155 mg, 415 μmol) was dissolved in methanol (10 mL), and hydrochloric acid/ethyl acetate (1.04 mL, 4 M) was added dropwise. The mixture was stirred at 20° C. for 30 minutes, and then triethylamine (524.94 mg, 5.19 mmol) and intermediate U (75 mg, 208 μmol) were added. The mixture was stirred at 60° C. for 12.5 hours. Water (10 mL) was added to the reaction solution, and the mixture was extracted with ethyl acetate (10 mL×3). The combined organic phase was concentrated under reduced pressure, and the resulting residue was separated by thin-layer chromatography (petroleum ether/ethyl acetate, 3/1, V/V) to give compound 16-1.

MS-ESI calculated $[M+H]^+$ 605, found 605.

Step 2: Synthesis of Compound 16-2

Compound 16-1 (120 mg, 198.5 μmol) was dissolved in hydrochloric acid/ethyl acetate (4 M, 1.85 mL), and the reaction solution was stirred at 15° C. for 1 hour. The reaction solution was concentrated under reduced pressure to give compound 16-2.

MS-ESI calculated $[M+H]^+$ 505, found 505.

Step 3: Synthesis of Compound 16

Compound 16-2 (80 mg, 159 μmol) was dissolved in tetrahydrofuran (0.5 mL), water (0.5 mL) and ethanol (0.25 mL), and sodium hydroxide (12.7 mg, 317 μmol) was added. The mixture was stirred at 55° C. for 4 hours. The reaction solution was adjusted to a pH of 7 with saturated aqueous sodium carbonate solution, and then concentrated under reduced pressure. The resulting crude product was separated by high performance liquid chromatography (Column: Phenomenex luna C18 150*25 mm 10 μm; Mobile phase: 0.225% formic acid in water-acetonitrile; Gradient: 37%-67% acetonitrile, 10 min) to give compound 16.

MS-ESI calculated $[M+Na]^+$ 499, found 499.

$^1H$ NMR (400 MHz, $CD_3OD$) δ=7.65-7.54 (m, 5H), 7.12 (d, J=12 Hz, 1H), 5.17 (s, 2H), 4.83-4.79 (m, 1H), 4.60-4.56

(m, 1H), 3.97 (d, J=8 Hz, 2H), 3.54-3.47 (m, 2H), 3.23-3.13 (m, 1H), 3.03-2.95 (m, 1H), 2.61-2.52 (m, 1H), 2.28-2.21 (m, 4H), 1.34-1.23 (m, 2H), 0.64-0.59 (m, 2H), 0.41-0.37 (m, 2H).

Example 17

17

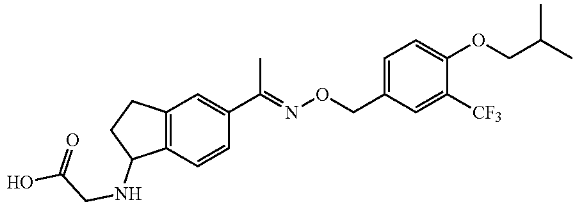

Synthetic Route:

The mixture was stirred at 60° C. for 1 hour. Water (10 mL) was added to the reaction solution. The mixture was extracted with ethyl acetate (10 mL×3). The combined organic phase was concentrated under reduced pressure, and the resulting crude product was separated by thin-layer chromatography (petroleum ether/ethyl acetate, 3/1, V/V) to give compound 17-1.

MS-ESI calculated $[M+H]^+$ 507, found 507.

Step 2: Synthesis of Compound 17

Compound 17-1 (80 mg, 158 μmol) was dissolved in tetrahydrofuran (0.5 mL), water (0.5 mL) and ethanol (0.25 mL), and sodium hydroxide (12.6 mg, 316 μmol) was added. The reaction solution was reacted at 55° C. for 0.5 hours. The reaction solution was adjusted to a pH of 7 with saturated aqueous sodium carbonate solution, and then concentrated under reduced pressure. The resulting crude product was separated by high performance liquid chromatography (Column: Phenomenex lμna C18 150*25 mm*10 m;

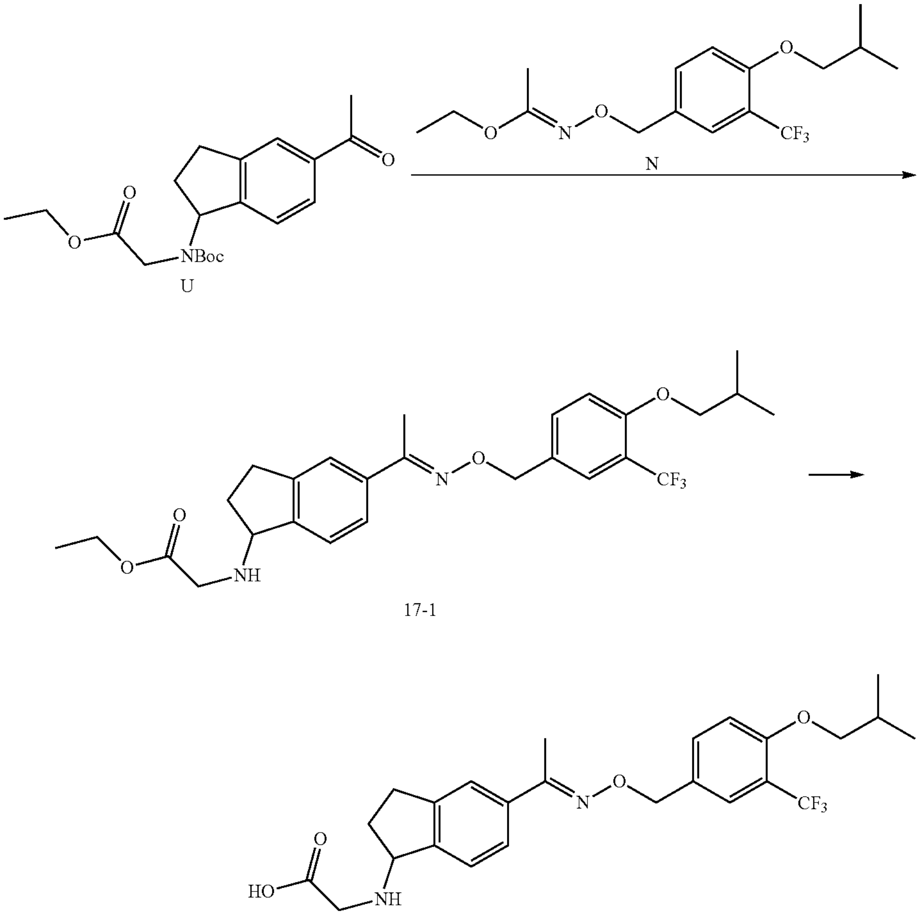

U 17-1

17

Step 1: Synthesis of Compound 17-1

Intermediate N (185 mg, 553 μmol) was dissolved in methanol (5 mL), and hydrochloric acid/ethyl acetate (1.38 mL, 4 M) was added dropwise. The mixture was stirred at 20° C. for 0.5 hours, and then triethylamine (700 mg, 6.92 mmol) and intermediate U (0.100 g, 277 μmol) were added.

Mobile phase: 0.225% formic acid in water-acetonitrile; Gradient: 43%-73% acetonitrile, 10 min) to give compound 17.

MS-ESI calculated $[M+Na]^+$ 501, found 501.

$^1$H NMR (400 MHz, $CD_3OD$) δ=7.68-7.53 (m, 5H), 7.12 (d, J=8 Hz, 1H), 5.17 (s, 2H), 4.83-4.78 (m, 1H), 3.86 (d, J=4 Hz, 2H), 3.53-3.34 (m, 2H), 3.28-3.13 (m, 1H), 3.05-2.93

(m, 1H), 2.61-2.51 (m, 1H), 2.28-2.20 (m, 4H), 2.15-2.01 (m, 1H), 1.40-1.21 (m, 2H), 1.07-1.03 (m, 6H).

Example 18

18

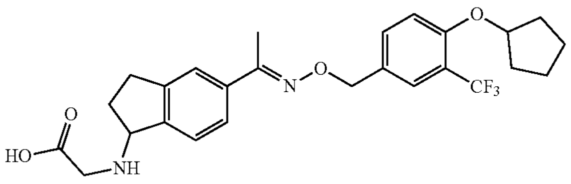

Synthetic Route:

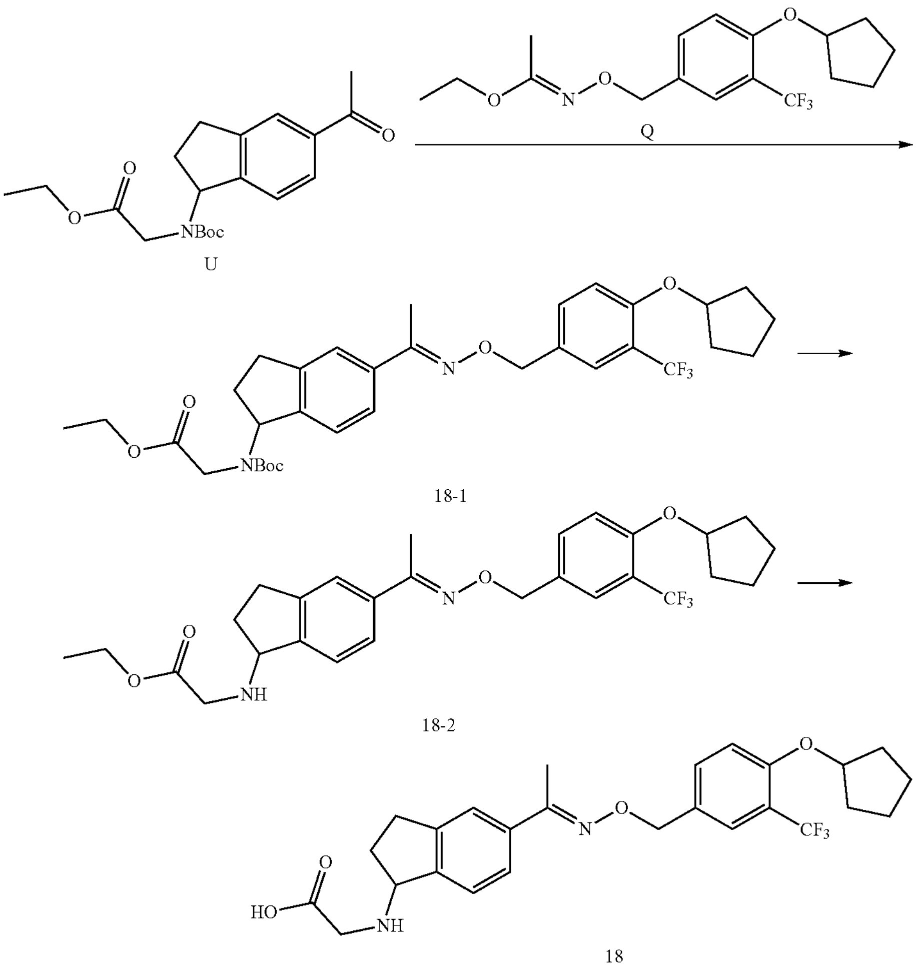

U 18-1

18-2

18

Step 1: Synthesis of Compound 18-1

Intermediate Q (134 mg, 387 μmol) was dissolved in methanol (5 mL), and hydrochloric acid/ethyl acetate (968 μL, 4 M) was added dropwise. The reaction solution was stirred at 20° C. for 30 minutes, and then triethylamine (490 mg, 4.84 mmol) and intermediate U (70.0 mg, 194 μmol) were added. The reaction solution was stirred at 60° C. for 5.5 hours. Water (10 mL) was added to the reaction solution. The mixture was extracted with ethyl acetate (10 mL×3), and the organic phase was concentrated under reduced pressure to give compound 18-1.

MS-ESI calculated $[M+H]^+$ 619, found 619.

Step 2: Synthesis of Compound 18-2

Compound 18-1 (110 mg, 178 μmol) was dissolved in hydrochloric acid/ethyl acetate (4 M, 1.65 mL), and the reaction solution was stirred at 15° C. for 1 hour. The reaction solution was concentrated under reduced pressure to give compound 18-2.

MS-ESI calculated $[M+Na]^+$ 541, found 541.

Step 3: Synthesis of Compound 18

Compound 18-2 (90 mg, 174 μmol) was dissolved in tetrahydrofuran (0.5 mL), water (0.5 mL) and ethanol (0.25 mL), and sodium hydroxide (13.9 mg, 347 μmol) was added. The mixture was stirred at 55° C. for 4 hours. The reaction solution was adjusted to a pH of 7 with saturated aqueous sodium carbonate solution, and then concentrated under reduced pressure. The resulting crude product was separated by high performance liquid chromatography (Column: Unisil 3-10° C.18 Ultra 150*50 mm*3 μm; Mobile phase: 0.225% formic acid in water-acetonitrile; Gradient: 43%-73% acetonitrile, 10 min) to give compound 18.

MS-ESI calculated $[M+Na]^+$ 513, found 513.

$^1H$ NMR (400 MHz, $CD_3OD$) δ=7.69-7.50 (m, 5H), 7.13 (d, J=8 Hz, 1H), 5.21-5.13 (m, 2H), 4.99-4.94 (m, 1H), 4.84-4.80 (m, 1H), 3.58-3.35 (m, 2H), 3.27-3.10 (m, 1H), 3.08-2.89 (m, 1H), 2.63-2.39 (m, 1H), 2.25-2.24 (m, 4H), 1.99-1.77 (m, 6H), 1.71-1.48 (m, 2H), 0.92-0.82 (m, 2H).

Example 19

19

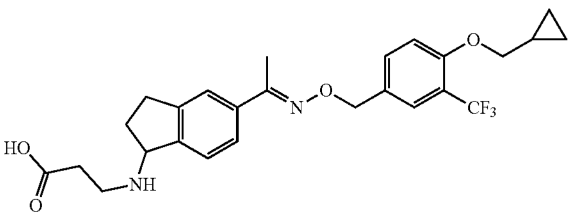

Synthetic Route:

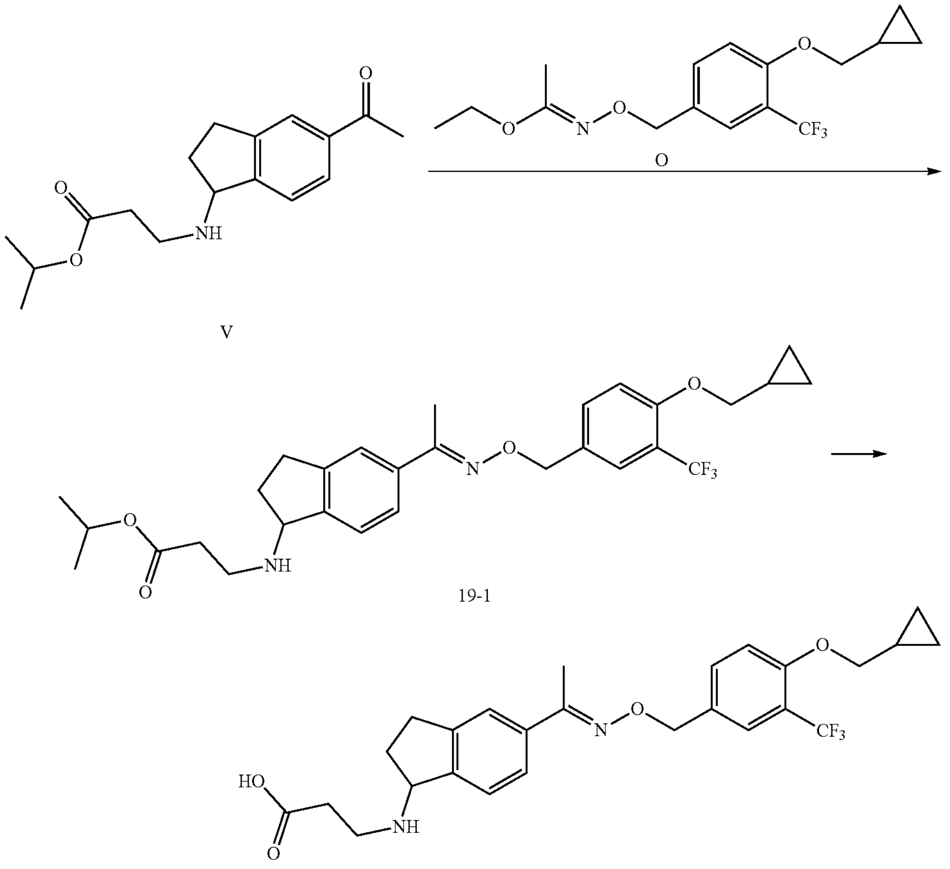

V 19-1

19

Step 1: Synthesis of Compound 19-1

Compound O (1.29 g, 3.46 mmol) was dissolved in methanol (40 mL), and hydrogen chloride/ethyl acetate solution (4 M, 10.8 mL) was added to the reaction solution. The reaction mixture was stirred at 20° C. for 0.5 hours. Triethylamine (34.6 mmol, 4.81 mL) and intermediate V (500 mg, 1.73 μmol) were added successively to the reaction solution. The reaction mixture was stirred at 60° C. for 12 hours. The reaction solution was concentrated under reduced pressure, and the residue was diluted with saturated aqueous sodium bicarbonate solution (100 mL). The mixture was extracted with ethyl acetate (100 mL×2). The combined organic phase was dried over anhydrous sodium sulfate, and filtered. The filtrate was concentrated under reduced pressure, and then purified by column chromatography on silica gel (petroleum ether/ethyl acetate, 5/1~0/1, V/V) to give compound 19-1.

MS-ESI calculated $[M+H]^+$ 533, found 533.

Step 2: Synthesis of Compound 19

Compound 19-1 (380 mg, 713 μmol) was dissolved in tetrahydrofuran (3 mL), ethanol (1.5 mL) and water (3 mL), and sodium hydroxide (57.08 mg, 1.43 mmol) was added to the reaction mixture. The mixture was stirred at 55° C. for 1.5 hours. The reaction solution was adjusted to a pH of 4~5 by adding 4 M hydrochloric acid solution, and then concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 38%-68% acetonitrile, 7 min) to give compound 19.

MS-ESI calculated $[M+H]^+$ 491, found 491.

$^1$H NMR (400 MHz, $CD_3Cl$) δ=9.83-9.43 (m, 2H), 7.66-7.56 (m, 2H), 7.56-7.45 (m, 3H), 6.95 (d, J=8.4 Hz, 1H), 5.15 (s, 2H), 4.74 (br s, 1H), 3.93 (d, J=6.4 Hz, 2H), 3.24-2.83 (m, 4H), 2.65-2.26 (m, 4H), 2.20 (s, 3H), 1.35-1.22 (m, 1H), 0.70-0.57 (m, 2H), 0.46-0.33 (m, 2H).

Example 20

20

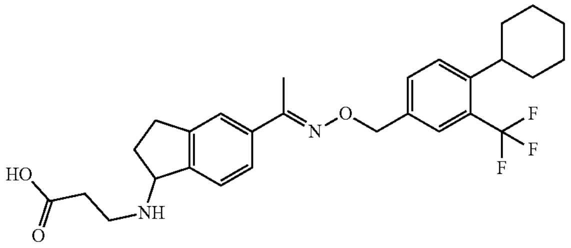

Synthetic Route:

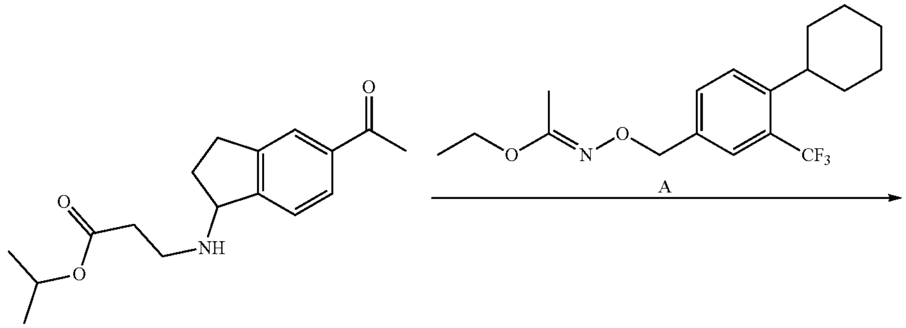

V

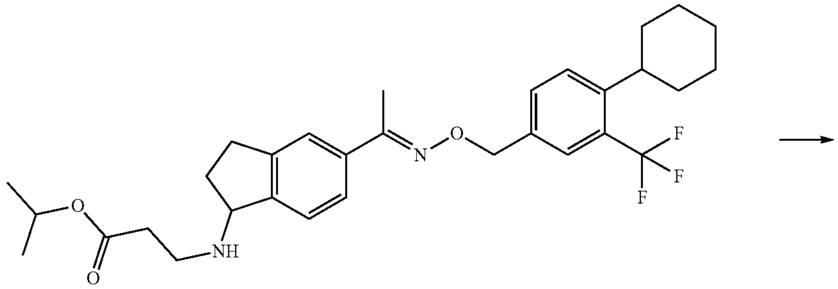

20-1

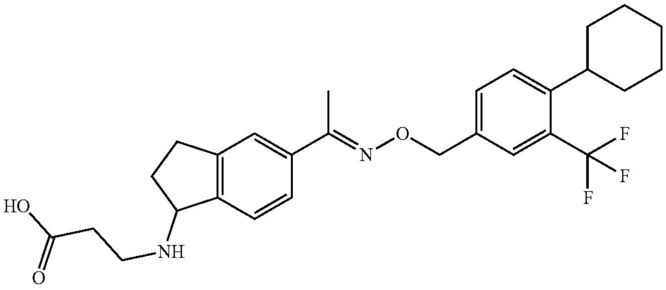

20

Step 1: Synthesis of Compound 20-1

Intermediate A (712 mg, 2.07 mmol) was dissolved in methanol (10 mL), and a solution of hydrogen chloride in ethyl acetate (4 M, 6.48 mL) was added to the reaction solution. The reaction mixture was stirred at 20° C. for 0.5 hours. Then triethylamine (20.7 mmol, 2.89 mL) and intermediate V (300 mg, 1.04 μmol) were added successively to the reaction solution. The reaction mixture was stirred at 60° C. for 12 hours. The reaction solution was concentrated under reduced pressure, and the residue was diluted with saturated aqueous sodium bicarbonate solution (100 mL). The mixture was extracted with ethyl acetate (100 mL×2). The combined organic phase was dried over anhydrous sodium sulfate, and filtered. The filtrate was concentrated under reduced pressure. The resulting crude product was separated by thin-layer chromatography (dichloromethane/methanol, 20/1, V/V) to give compound 20-1.

MS-ESI calculated $[M+H]^+$ 545, found 545.

Step 2: Synthesis of Compound 20

Compound 20-1 (320 mg, 588 μmol) was dissolved in tetrahydrofuran (2 mL), ethanol (1 mL) and water (2 mL), and sodium hydroxide (47.0 mg, 1.18 mmol) was added to the reaction mixture. The mixture was stirred at 55° C. for 1.5 hours. The reaction solution was adjusted to a pH of 5~6 by adding 1 M hydrochloric acid solution, and then extracted with ethyl acetate (100 mL×2). The combined organic phase was dried over anhydrous sodium sulfate, and filtered. The filtrate was concentrated under reduced pressure, and the resulting crude product was separated by high performance liquid chromatography (Column: Phenomenex Gemini-NX C18 75×30 mm×3 m; Mobile phase: 0.225% formic acid in water-acetonitrile; Gradient: 38%-68% acetonitrile, 7 min) to give compound 20.

MS-ESI calculated $[M+H]^+$ 503, found 503.

$^1H$ NMR (400 MHz, $CD_3Cl$) δ=7.66-7.57 (m, 2H), 7.55-7.46 (m, 3H), 7.45-7.42 (m, 1H), 5.20 (s, 2H), 4.74 (br s, 1H), 3.21-2.83 (m, 5H), 2.65-2.26 (m, 4H), 2.22 (s, 3H), 1.88-1.73 (m, 5H), 1.53-1.20 (m, 6H).

Example 21

21

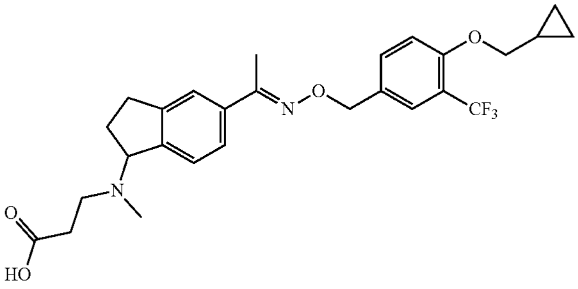

Synthetic Route:

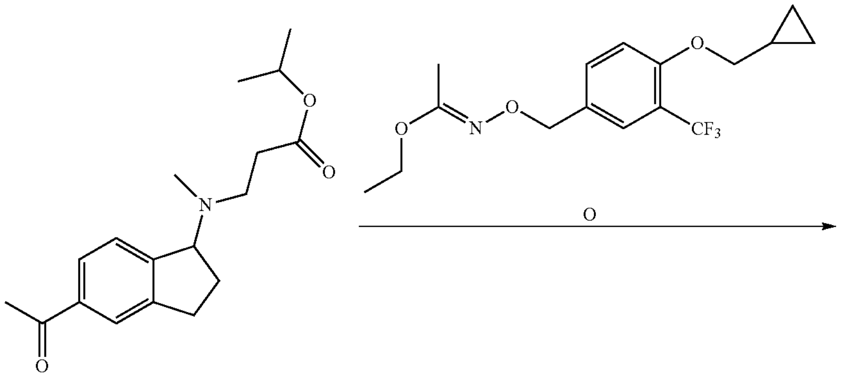

M

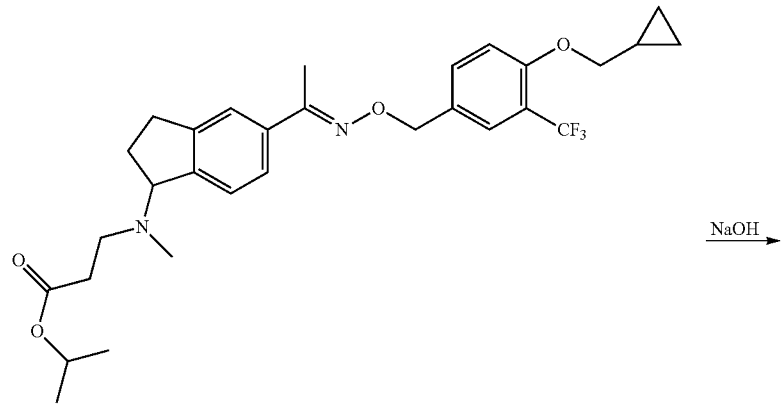

21-1

-continued

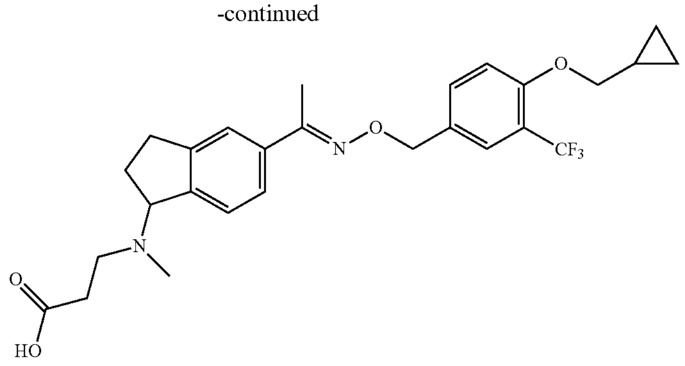

21

Step 1: Synthesis of Compound 21-1

To a solution of intermediate O (118 mg, 389 μmol) in methanol (5 mL) was added hydrochloric acid/ethyl acetate (4 M, 2.43 mL, 9.72 mmol), and the reaction solution was reacted at 20° C. for 0.5 hours. Triethylamine (787 mg, 7.78 mmol) was added dropwise to the reaction solution, and intermediate M (118 mg, 389 μmol) was added. The reaction solution was reacted at 60° C. for 3 hours. The reaction solution was concentrated under reduced pressure. The residue was diluted with 20 mL of water, and extracted with ethyl acetate (10 mL×3). The organic phases were combined, washed with saturated brine (20 mL×1), dried over anhydrous sodium sulfate, and filtered. The filtrate was concentrated under reduced pressure, and the resulting crude product was separated by thin-layer chromatography on silica gel (dichloromethane/methanol, 20/1, V/V) to give compound 21-1.

MS-ESI calculated $[M+H]^+$ 547, found 547.

Step 2: Synthesis of Compound 21

Compound 21-1 (104 mg, 190 μmol) was dissolved in a mixed solution of tetrahydrofuran (2 mL), ethanol (1 mL) and water (2 mL), and sodium hydroxide (15.2 mg, 381 mol) was added. The mixture was reacted at 50° C. for 1 hour. After the reaction was completed, the reaction solution was concentrated, and diluted with 5 mL of water. The mixture was adjusted to a pH of 6 with 1 M hydrochloric acid in water, and concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 30%-60% acetonitrile, 7 min) to give compound 21.

MS-ESI calculated $[M+H]^+$ 505, found 505.

$^1H$ NMR (400 MHz, $CD_3OD$) δ=7.74-7.53 (m, 5H), 7.19-7.11 (m, 1H), 5.19 (s, 2H), 5.13-5.07 (m, 1H), 3.99 (d, J=6.8 Hz, 2H), 3.28-2.99 (m, 4H), 2.69 (s, 3H), 2.65-2.37 (m, 4H), 2.27 (s, 3H), 1.40-1.17 (m, 1H), 0.68-0.57 (m, 2H), 0.44-0.38 (m, 2H).

Example 22

22

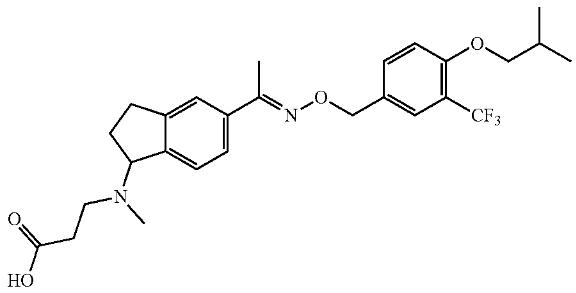

Synthetic Route:

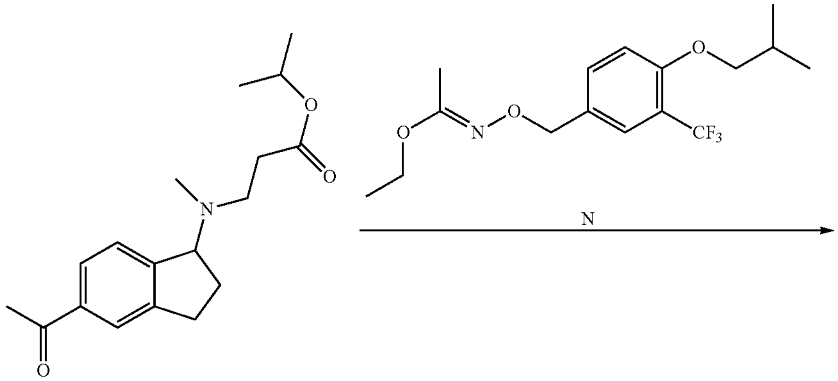

M

-continued

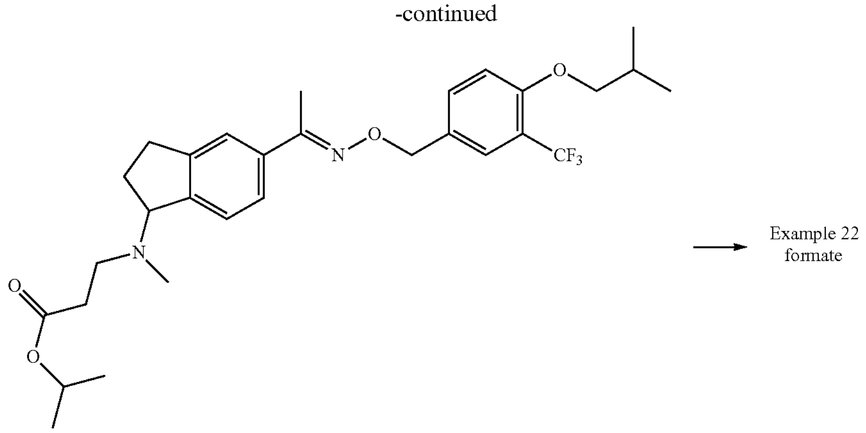

22-1

Step 1: Synthesis of Compound 22-1

To a solution of intermediate N (165 mg, 494 μmol) in methanol (5 mL) was added hydrochloric acid/ethyl acetate (4 M, 1.24 mL, 4.94 mmol), and the reaction solution was reacted at 20° C. for 0.5 hours. Triethylamine (400 mg, 3.96 mmol) was added dropwise to the reaction solution, and intermediate M (150 mg, 494 μmol) was added. The reaction solution was reacted at 60° C. for 9 hours. The reaction solution was concentrated under reduced pressure. The residue was diluted with 20 mL of water, and extracted with ethyl acetate (10 mL×3). The organic phases were combined, washed with saturated brine (20 mL×1), dried over anhydrous sodium sulfate, and filtered. The filtrate was concentrated under reduced pressure, and the resulting crude product was separated by silica gel thin-layer chromatography (dichloromethane/methanol, 20/1, V/V) to give compound 22-1.

MS-ESI calculated $[M+H]^+$ 549, found 549.

Step 2: Synthesis of Compound 22 Formate

Compound 22-1 (88 mg, 160 μmol) was dissolved in a mixed solution of tetrahydrofuran (2 mL), ethanol (1 mL) and water (2 mL), and sodium hydroxide (12.8 mg, 321 mol) was added. The mixture was reacted at 50° C. for 3 hours. After the reaction was completed, the reaction solution was concentrated, and diluted with 5 mL of water. The mixture was adjusted to a pH of 6 with 1 M hydrochloric acid in water, and concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 42%-52% acetonitrile, 7 min) to give compound 22 formate.

MS-ESI calculated $[M+H]^+$ 507, found 507.

$^1H$ NMR (400 MHz, $CD_3OD$) δ=8.43 (br s, 1H), 7.71-7.51 (m, 5H), 7.11 (d, J=8.4 Hz, 1H), 5.17 (s, 2H), 5.12-5.03 (m, 1H), 3.92-3.77 (m, 2H), 3.28-2.96 (m, 4H), 2.67 (s, 3H), 2.63-2.35 (m, 4H), 2.25 (s, 3H), 2.17-1.98 (m, 1H), 1.12-1.00 (m, 6H).

Example 23

23

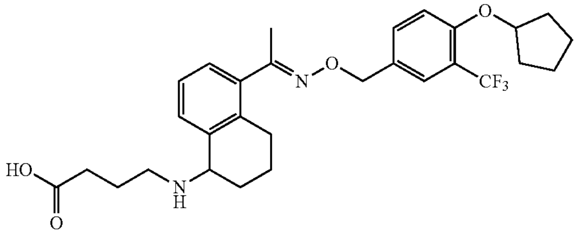

Synthetic Route:

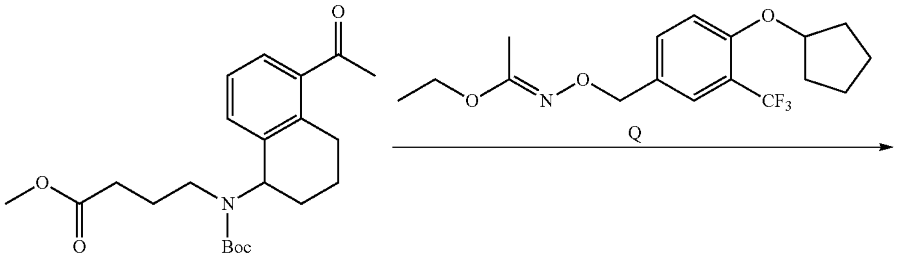

R

-continued

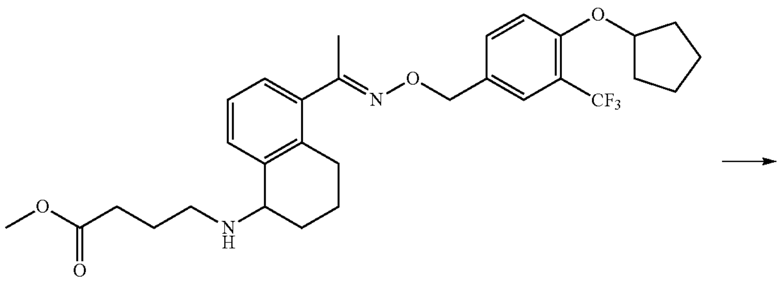

23-1

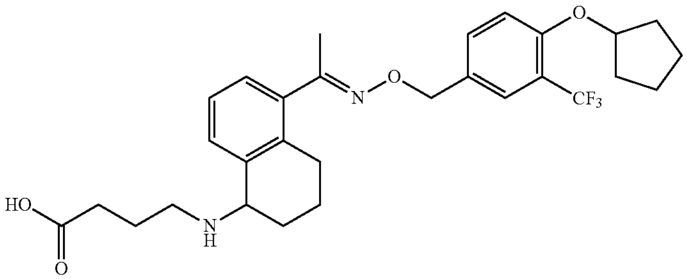

23

Step 1: Synthesis of Compound 23-1

Intermediate Q (191 mg, 514 μmol) was dissolved in methanol (20 mL), and then hydrochloric acid/ethyl acetate (1.60 mL, 4 M) was added dropwise. The mixture was stirred to mix at 20° C. for 0.5 hours, and then triethylamine (519 mg, 5.13 mmol) and intermediate R (100 mg, 257 μmol) were added. The mixture was stirred at 60° C. for 12 hours. The solvent was removed under reduced pressure, and then water (10 mL) was added. The mixture was adjusted to a pH of 8 with saturated sodium bicarbonate, and then extracted with ethyl acetate (15 mL×3). The organic phases were combined, dried over anhydrous sodium sulfate, concentrated under reduced pressure, and then purified by thin-layer chromatography (dichloromethane:methanol=20:1, V:V) to give compound 23-1.

MS-ESI calculated $[M+H]^+$ 547, found 547.

Step 2: Synthesis of Compound 23

Compound 23-1 (130 mg, 238 μmol) was dissolved in a mixed solvent of anhydrous tetrahydrofuran (2 mL), water (1 mL) and absolute ethanol (2 mL), and sodium hydroxide (28.5 mg, 713 μmol) was added. The mixture was reacted at 25° C. for 12 hours. The reaction solution was adjusted to a pH of 6 with 1 M hydrochloric acid, and concentrated under reduced pressure. The resulting crude product was separated by high performance liquid chromatography (Column: Phenomenex Gemini-NX C18 75*30 mm*3 μm; Mobile phase: 0.225% formic acid in water-acetonitrile; Gradient: 38%-48% acetonitrile, 7 min) to give compound 23.

MS-ESI calculated $[M+H]^+$ 533, found 533.

$^1H$ NMR (400 MHz, $CD_3OD$) δ=7.57-7.28 (m, 4H), 7.15-7.03 (m, 2H), 4.98-4.92 (m, 3H), 4.42 (br s, 1H), 3.25-3.15 (m, 1H), 3.15-3.05 (m, 1H), 2.72-2.50 (m, 2H), 2.49-2.41 (m, 2H), 2.19-2.02 (m, 5H), 1.98-1.73 (m, 11H), 1.72-1.61 (m, 2H).

Example 24

24

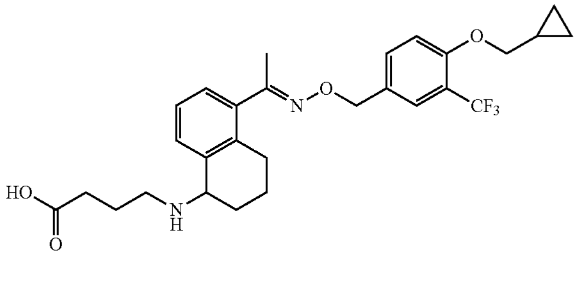

Synthetic Route:

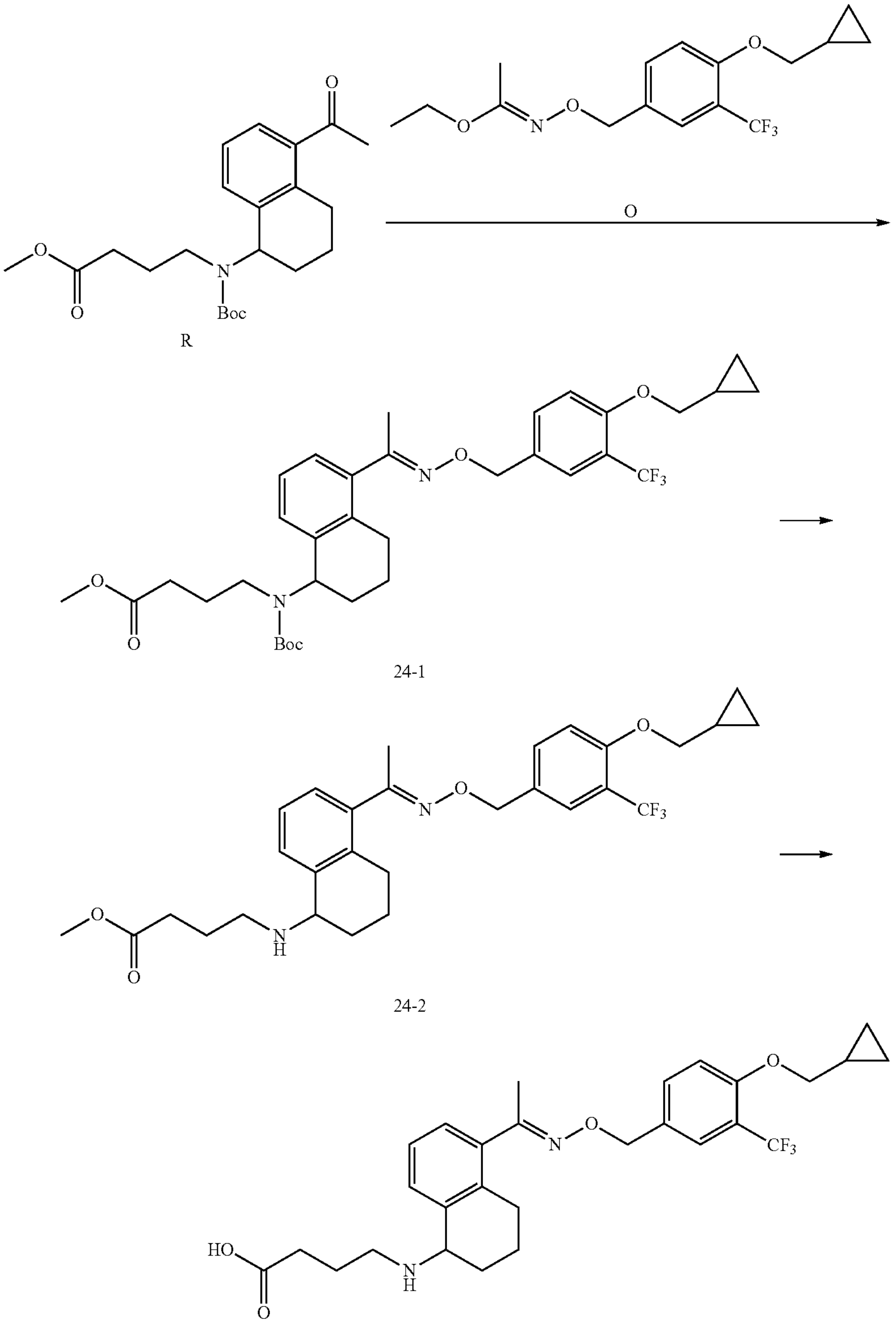

R 24-1

24-2

24

Step 1: Synthesis of Compound 24-1

Intermediate O (191 mg, 514 μmol) was dissolved in methanol (12 mL), and hydrogen chloride/ethyl acetate solution (4 M, 1.60 mL) was added to the reaction solution. The reaction mixture was stirred at 20° C. under nitrogen atmosphere for 0.5 hours. Then triethylamine (5.13 mmol, 715 μL) and intermediate R (100 mg, 257 μmol) were added successively to the reaction solution, and the reaction mixture was stirred at 60° C. for 12 hours. The reaction solution was concentrated under reduced pressure, and the residue was diluted with water (10 mL). The mixture was adjusted to a pH of 8 with saturated aqueous sodium bicarbonate solution, and extracted with ethyl acetate (15 mL×3). The combined organic phase was dried over anhydrous sodium sulfate, and filtered. The filtrate was concentrated under reduced pressure, and the resulting crude product was separated by thin-layer chromatography (petroleum ether/ethyl acetate, 3/1, V/V) to give compound 24-1.

MS-ESI calculated $[M+H]^+$ 633, found 633.

Step 2: Synthesis of Compound 24-2 Hydrochloride

Compound 24-1 (140 mg, 221 μmol) was dissolved in ethyl acetate (4 mL), and hydrogen chloride/ethyl acetate solution (4 M, 4 mL) was added to the reaction solution. The mixture was stirred at 15° C. for 0.5 hours. The reaction solution was concentrated under reduced pressure to give the crude product of compound 24-2 hydrochloride.

MS-ESI calculated $[M+H]^+$ 533, found 533.

Step 3: Synthesis of Compound 24

The crude product of compound 24-2 hydrochloride (128 mg, 225 μmol) was dissolved in THF (2 mL), ethanol (1 mL) and water (2 mL), and sodium hydroxide (18.0 mg, 450 μmol) was added to the reaction mixture. The mixture was stirred at 55° C. for 0.5 hours. The reaction solution was adjusted to a pH of 6 with 1 M hydrochloric acid solution at 0° C., and then concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 38%-48% acetonitrile, 7 min) to give compound 24.

MS-ESI calculated $[M+H]^+$ 519, found 519.

$^1H$ NMR (400 MHz, $CD_3OD$) δ=7.61-7.57 (m, 1H), 7.57-7.48 (m, 2H), 7.35-7.29 (m, 1H), 7.26-7.21 (m, 1H), 7.16-7.10 (m, 1H), 5.16-5.09 (m, 2H), 4.50-4.39 (m, 1H), 4.02-3.95 (m, 2H), 3.23-3.14 (m, 1H), 3.13-3.04 (m, 1H), 2.74-2.65 (m, 1H), 2.63-2.53 (m, 1H), 2.48-2.41 (m, 2H), 2.19-2.15 (m, 3H), 2.14-2.01 (m, 2H), 1.94-1.71 (m, 4H), 1.33-1.22 (m, 1H), 0.65-0.58 (m, 2H), 0.42-0.36 (m, 2H).

Example 25

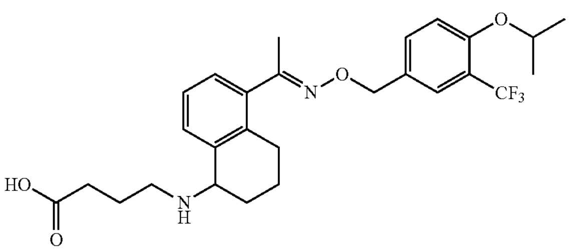

Synthetic Route:

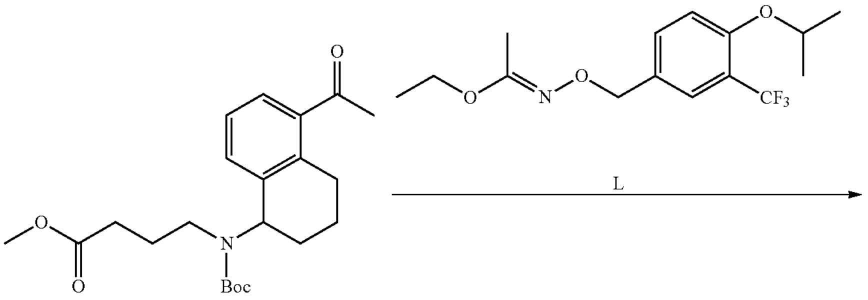

R

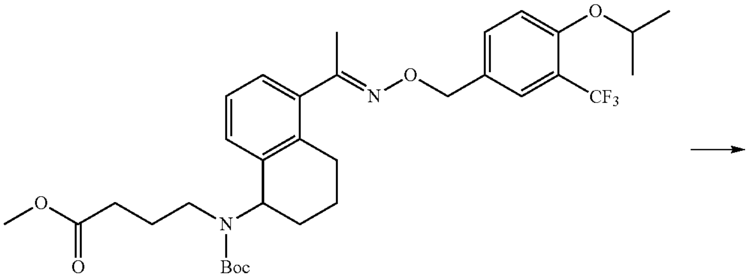

25-1

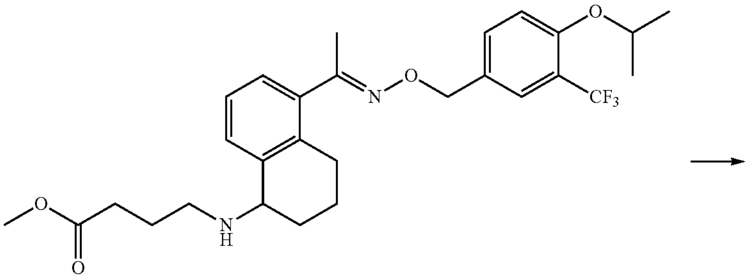

25-2

-continued

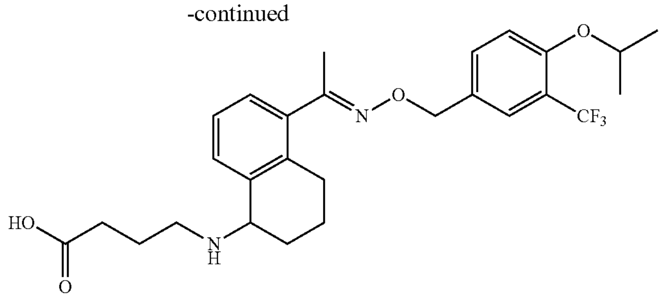

25

Step 1: Synthesis of Compound 25-1

Intermediate L (164 mg, 514 μmol) was dissolved in methanol (12 mL), and hydrogen chloride/ethyl acetate solution (4 M, 1.60 mL) was added to the reaction solution. The reaction mixture was stirred at 20° C. under nitrogen atmosphere for 0.5 hours. Then triethylamine (5.14 mmol, 715 μL) and intermediate R (100 mg, 257 μmol) were added successively to the reaction solution, and the reaction mixture was stirred at 60° C. for 12 hours. The reaction solution was concentrated under reduced pressure, and the residue was diluted with water (10 mL). The mixture was adjusted to a pH of 8 with saturated aqueous sodium bicarbonate solution, and extracted with ethyl acetate (15 mL×3). The combined organic phase was dried over anhydrous sodium sulfate, and filtered. The filtrate was concentrated under reduced pressure, and the resulting crude product was separated by thin-layer chromatography (petroleum ether/ethyl acetate, 3/1, V/V) to give compound 25-1.

MS-ESI calculated $[M+H]^+$ 621, found 621.

Step 2: Synthesis of Compound 25-2 Hydrochloride

Compound 25-1 (114 mg, 184 μmol) was dissolved in ethyl acetate (4 mL), and hydrogen chloride/ethyl acetate solution (4 M, 4 mL) was added to the reaction solution. The mixture was stirred at 15° C. for 0.5 hours. The reaction solution was concentrated under reduced pressure to give the crude product of compound 25-2 hydrochloride.

MS-ESI calculated $[M+H]^+$ 521, found 521.

Step 3: Synthesis of Compound 25

The crude product of compound 25-2 hydrochloride (105 mg, 189 μmol) was dissolved in THF (2 mL), ethanol (1 mL) and water (2 mL), and sodium hydroxide (18.0 mg, 450 μmol) was added to the reaction mixture. The mixture was stirred at 55° C. for 0.5 hours. The reaction solution was adjusted to a pH of 6 with 1 M hydrochloric acid solution at 0° C., and then concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 35%-45% acetonitrile, 7 min) to give compound 25.

MS-ESI calculated $[M+H]^+$ 507, found 507.

$^1H$ NMR (400 MHz, $CD_3OD$) δ=7.61-7.47 (m, 3H), 7.36-7.29 (m, 1H), 7.27-7.21 (m, 1H), 7.20-7.14 (m, 1H), 5.15-5.08 (m, 2H), 4.80-4.69 (m, 1H), 4.48-4.39 (m, 1H), 3.24-3.15 (m, 1H), 3.13-3.04 (m, 1H), 2.76-2.65 (m, 1H), 2.63-2.54 (m, 1H), 2.49-2.39 (m, 2H), 2.22-2.15 (m, 3H), 2.14-1.99 (m, 2H), 1.96-1.73 (m, 4H), 1.40-1.29 (m, 6H).

Example 26

26

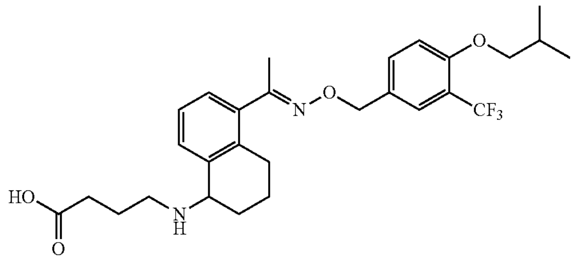

Synthetic Route:

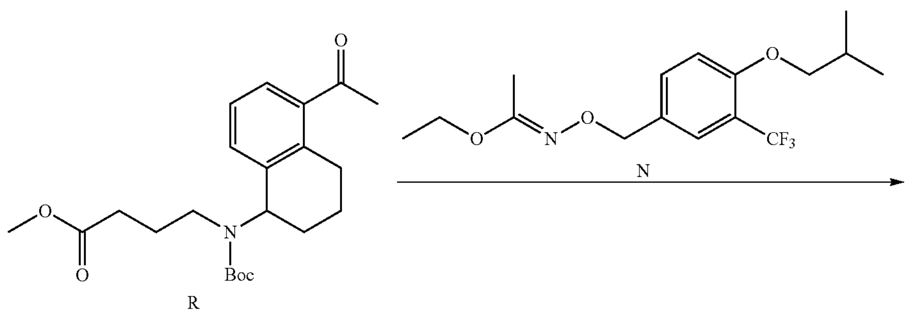

R

-continued

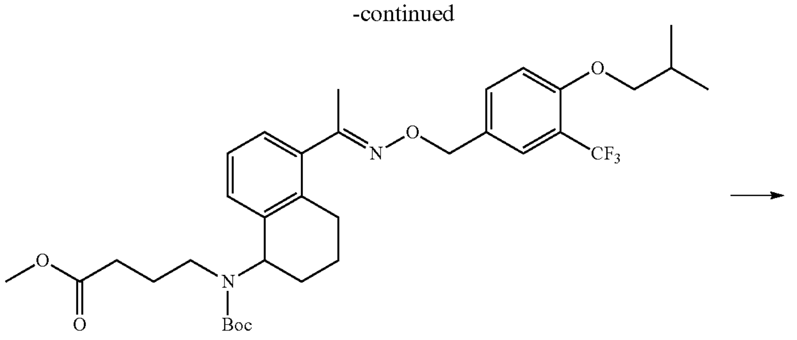

26-1

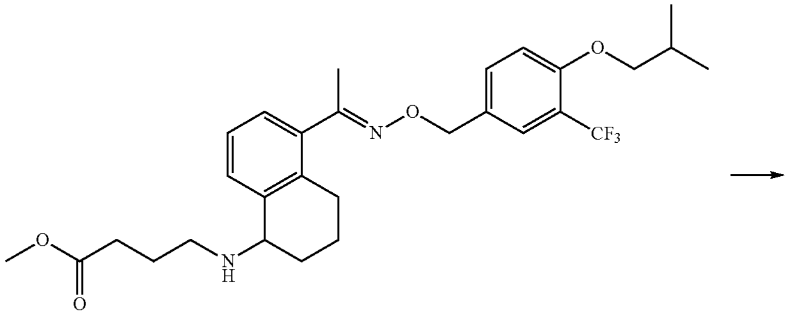

26-2

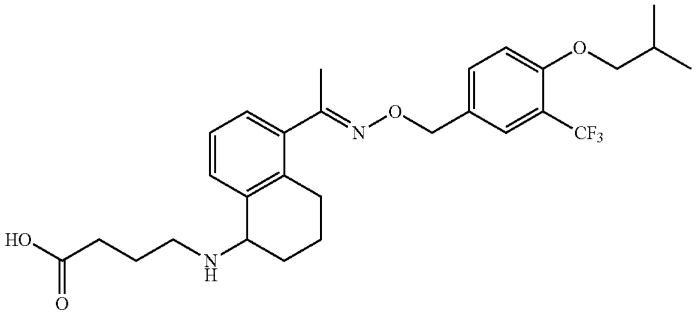

26

Step 1: Synthesis of Compound 26-1

Intermediate N (171 mg, 514 μmol) was dissolved in methanol (12 mL), and hydrogen chloride/ethyl acetate solution (4 M, 1.60 mL) was added to the reaction solution. The reaction mixture was stirred at 20° C. under nitrogen atmosphere for 0.5 hours. Then triethylamine (5.14 mmol, 715 μL) and intermediate R (100 mg, 257 μmol) were added successively to the reaction solution, and the reaction mixture was stirred at 60° C. for 12 hours. The reaction solution was concentrated under reduced pressure, and the residue was diluted with water (10 mL). The mixture was adjusted to a pH of 8 with saturated aqueous sodium bicarbonate solution, and extracted with ethyl acetate (15 mL×3). The combined organic phase was dried over anhydrous sodium sulfate, and filtered. The filtrate was concentrated under reduced pressure, and the resulting crude product was separated by thin-layer chromatography (petroleum ether/ethyl acetate, 3/1, V/V) to give compound 26-1.

MS-ESI calculated $[M+H]^+$ 635, found 635.

Step 2: Synthesis of Compound 26-2 Hydrochloride

Compound 26-1 (110 mg, 173 μmol) was dissolved in ethyl acetate (4 mL), and hydrogen chloride/ethyl acetate solution (4 M, 4 mL) was added to the reaction solution. The mixture was stirred at 15° C. for 0.5 hours. The reaction solution was concentrated under reduced pressure to give the crude product of compound 26-2 hydrochloride.

MS-ESI calculated $[M+H]^+$ 535, found 535.

Step 3: Synthesis of Compound 26

The crude product of compound 26-2 hydrochloride (100 mg, 175 μmol) was dissolved in THF (2 mL), ethanol (1 mL) and water (2 mL), and sodium hydroxide (14.0 mg, 350 μmol) was added to the reaction mixture. The mixture was stirred at 55° C. for 0.5 hours. The reaction solution was adjusted to a pH of 6 with 1 M hydrochloric acid solution at 0° C., and then concentrated under reduced pressure. The resulting crude product was separated by high performance liquid chromatography (Column: Phenomenex Gemini-NX C18 75×30 mm×3 m; Mobile phase: 10 mmol/L aqueous ammonium bicarbonate solution-acetonitrile; Gradient: 32%-62% acetonitrile, 8 min) to give compound 26.

MS-ESI calculated $[M+H]^+$ 521, found 521.

$^1H$ NMR (400 MHz, $CD_3OD$) δ=7.61-7.54 (m, 2H), 7.53-7.48 (m, 1H), 7.34-7.28 (m, 1H), 7.24-7.20 (m, 1H), 7.16-7.11 (m, 1H), 5.14-5.09 (m, 2H), 4.41-4.34 (m, 1H), 3.90-3.84 (m, 2H), 3.21-3.12 (m, 1H), 3.09-3.00 (m, 1H), 2.73-2.63 (m, 1H), 2.63-2.51 (m, 1H), 2.45-2.40 (m, 2H), 2.17 (s, 3H), 2.14-2.00 (m, 3H), 1.92-1.70 (m, 4H), 1.10-1.02 (m, 6H).
Example 27
27
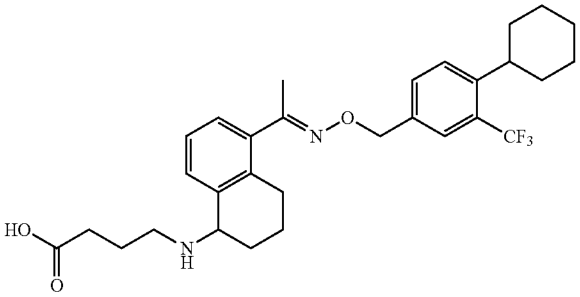
Synthetic Route:
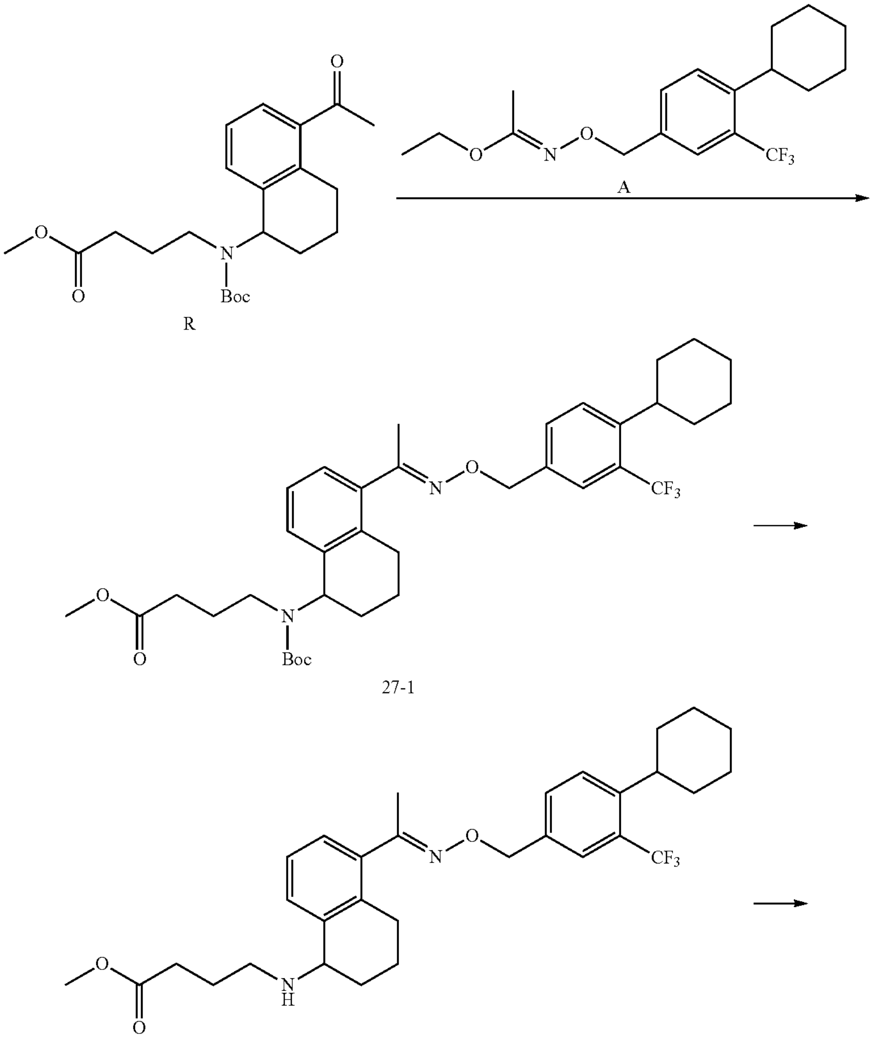
R
27-1
27-2

-continued

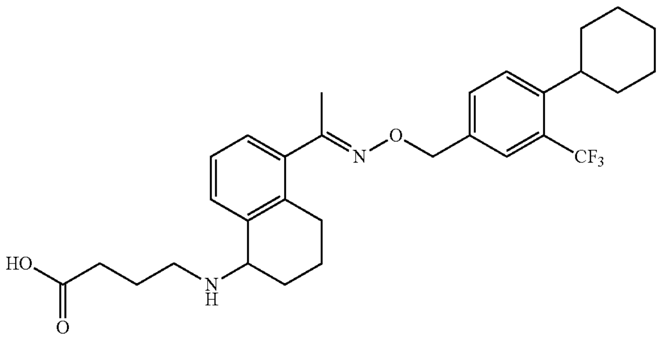

27

Step 1: Synthesis of Compound 27-1

Intermediate A (176 mg, 514 μmol) was dissolved in methanol (12 mL), and hydrogen chloride/ethyl acetate solution (4 M, 1.60 mL) was added to the reaction solution. The reaction mixture was stirred at 20° C. under nitrogen atmosphere for 0.5 hours. Then triethylamine (5.14 mmol, 715 μL) and intermediate R (100 mg, 257 μmol) were added successively to the reaction solution, and the reaction mixture was stirred at 60° C. for 12 hours. The reaction solution was concentrated under reduced pressure, and the residue was diluted with water (20 mL). The mixture was adjusted to a pH of 8 with saturated aqueous sodium bicarbonate solution, and extracted with ethyl acetate (15 mL×3). The combined organic phase was dried over anhydrous sodium sulfate, and filtered. The filtrate was concentrated under reduced pressure, and the resulting crude product was separated by thin-layer chromatography (petroleum ether/ethyl acetate, 3/1, V/V) to give compound 27-1.

MS-ESI calculated $[M+H]^+$ 645, found 645.

Step 2: Synthesis of Compound 27-2 Hydrochloride

Compound 27-1 (134 mg, 208 μmol) was dissolved in ethyl acetate (4 mL), and hydrogen chloride/ethyl acetate solution (4 M, 4 mL) was added to the reaction solution. The mixture was stirred at 15° C. for 0.5 hours. The reaction solution was concentrated under reduced pressure to give the crude product of compound 27-2 hydrochloride.

MS-ESI calculated $[M+H]^+$ 545, found 545.

Step 3: Synthesis of Compound 27

The crude product of compound 27-2 hydrochloride (123 mg, 212 μmol) was dissolved in THF (2 mL), ethanol (1 mL) and water (2 mL), and sodium hydroxide (16.9 mg, 423 μmol) was added to the reaction mixture. The mixture was stirred at 55° C. for 3 hours. The reaction solution was adjusted to a pH of 6 with 1 M hydrochloric acid solution at 0° C., and then concentrated under reduced pressure. The resulting crude product was separated by high performance liquid chromatography (Column: Phenomenex Gemini-NX C18 75×30 mm×3 μm; Mobile phase: 0.225% formic acid in water-acetonitrile; Gradient: 40%-50% acetonitrile, 7 min) to give compound 27.

MS-ESI calculated $[M+H]^+$ 531, found 531.

$^1H$ NMR (400 MHz, $CD_3OD$) δ=7.65-7.60 (m, 1H), 7.59-7.47 (m, 3H), 7.36-7.29 (m, 1H), 7.27-7.21 (m, 1H), 5.22-5.13 (m, 2H), 4.52-4.38 (m, 1H), 3.24-3.14 (m, 1H), 3.13-3.04 (m, 1H), 2.98-2.88 (m, 1H), 2.75-2.65 (m, 1H), 2.64-2.53 (m, 1H), 2.49-2.41 (m, 2H), 2.24-2.16 (m, 3H), 2.16-2.00 (m, 2H), 1.94-1.72 (m, 9H), 1.62-1.35 (m, 5H).

Example 28

28

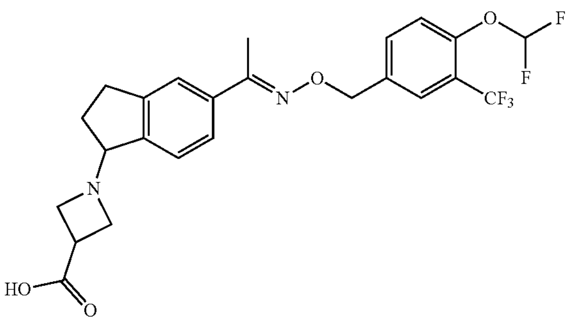

Synthetic Route:

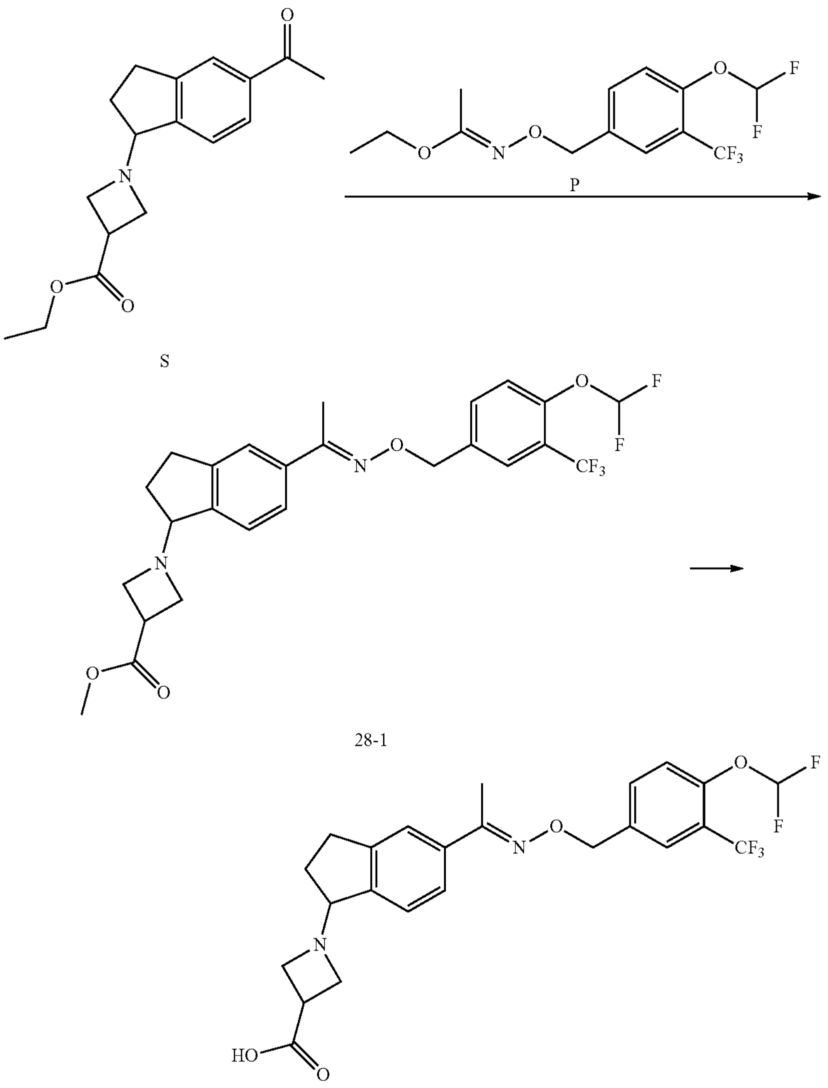

S 28-1

28

Step 1: Synthesis of Compound 28-1

Intermediate P (143 mg, 438 μmol) was dissolved in methanol (2 mL), and hydrogen chloride/ethyl acetate solution (4 M, 1.37 mL) was added to the reaction solution. The reaction mixture was stirred at 20° C. under nitrogen atmosphere for 0.5 hours. Then triethylamine (4.38 mmol, 610 μL) and intermediate S (100 mg, 219 μmol) were added successively to the reaction solution, and the reaction mixture was stirred at 60° C. for 12 hours. The reaction solution was concentrated under reduced pressure, and the residue was diluted with saturated aqueous sodium bicarbonate solution (100 mL). The mixture was extracted with ethyl acetate (100 mL×3). The combined organic phase was dried over anhydrous sodium sulfate, and filtered. The filtrate was concentrated under reduced pressure to give compound 28-1.

MS-ESI calculated $[M+H]^+$ 513, found 513.

Step 2: Synthesis of Compound 28

Compound 28-1 (70.0 mg, 137 μmol) was dissolved in THF (2 mL) ethanol (1 mL) and water (2 mL), and sodium hydroxide (10.9 mg, 273 μmol) was added to the reaction mixture. The mixture was stirred at 55° C. for 3 hours. The reaction solution was adjusted to a pH of 4~5 with 4 M hydrochloric acid solution, and then concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 35%-45% acetonitrile, 7 min) to give compound 28.

MS-ESI calculated $[M+H]^+$ 499, found 499.

$^1H$ NMR (400 MHz, $CD_3Cl$) δ=7.70 (s, 1H), 7.63-7.39 (m, 4H), 7.30 (br d, J=8.4 Hz, 1H), 6.77-6.30 (m, 1H), 5.21 (s, 2H), 4.51 (br s, 1H), 4.40-4.26 (m, 1H), 4.18 (br d, J=2.1 Hz, 1H), 3.89 (br d, J=9.3 Hz, 2H), 3.21 (br s, 2H), 2.95-2.82 (m, 1H), 2.33 (br d, J=4.0 Hz, 2H), 2.24 (s, 3H).

Example 29
29
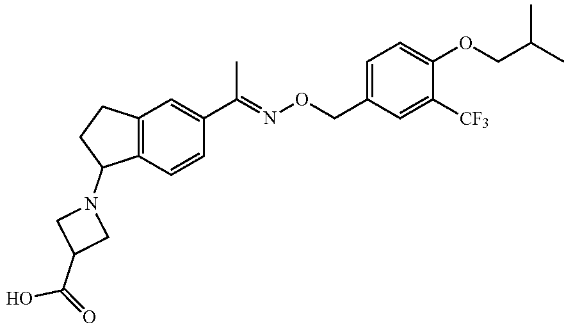
Synthetic Route:
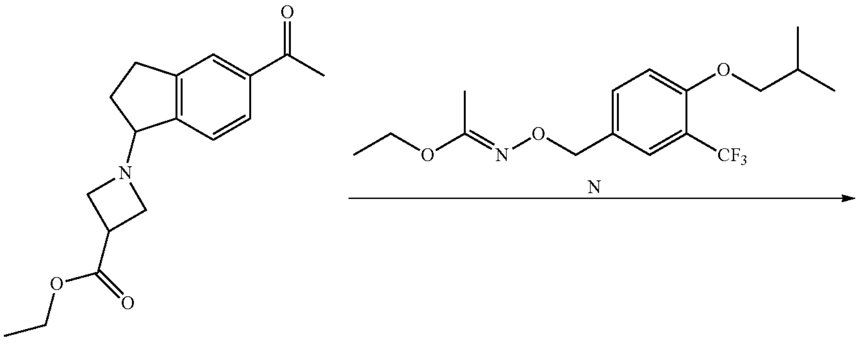
S
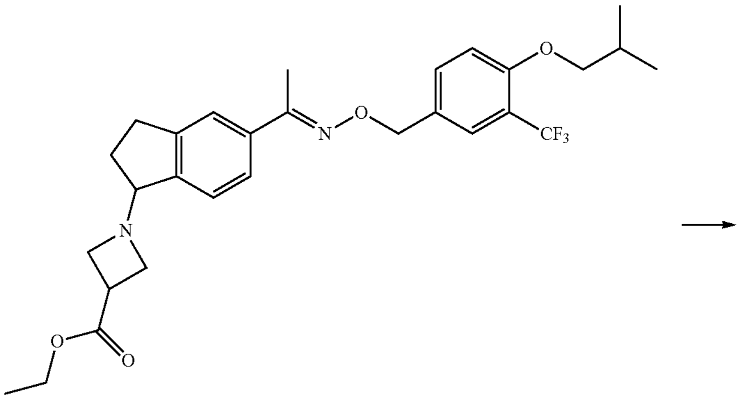
29-1

-continued

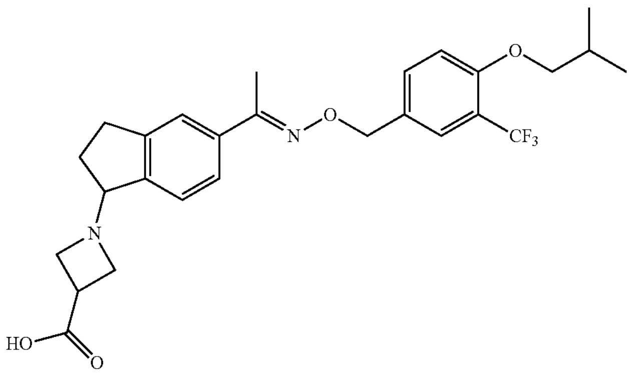

29

Step 1: Synthesis of Compound 29-1

Intermediate N (148 mg, 444 μmol) was dissolved in methanol (20 mL) under nitrogen atmosphere, and hydrogen chloride/ethyl acetate solution (4 M, 1.39 mL) was added to the reaction solution. The reaction mixture was stirred at 20° C. for 0.5 hours. Then triethylamine (4.44 mmol, 619 μL) and intermediate S (100 mg, 222 μmol) were added successively to the reaction solution, and the reaction mixture was stirred at 60° C. for 5 hours. The reaction solution was concentrated under reduced pressure, and the residue was diluted with aqueous saturated sodium bicarbonate solution (50 mL). The mixture was extracted with ethyl acetate (50 mL×2). The combined organic phase was dried over anhydrous sodium sulfate, and filtered. The filtrate was concentrated under reduced pressure, and the resulting crude product was separated by thin-layer chromatography (dichloromethane/methanol, 20/1, V/V) to give the crude product of compound 29-1.

MS-ESI calculated $[M+H]^+$ 533, found 533.

Step 2: Synthesis of Compound 29

The crude product of compound 29-1 (140 mg, 263 μmol) was dissolved in THF (2 mL), ethanol (1 mL) and water (2 mL), and sodium hydroxide (10.5 mg, 263 μmol) was added to the reaction mixture. The mixture was stirred at 55° C. for 3 hours. The reaction solution was adjusted to a pH of 4~5 with 4 M hydrochloric acid solution, and then concentrated under reduced pressure. The resulting crude product was separated by high performance liquid chromatography (Column: Phenomenex Gemini-NX C18 75×30 mm×3 μm; Mobile phase: 0.225% formic acid in water-acetonitrile; Gradient: 42%-52% acetonitrile, 7 min) to give compound 29.

MS-ESI calculated $[M+H]^+$ 505, found 505.

$^1H$ NMR (400 MHz, $CD_3Cl$) δ=7.61 (s, 1H), 7.58-7.39 (m, 4H), 6.94 (d, J=8.4 Hz, 1H), 5.14 (s, 2H), 4.50 (br s, 1H), 4.25 (br s, 1H), 4.19-4.00 (m, 1H), 3.98-3.83 (m, 2H), 3.80 (d, J=6.4 Hz, 2H), 3.28-3.14 (m, 2H), 2.95-2.79 (m, 1H), 2.42-2.26 (m, 2H), 2.20 (s, 3H), 2.17-2.06 (m, 1H), 1.04 (d, J=6.6 Hz, 6H).

Example 30

30

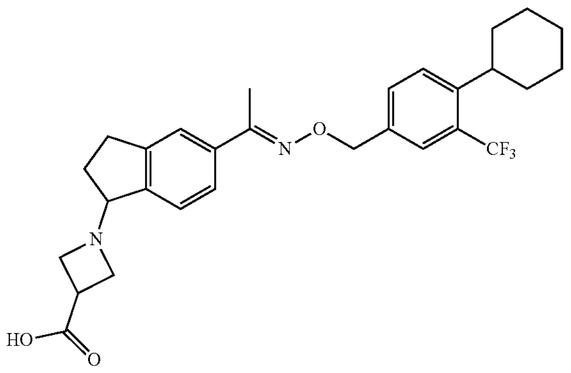

Synthetic Route:

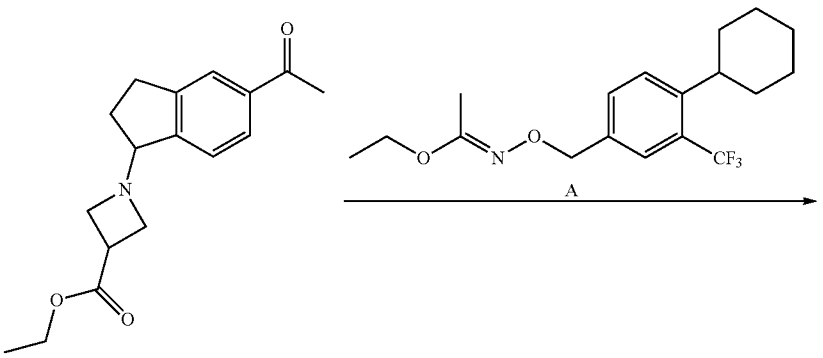

S

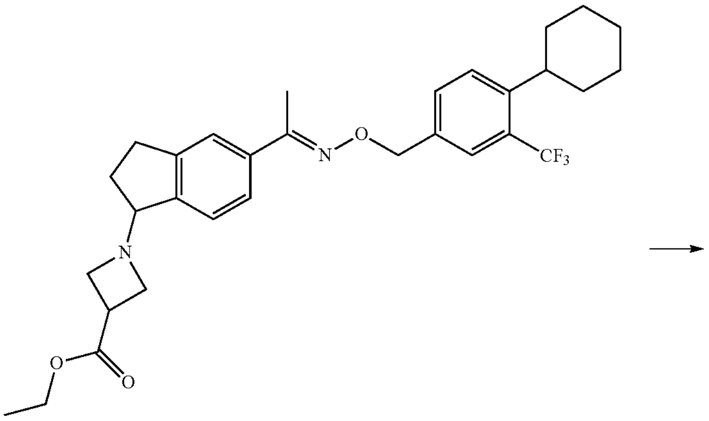

30-1

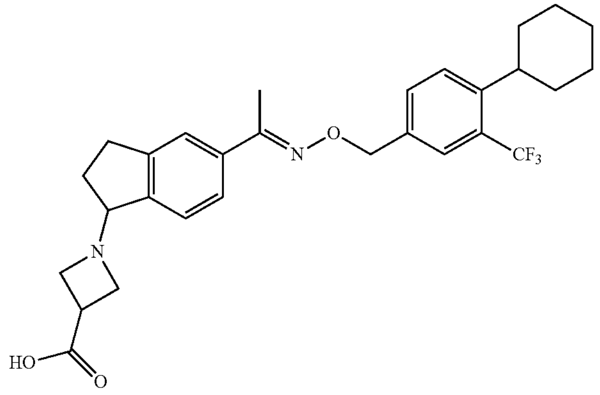

30

Step 1: Synthesis of Compound 30-1

Intermediate A (153 mg, 444 mol) was dissolved in methanol (20 mL), and hydrogen chloride/ethyl acetate solution (4 M, 1.39 mL) was added to the reaction solution. The reaction mixture was stirred at 20° C. under nitrogen atmosphere for 0.5 hours. Then triethylamine (4.44 mmol, 619 μL) and intermediate S (100 mg, 222 μmol) were added successively to the reaction solution, and the reaction mixture was stirred at 60° C. for 5 hours. The reaction solution was concentrated under reduced pressure, and the residue was diluted with aqueous saturated sodium bicarbonate solution (50 mL). The mixture was extracted with ethyl acetate (50 mL×2). The combined organic phase was dried over anhydrous sodium sulfate, and filtered. The filtrate was concentrated under reduced pressure, and the resulting crude product was separated by thin-layer chromatography (dichloromethane/methanol, 20/1, V/V) to give the crude product of compound 30-1.

MS-ESI calculated $[M+H]^+$ 543, found 543.

Step 2: Synthesis of Compound 30

The crude product of compound 30-1 (140 mg, 258 μmol) was dissolved in THF (2 mL), ethanol (1 mL) and water (2 mL), and sodium hydroxide (20.6 mg, 516 μmol) was added to the reaction mixture. The mixture was stirred at 55° C. for 3 hours. The reaction solution was adjusted to a pH of 4~5 with 4 M hydrochloric acid solution, and then concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 38%-68% acetonitrile, 7 min) to give compound 30.
MS-ESI calculated $[M+H]^+$ 515, found 515.
$^1H$ NMR (400 MHz, $CD_3Cl$) δ=7.63 (s, 1H), 7.57 (s, 1H), 7.55-7.47 (m, 2H), 7.47-7.40 (m, 2H), 5.21 (s, 2H), 4.67-4.56 (m, 1H), 4.36-4.20 (m, 1H), 4.19-4.09 (m, 1H), 4.09-3.96 (m, 2H), 3.43-3.30 (m, 1H), 3.30-3.11 (m, 1H), 3.01-2.83 (m, 2H), 2.50-2.30 (m, 2H), 2.24 (s, 3H), 1.92-1.70 (m, 5H), 1.49-1.25 (m, 5H).
Example 31
31
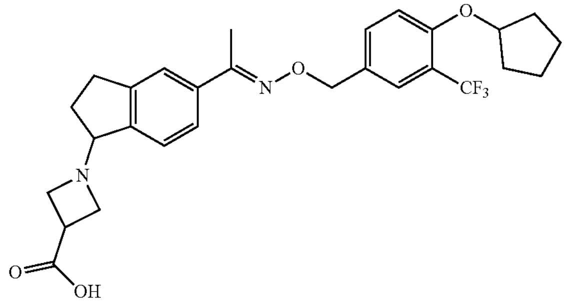
Synthetic Route:
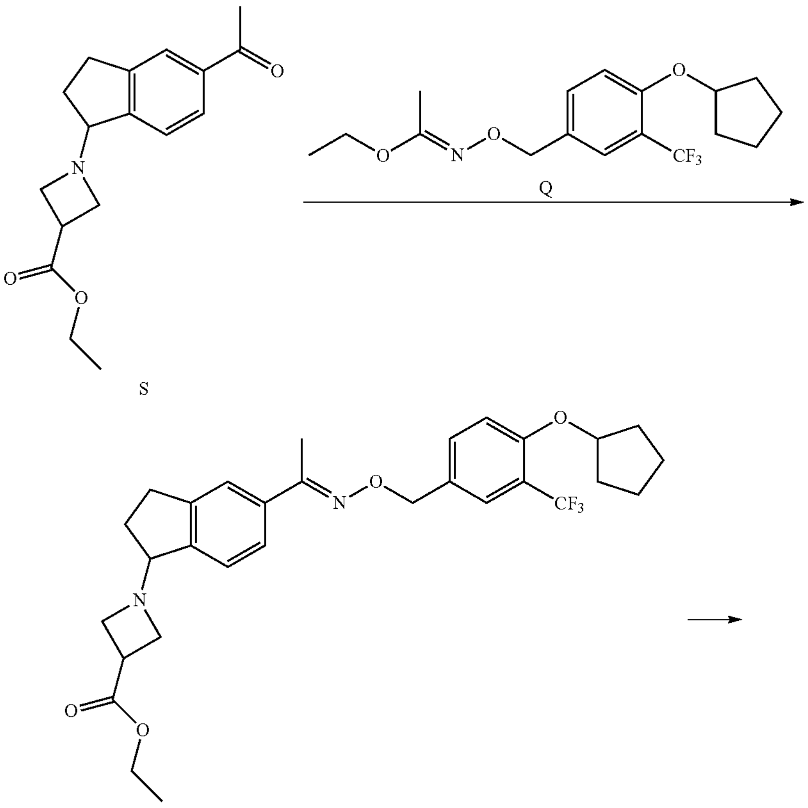
S
Q
31-1

-continued

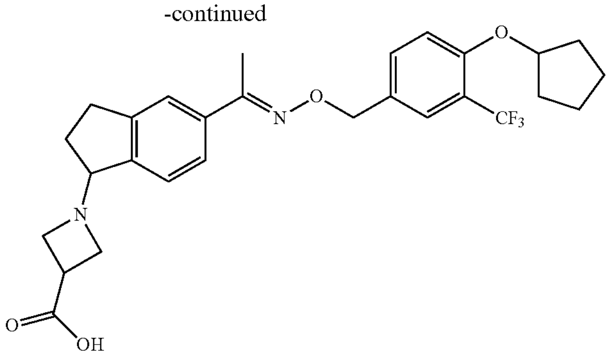

31

Step 1: Synthesis of Compound 31-1

Intermediate Q (166 mg, 444 μmol) was dissolved in methanol (20 mL), and hydrogen chloride/ethyl acetate solution (1.39 mL, 4 M) was added to the reaction solution. The reaction mixture was stirred at 20° C. for 0.5 hours. Then triethylamine (450 mg, 4.44 mmol) and intermediate S (100 mg, 222 μmol) were added successively to the reaction solution, and the reaction mixture was stirred at 60° C. for 5 hours. The reaction solution was concentrated under reduced pressure to remove the solvent. Water (10 mL) was added to the residue. The mixture was adjusted to a pH of 8 with saturated aqueous sodium bicarbonate solution, and extracted with ethyl acetate (15 mL×3). The organic phases were combined, dried over anhydrous sodium sulfate, concentrated under reduced pressure, and then purified by thin-layer chromatography (dichloromethane:methanol=20:1, V:V) to give the crude product of compound 31-1.

MS-ESI calculated $[M+H]^+$ 545, found 545.

Step 2: Synthesis of Compound 31

The crude product of compound 31-1 (170 mg, 226 μmol) was dissolved in a mixed solvent of anhydrous tetrahydrofuran (2 mL), water (1 mL) and absolute ethanol (2 mL), and sodium hydroxide (18.1 mg, 451 μmol) was added. The reaction solution was stirred at 25° C. for 12 hours. The reaction solution was adjusted to a pH of 6 with 1 M hydrochloric acid solution, and then concentrated under reduced pressure. The resulting crude product was separated by high performance liquid chromatography (Column: Phenomenex Gemini-NX C18 75*30 mm*3 m; Mobile phase: 0.225% formic acid in water-acetonitrile; Gradient: 32%-62% acetonitrile, 7 min) to give compound 31.

MS-ESI calculated $[M+H]^+$ 517, found 517.

$^1$H NMR (400 MHz, $CD_3OD$) δ=7.66 (s, 1H), 7.64-7.51 (m, 4H), 7.13 (d, J=8.4 Hz, 1H), 5.16 (s, 2H), 4.98-4.93 (m, 1H), 4.90 (br d, J=2.5 Hz, 1H), 4.43-4.35 (m, 2H), 4.29-4.21 (m, 2H), 3.45 (m, J=8.4 Hz, 1H), 3.21-3.10 (m, 1H), 3.04-2.95 (m, 1H), 2.57-2.45 (m, 1H), 2.24 (s, 3H), 2.22-2.14 (m, 1H), 1.99-1.89 (m, 2H), 1.89-1.76 (m, 4H), 1.72-1.61 (m, 2H).

Example 32

32

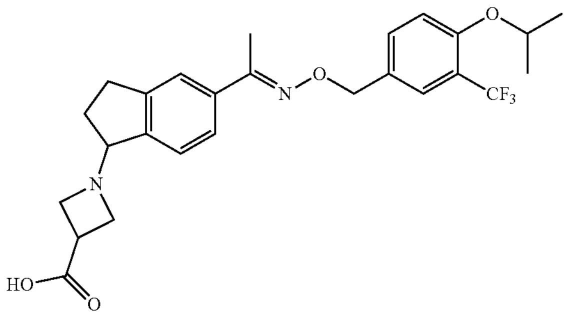

Synthetic Route:

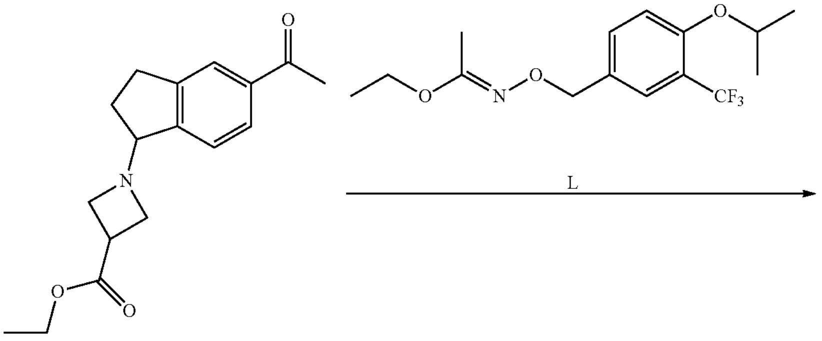

S

-continued

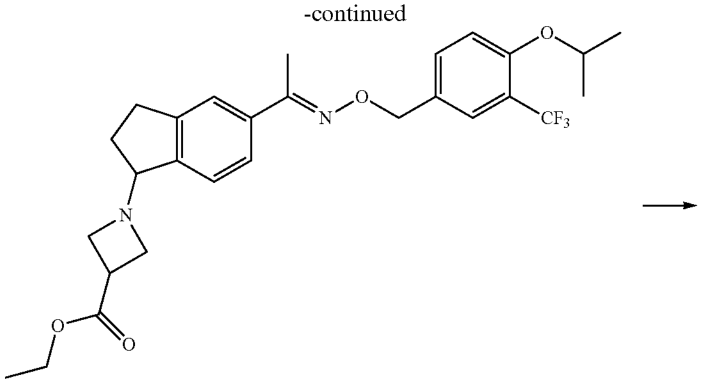

32-1

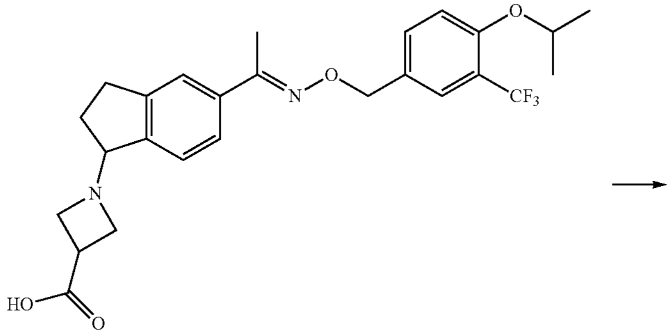

32

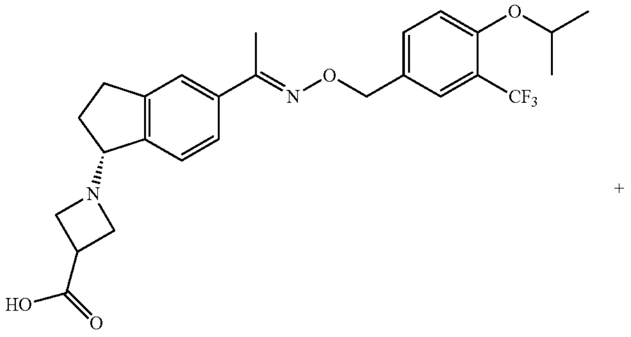

32A or 32B

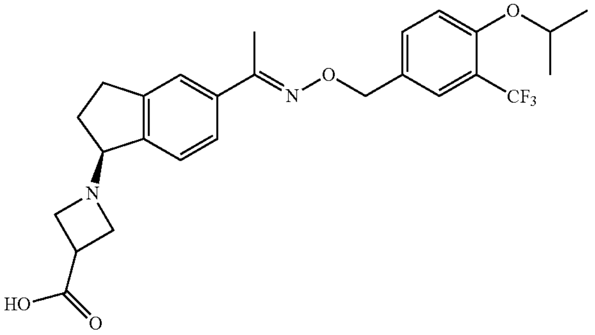

32B or 32A

Step 1: Synthesis of Compound 32-1

Intermediate L (95.1 mg, 298 μmol) was dissolved in methanol (20 mL) under nitrogen atmosphere, and hydrogen chloride/ethyl acetate solution (4 M, 931 μL) was added to the reaction solution. The reaction mixture was stirred at 20° C. for 0.5 hours. Then triethylamine (2.98 mmol, 415 μL) and intermediate S (100 mg, 149 μmol) were added successively to the reaction solution, and the reaction mixture was stirred at 60° C. for 5 hours. The intermediate S (50 mg) batches were combined. The reaction solution was concentrated under reduced pressure, and the residue was diluted with water (10 mL). The mixture was adjusted to a pH of 8 with saturated aqueous sodium bicarbonate solution, and extracted with ethyl acetate (15 mL×3). The combined organic phase was dried over anhydrous sodium sulfate, and filtered. The filtrate was concentrated under reduced pressure, and the resulting crude product was separated by thin-layer chromatography (dichloromethane/methanol, 20/1, V/V) to give compound 32-1.

MS-ESI calculated $[M+H]^+$ 519, found 519.

Step 2: Synthesis of Compound 32

Compound 32-1 (100 mg, 193 μmol) was dissolved in THF (2 mL), ethanol (1 mL) and water (2 mL), and sodium hydroxide (15.4 mg, 386 μmol) was added to the reaction mixture. The mixture was stirred at 55° C. for 3 hours. The reaction solution was adjusted to a pH of 6 with 1 M hydrochloric acid solution at 0° C., and then concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 30%-60% acetonitrile, 7 min) to give compound 32.

MS-ESI calculated $[M+H]^+$ 491, found 491.

$^1H$ NMR (400 MHz, $CD_3OD$) δ=7.66 (s, 1H), 7.63-7.55 (m, 3H), 7.55-7.51 (m, 1H), 7.16 (d, J=8.5 Hz, 1H), 5.16 (s, 2H), 4.86-4.70 (m, 2H), 4.38-4.30 (m, 2H), 4.21 (t, J=8.9 Hz, 2H), 3.43-3.35 (m, 1H), 3.20-3.09 (m, 1H), 3.04-2.95 (m, 1H), 2.56-2.44 (m, 1H), 2.24 (s, 3H), 2.22-2.13 (m, 1H), 1.34 (d, J=6.0 Hz, 6H).

Step 3: Synthesis of Compounds 32A and 32B

Compound 32 was separated by SFC (Column: DAICEL CHIRALPAK IC 250 mm×30 mm, 10 μm; Mobile phase: 0.1% ammonia in water-methanol; Gradient: methanol 35%-35%, 4.3 min; 140 min) to give compounds 32A and 32B respectively. The retention time for 32A was 1.27 min, ee %=100%, and the retention time for 32B was 1.68 min, ee %=98.21%.

Example 33

33

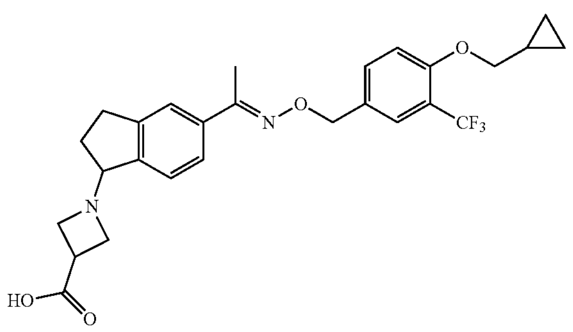

Synthetic Route:

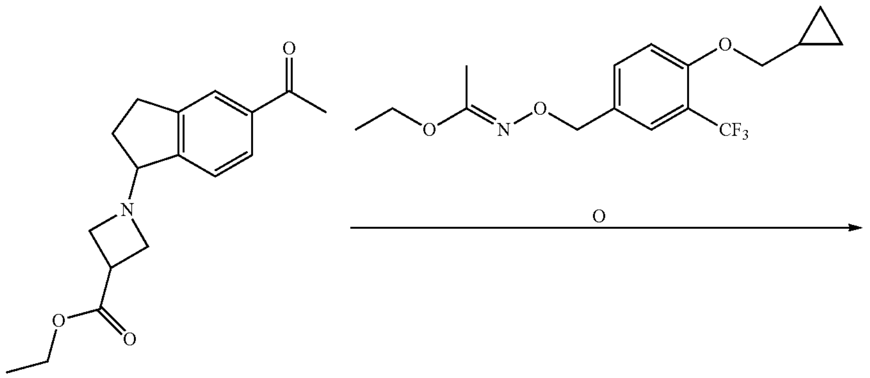

S

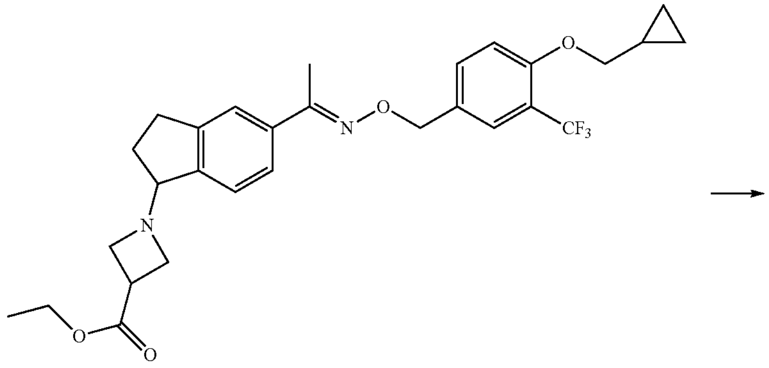

33-1

-continued

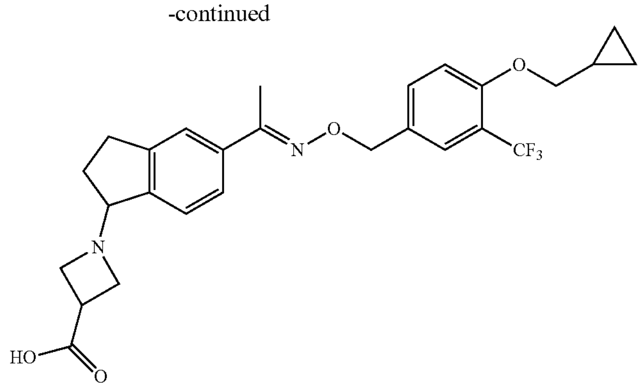

33

Step 1: Synthesis of Compound 33-1

Intermediate O (165 mg, 444 μmol) was dissolved in methanol (20 mL) under nitrogen atmosphere, and hydrogen chloride/ethyl acetate solution (4 M, 1.39 mL) was added to the reaction solution. The reaction mixture was stirred at 20° C. for 0.5 hours. Then triethylamine (4.44 mmol, 619 μL) and intermediate S (100 mg, 222 μmol) were added successively to the reaction solution, and the reaction mixture was stirred at 60° C. for 3 hours. The reaction solution was concentrated under reduced pressure, and the residue was diluted with water (10 mL). The mixture was adjusted to a pH of 8 with saturated aqueous sodium bicarbonate solution, and extracted with ethyl acetate (15 mL×3). The combined organic phase was dried over anhydrous sodium sulfate, and filtered. The filtrate was concentrated under reduced pressure, and the resulting crude product was separated by thin-layer chromatography (dichloromethane/methanol, 20/1, V/V) to give compound 33-1.

MS-ESI calculated $[M+H]^+$ 531, found 531.

Step 2: Synthesis of Compound 33

Compound 33-1 (114 mg, 215 μmol) was dissolved in THF (2 mL), ethanol (1 mL) and water (2 mL), and sodium hydroxide (17.2 mg, 430 μmol) was added to the reaction mixture. The mixture was stirred at 55° C. for 3 hours. The reaction solution was adjusted to a pH of 6 with 1 M hydrochloric acid solution at 0° C., and then concentrated under reduced pressure. The resulting crude product was separated by high performance liquid chromatography (Column: Phenomenex Gemini-NX C18 75×30 mm×3 m; Mobile phase: 0.225% formic acid in water-acetonitrile; Gradient: 30%-60% acetonitrile, 7 min) to give compound 33.

MS-ESI calculated $[M+H]^+$ 503, found 503.

$^1H$ NMR (400 MHz, $CD_3OD$) δ=7.66-7.64 (m, 1H), 7.62-7.55 (m, 3H), 7.54-7.50 (m, 1H), 7.15-7.09 (m, 1H), 5.22-5.12 (m, 2H), 4.86-4.82 (m, 1H), 4.41-4.30 (m, 2H), 4.26-4.15 (m, 2H), 4.00-3.92 (m, 2H), 3.44-3.33 (m, 1H), 3.21-3.10 (m, 1H), 3.04-2.93 (m, 1H), 2.55-2.43 (m, 1H), 2.25-2.22 (m, 3H), 2.21-2.13 (m, 1H), 1.34-1.18 (m, 1H), 0.64-0.57 (m, 2H), 0.43-0.34 (m, 2H).

Example 34

34

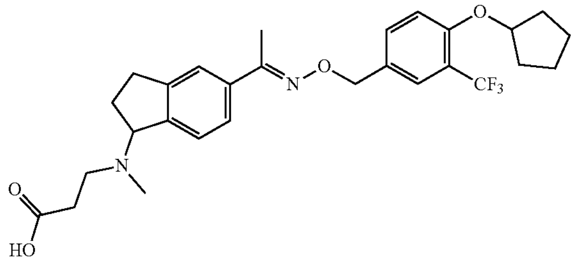

Synthetic Route:

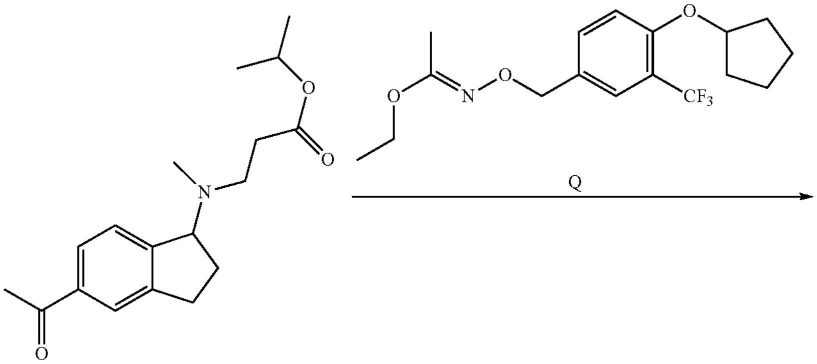

M

-continued

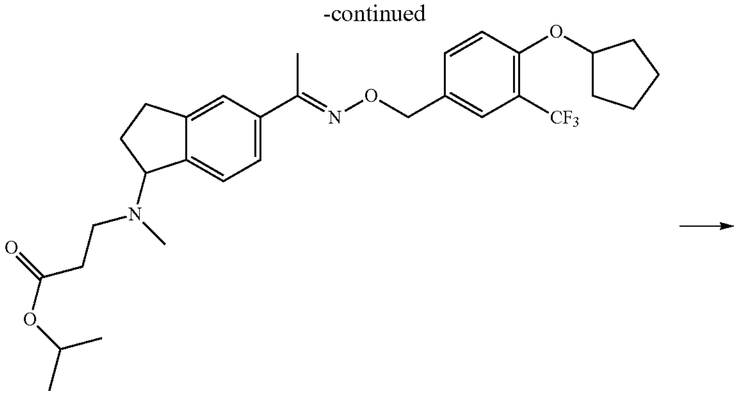

34-1

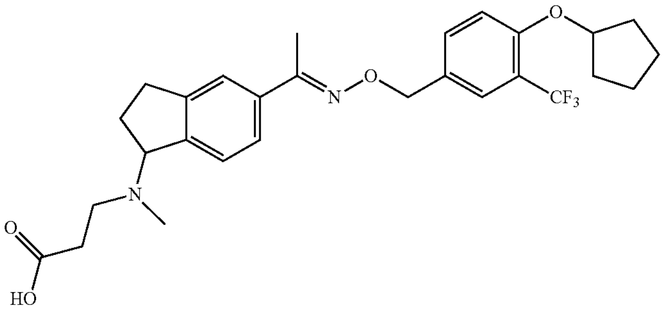

34

Step 1: Synthesis of Compound 34-1

To a solution of intermediate Q (170.75 mg, 494.40 μmol) in methanol (2 mL) was added hydrochloric acid/ethyl acetate (4 M, 1.24 mL, 4.94 mmol), and the reaction solution was reacted at 20° C. for 0.5 hours. Triethylamine (400 mg, 3.96 mmol) was added dropwise to the reaction solution, and intermediate M (150 mg, 494 μmol) was added. The reaction solution was reacted at 60° C. for 3 hours. The reaction solution was adjusted to a pH of 8 with saturated aqueous sodium bicarbonate solution, and diluted with water (50 mL). The aqueous phase was extracted with ethyl acetate (50 mL×2). The organic phases were combined, dried over anhydrous sodium sulfate, and filtered. The filtrate was concentrated under reduced pressure, and the resulting crude product was separated by thin-layer chromatography (dichloromethane/methanol, 20/1, V/V) to give compound 34-1.

MS-ESI calculated $[M+H]^+$ 561, found 561.

Step 2: Synthesis of Compound 34

Compound 34-1 (140 mg, 262.86 μmol) was dissolved in a mixed solution of tetrahydrofuran (2 mL), ethanol (1 mL) and water (2 mL), and sodium hydroxide (42.06 mg, 1.05 mmol) was added. The mixture was reacted at 60° C. for 2 hours. After the reaction was completed, the reaction solution was concentrated, diluted with 3 mL of water, adjusted to a pH of 5 with 1 M hydrochloric acid in water, and concentrated under reduced pressure. The resulting crude product was separated by high performance liquid chromatography (Column: Phenomenex luna C18 150×25 mm×10 m; Mobile phase: 0.225% formic acid in water-acetonitrile; Gradient: 34%-64% acetonitrile, 10 min) to give compound 34.

MS-ESI calculated $[M+H]^+$ 519, found 519.

$^1H$ NMR (400 MHz, $CD_3OD$) δ=7.68-7.52 (m, 5H), 7.16-7.09 (m, 1H), 5.19-5.14 (m, 2H), 5.12-5.05 (m, 1H), 4.98-4.92 (m, 1H), 3.29-2.98 (m, 4H), 2.70-2.65 (m, 3H), 2.64-2.36 (m, 4H), 2.29-2.20 (m, 3H), 2.01-1.57 (m, 9H).

Example 35

35

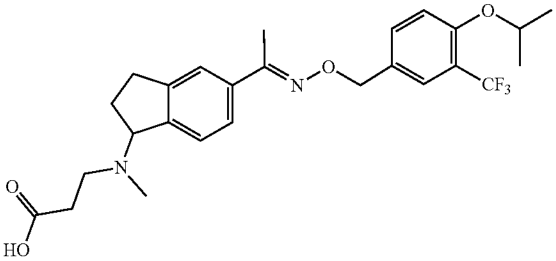

Synthetic Route:

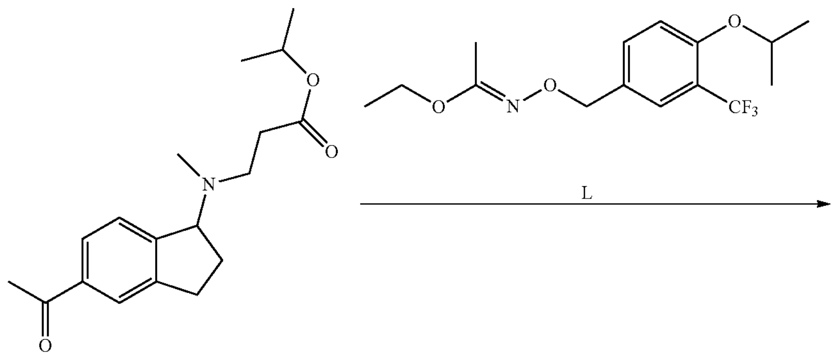

M

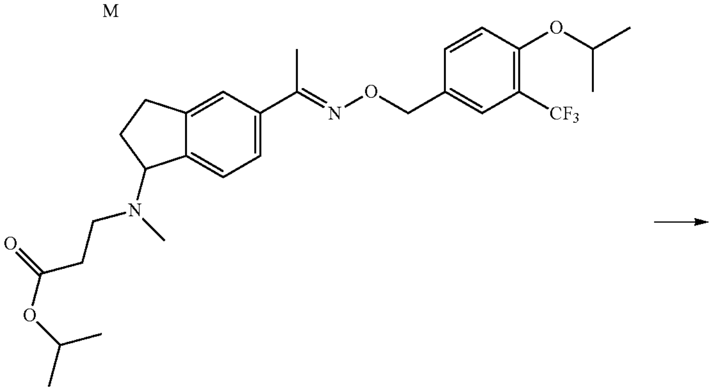

35-1

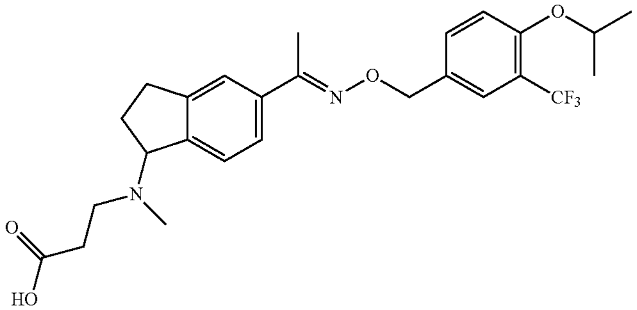

35

Step 1: Synthesis of Compound 35-1

To a solution of intermediate L (157.87 mg, 494.40 μmol) in methanol (5 mL) was added hydrochloric acid/ethyl acetate (4 M, 1.24 mL, 4.94 mmol), and the reaction solution was reacted at 20° C. for 0.5 hours. Triethylamine (400 mg, 3.96 mmol) was added dropwise to the reaction solution, and intermediate M (150 mg, 494 μmol) was added. The reaction solution was reacted at 60° C. for 3 hours. The reaction solution was diluted with water (50 mL). The aqueous phase was extracted with ethyl acetate (50 mL×1). The organic phases were combined, dried over anhydrous sodium sulfate, and filtered. The filtrate was concentrated under reduced pressure, and the resulting crude product was separated by thin-layer chromatography (dichloromethane/methanol, 10/1, V/V) to give compound 35-1.

MS-ESI calculated $[M+H]^+$ 535, found 535.

Step 2: Synthesis of Compound 35

Compound 35-1 (86 mg, 160.87 μmol) was dissolved in a mixed solution of tetrahydrofuran (2 mL), ethanol (1 mL) and water (2 mL), and sodium hydroxide (12.87 mg, 321.73 mmol) was added. The mixture was reacted at 60° C. for 2 hours. After the reaction was completed, the reaction solution was concentrated, diluted with 2 mL of water, adjusted to a pH of 6 with 1 M hydrochloric acid in water, and concentrated under reduced pressure. The resulting crude product was separated by high performance liquid chromatography (Column: Phenomenex luna C18 75x30 mmx3 m; Mobile phase: 0.225% formic acid in water-acetonitrile; Gradient: 40%-50% acetonitrile, 7 min) to give compound 35.

MS-ESI calculated $[M+H]^+$ 493, found 493.

$^1$H NMR (400 MHz, $CD_3OD$) δ=7.73-7.49 (m, 5H), 7.16 (d, J=8.4 Hz, 1H), 5.16 (s, 2H), 5.11-5.05 (m, 1H), 4.79-4.68 (m, 1H), 3.29-2.98 (m, 4H), 2.67 (s, 3H), 2.64-2.36 (m, 4H), 2.25 (s, 3H), 1.34 (d, J=6.1 Hz, 6H).

Biological Activity:

Assay Example 1: In Vitro Evaluation of the Agonistic Activity of the Compounds of the Present Disclosure on $S1P_1$ Object of the assay: To detect the agonistic activity of compounds on $S1P_1$ I. Cell Processing 1. Cells U2OS-EDG1 (Batch No.: Invitrogen-K1520) were taken out of a liquid nitrogen tank and placed in a 37° C. water bath to thaw quickly;
2. The cell suspension was aspirated into a 15 ml centrifuge tube, resuspended in 5 ml of preheated medium, and centrifuged at 1000 rpm for 5 min;
3. The supernatant was discarded. The cells were resuspended in 10 ml of medium, transferred into a T75 culture flask, and cultivated in an incubator with 5% $CO_2$ at 37° C.

II. Agonist Assay

1. The compounds were diluted to working concentrations, and serially diluted 3-fold by Echo 555 (manufacturer: Labcyte) to obtain 10 concentrations; 200 nL of each concentration of the compound was transferred to a cell plate and centrifuged at 1000 rpm for 15 seconds;
2. Culture medium was aspirated from the culture flask; 4 mL of Dulbecco's phosphate buffer (DPBS, supplier: Coring, item No.: 21-031-CVR, batch No.: 03318006) was added, and the residual serum was washed away; 2 mL of trypsin was added; The mixture was incubated in an incubator at 37° C. for 2 min, and the cells were digested; 10 mL of seeding medium was added to resuspend the cells; 0.6 mL of cell suspension was taken out and counted;
3. The density of cells was adjusted to 1.88E+05 cells/mL using seeding medium, with 40 μL per well (7500\well); 40 μL of FreeStyle™ Expression medium was added around the cell plate; The plate was let stand at room temperature for 15 min and incubated at 37° C. with 5% $CO_2$ for 20 hours.

III. Signal Detection

1. LiveBLAzer™-FRET B/G Substrate (CCF4-AM) assay reagents were formulated according to the instructions;
2. 8 μL of 6×Substrate Mixture was added to each well of the cell plate; The plate was centrifuged at 1000 rpm for 15 seconds, covered with a film, and incubated at 23° C. for 2 hours; The cell plate was subjected to Envision chemiluminescence detection.

IV. Data Analysis

1. The raw data were converted into % Effect by using an equation, and the $EC_{50}$ value can be obtained by curve fitting with four parameters ["log(agonist) vs. response—Variable slope" model in GraphPad Prism];
2. Calculation formula:

$$\text{Ratio}=(460\text{ nm}-\text{blank})/(535\text{ nm}-\text{blank})$$

$$\%\text{ Effect}=(\text{Sample}_{Ratio}-\text{Ave }LC_{Ratio})/(\text{Ave }HC_{Ratio}-\text{Ave }LC_{Ratio})\times 100\%$$

The assay results are shown in Table 1.

TABLE 1

Assay results of agonistic activity on $S1P_1$

| Assay sample | $EC_{50}$ of agonistic activity on $S1P_1$, Emax |
| --- | --- |
| Compound 1 trifluoroacetate | 41.56 nM, 88.4% |
| Compound 3 trifluoroacetate | 5.77 nM, 95% |
| Compound 10 hydrochloride | 57.18 nM, 84.2% |
| Compound 11 trifluoroacetate | 4.97 nM, 97.4% |
| Compound 13 hydrochloride | 14.06 nM, 102.2% |
| Compound 14 hydrochloride | 27.37 nM, 113.2% |
| Compound 20 | 8.92 nM, 51.0% |
| Compound 21 | 12.30 nM, 105.5% |
| Compound 22 formate | 19.23 nM, 107.3% |
| Compound 28 | 23.09 nM, 120.7% |
| Compound 29 | 8.62 nM, 102.8% |
| Compound 30 | 16.50 nM, 63.4% |
| Compound 31 | 10.27 nM, 105.0% |
| Compound 32 | 2.30 nM, 98.6% |
| Compound 32A | 3.84 nM, 101.4% |
| Compound 32B | 1.15 nM, 103.4% |
| Compound 33 | 2.98 nM, 109.9% |
| Compound 35 | 6.88 nM, 100.7% |

Conclusion: The compounds of the present disclosure all have significant or even unexpected agonistic activity on $S1P_1$.

Assay Example 2: Pharmacokinetic Evaluation of Compounds in Rats

Object of the assay: To evaluate the in vivo pharmacokinetics of the compounds in SD rats Materials of the Assay:

Sprague Dawley rats (male, 200-300 g, 7-9 weeks old, Shanghai SLAC)

Procedures of the Assay:

The pharmacokinetic characteristics of the compounds in rodents after intravenous injection and oral administration were assayed according to the standard protocol. In the assay, the candidate compounds were formulated into clear solutions and administered to rats by single intravenous injection and oral administration. The vehicle for intravenous injection and oral administration was DMSO and 10% hydroxypropyl β-cyclodextrin in water (DMSO:10% hydroxypropyl β-cyclodextrin in water=5:95). Whole blood samples were collected within 48 hours, and centrifuged at 3000 g for 15 minutes. The supernatant was separated to give plasma samples. 4 times the volume of acetonitrile solution containing internal standard was added to precipitate protein. The resulting mixture was centrifuged and the supernatant was taken out. An equal volume of water was added and the mixture was centrifuged. The supernatant was taken out, and injected as a sample to quantitatively analyze the plasma drug concentration by LC-MS/MS analysis method. The pharmacokinetic parameters, such as peak concentration, time to peak, clearance rate, half-life, area under drug-time curve, bioavailability, etc., were calculated.

The assay results are shown in Table 2.

TABLE 2

| Results of the pharmacokinetic assay | | | | | | |
|---|---|---|---|---|---|---|
| Assay sample | Peak concentration Cmax (nmol/L) | Clearance rate CL (mL/min/kg) | Distribution in tissue Vdss (L/kg) | Half life $T_{1/2}$ (PO, h) | Area under drug-time curve AUC0-last PO (nM · hr) | Bioavailability F (%) |
| Compound 3 trifluoroacetate (iv 1.4, po 2.7 mg/kg) | 393 | 6.87 | 5.47 | 11.3 | 7051 | 59.3 |
| Compound 11 trifluoroacetate (iv 1.2, po 2.4 mg/kg) | 605 | 4.24 | 3.32 | 9.08 | 11255 | 64.0 |
| Compound 21 (iv 1.0, po 2.0 mg/kg) | 486 | 5.43 | 2.05 | ND | 6135 | 53.2 |
| Compound 29 (iv 1.0, po 2.0 mg/kg) | 615 | 3.68 | 2.24 | ND | 9518 | 59.4 |
| Compound 30 (iv 1.0, po 2.0 mg/kg) | 478 | 3.93 | 4.19 | ND | 7542 | 62.1 |
| Compound 31 (iv 1.0, po 2.0 mg/kg) | 1665 | 2.87 | 0.88 | 4.6 | 18564 | 80.9 |
| Compound 32 (iv 1.0, po 2.0 mg/kg) | 556 | 11.3 | 4.35 | 5.44 | 5469 | 92.7 |
| Compound 32A (iv 1.0 mg/kg) | / | 4.5 | 2.78 | 7.5 | 6844* | / |
| Compound 32B (iv 1.0 mg/kg) | / | 3.97 | 2.7 | 8.3 | 7483* | / |

ND: Not determined, /: Not determined without relevant assay.
*Area under drug-time curve $AUC_{0\text{-}last}$ iv (nM · hr)

Conclusion: The compounds of the present disclosure show good bioavailability, high area under drug-time curve and low clearance rate in the assay of pharmacokinetics in SD rats.

Assay Example 3: Pharmacodynamic Evaluation of the Compound in Ischemia-Reperfusion Cerebral Infarction Model in Male SD Rats Object of the assay: pharmacodynamic assay to explore the improvement of compound 32 on the ischemia-reperfusion cerebral infarction model in rats Materials of the assay: male SD rats (250 g-280 g, SPF grade, Zhejiang Vital River Laboratory Animal Technology Co., Ltd.)

Procedures of the Assay:

1) Anesthesia: Respiratory anesthesia with 2.5% isoflurane was used to maintain the depth of anesthesia for animals.
2) Middle Cerebral Artery Occlusion (MCAO) Model: Animals weighed in the range of 250-280 g at the time of modeling surgery. After rats were anesthetized, the left common carotid artery was exposed under aseptic conditions in a supine position, and a special nylon suture was inserted through the left internal carotid artery to block the left middle cerebral artery and achieve a 90-min transient ischemia-reperfusion model of the left brain. After anesthesia, the animals in the Sham group exposed the left common carotid artery, but no suture was inserted, and meloxicam was injected subcutaneously, 1 mg/kg, once a day for 3 consecutive days. For the administration of the assay sample group, compound 32 was injected through the tail vein of rats after reperfusion with a dose of 1 mg/kg and a volume of 5 mL/kg.
3) Success criteria for the model:

1: Within 60 minutes after surgery, the animals were scored according to the Bederson method, and the animals with a score of 2-3 were included in the group.

2: Within 30-60 minutes of modeling, if the cerebral blood flow on the model side (left side) was reduced by more than 30% compared with that on the right side, the model was considered successful, and the animal was included in the group. If the reduction in blood flow was less than 30%, the model was considered unsuccessful and the animal was culled.

4) Detection index: the percentage of cerebral infarction at the end of the assay Evaluation of area of cerebral infarction: On the end day of the assay, the animals were euthanized. The brain was taken out, coronally sectioned with equal thickness (3 mm each, 5 slices in total), and stained with TTC staining solution (2%); the stained brain slices were scanned and imaged on both sides for the analysis of the cerebral infarction area. Brain tissues were then fixed with 10% formalin. The percentage of left cerebral infarct area is shown in FIG. 1.

The assay results are shown in Table 3, P<0.05 (compound 32 vs. the model group) in T-test.

TABLE 3

| Group | Percentage of left cerebral infarct area |
|---|---|
| Sham group | 0 |
| Model group | 32.4% |
| Compound 32 | 21.0% |

Conclusion: compared with the model group, the compound of the present disclosure can significantly improve the area of cerebral infarct in the ischemia-reperfusion model.

Assay Example 4: Analysis and Identification of Metabolites of the Compound in Human Liver Microsome and Hepatocyte Incubation System Object of the Assay:

By using high-resolution mass spectrometry, the metabolite produced by the incubation of compound 32B in human liver microsomes and human hepatocytes was found, and identified for its structure; the percentage content of compound 32B and its metabolite was calculated by using LC-UV; and the possible biotransformation pathway of compound 32B in human liver microsomes and human hepatocytes in vitro was studied.

Procedures of the Assay:

Compound 32B (10 μM) was incubated in a system containing both of human liver microsomes and NADPH at 37° C. for 60 min. 7-ethoxycoumarin (7-EC, 10 μM) was used as a positive control to evaluate the enzymatic metabolic activity in the liver microsome incubation system. The incubated sample was analyzed by LC-UV-HRMS. The structure of each metabolite was resolved and identified based on its primary and secondary mass spectrometry signals and/or comparison with a standard. The relative percentage of the UV-integrated peak area of each metabolite was given through data collected from the sample by LC-UV-HRMS, and the possible structure of the metabolite and its possible metabolic pathway in various genera of liver microsomes were inferred from the mass spectrometry information of the metabolite.

Compound 32B (10 μM) was incubated in mouse, rat, canine, monkey, and human hepatocyte systems at 37° C. for 120 min. 7-ethoxycoumarin (7-EC, 30 μM) was used as a positive control to evaluate the enzymatic metabolic activity in the hepatocyte incubation system. The incubated sample was analyzed by LC-UV-MS. The structure of each metabolite was resolved and identified based on its primary and secondary mass spectrometry signals and/or comparison with a standard. The relative percentage of the UV-integrated peak area of each metabolite was given through data collected from the sample by HPLC-UV-MS, and the possible structure of the metabolite and its possible metabolic pathway in various genera of hepatocytes were inferred from the mass spectrometry information of the metabolite.

Assay results: After incubation of compound 32B with human liver microsomes for 1 hour, the original drug was the main component with a relative abundance of 100.00%; no other metabolite was detected. After incubation of compound 32B with human hepatocytes for 2 hours, compound 32B mainly existed in the form of the original drug, with a relative abundance of 100.00%, and no other metabolite was detected.

Conclusion: the compound of the present disclosure has good metabolic stability.

Assay Example 5: In Vitro Evaluation of the Agonistic Activity of the Compound of the Present Disclosure on $S1P_2$, $S1P_3$ and $S1P_4$ Object of the assay: To detect the agonistic activity of the compound on $S1P_2$, $S1P_3$, and $S1P_4$ I. Cell Processing 1. PathHunter cell line was expanded from freezer according to standard procedures.
2. Cells were seeded into a white 384-well microplate in a total volume of 20 μL and incubated at 37° C. for an appropriate time prior to testing.

II. Agonist Assay

1. For the agonist assay, cells were incubated with a sample to induce a response.
2. Stock solution was stored in a buffer at a concentration of 5 times the concentration to be tested.
3. 5 μl of the stock solution sample at a concentration of 5 times the concentration to be tested was added to the cells and incubated at 37° C. or room temperature for 90-180 min with a vehicle concentration of 1%.

III. Signal Detection

1. A single addition of 12.5 or 15 microliters (50% v/v) of PathHunter Detection reagent mixture was used to generate the assay signal, and the mixture was incubated at room temperature for 1 hour.
2. Chemiluminescent Signal detection was performed using a PerkinElmer Envision™ instrument, and the microplate was read after signal generation.

IV. Data Analysis

1. The activity of the compound was analyzed using the CBIS data analysis suite (ChemInnovation, CA).
2. For the agonist mode assay, the percent activity was calculated using the following formula:

% Activity=100%×(Mean RLU of the Assay Sample−Mean RLU of the Blank Control)/(Mean MAX Control Ligand−Mean RLU of the Blank Control).

The assay results are shown in Table 4.

TABLE 4

| | $S1P_2$ agonistic activity $EC_{50}$ | $S1P_3$ agonistic activity $EC_{50}$ | $S1P_4$ agonistic activity $EC_{50}$ |
|---|---|---|---|
| Compound 32B | >300 nM | >300 nM | >300 nM |

Conclusion: the compound of the present disclosure has a weak agonistic activity on $S1P_2$, $S1P_3$, and $S1P_4$.

What is claimed is:

1. A compound represented by formula (II) or a pharmaceutically acceptable salt thereof, (II)

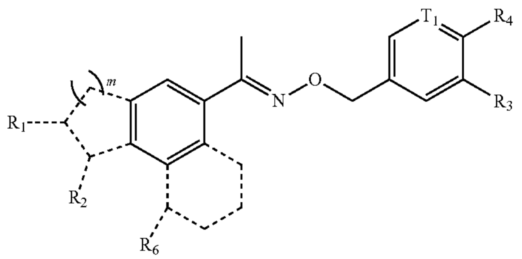

wherein the structural moiety

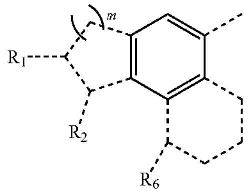

is selected from

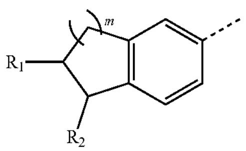 and 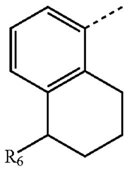 ;

m is selected from 1 and 2;

$T_1$ is selected from $CR_5$ and N;

$R_1$ and $R_2$ are each independently selected from H, $-L_1-NR_a-L_2-COOH$, $-L_1-NR_a-L_2$-cyclopropyl, -azetidinyl-COOH and -piperidyl-COOH, wherein the $-L_1-NR_a-L_2-COOH$, $-L_1-NR_a-L_2$-cyclopropyl, -azetidinyl-COOH and -piperidyl-COOH are optionally substituted with 1, 2 or 3 $R_b$;

$L_1$ is selected from a single bond or $CH_2$;

$L_2$ is $C_{1-3}$ alkyl;

$R_3$ and $R_5$ are each independently selected from H, F, Cl, Br, CN and $C_{1-3}$ alkyl, wherein the $C_{1-3}$ alkyl is optionally substituted with 1, 2 or 3 $R_c$;

$R_4$ is selected from —O—$C_{1-6}$ alkyl, —O—$C_{1-3}$ alkyl-cyclopropyl, —O—$C_{3-6}$ cycloalkyl and $C_{3-6}$ cycloalkyl, wherein the $C_{1-3}$ alkyl, $C_{1-6}$ alkyl and $C_{3-6}$ cycloalkyl are optionally substituted with 1, 2 or 3 $R_d$;

$R_6$ is selected from H and —$NR_a$—$C_{1-3}$ alkyl-COOH, wherein the —$NR_a$—$C_{1-3}$ alkyl-COOH is optionally substituted with 1, 2 or 3 $R_e$;

$R_a$ is selected from H and $CH_3$;

$R_b$ is selected from H, F, Cl, Br, I and COOH;

$R_c$ and $R_d$ are each independently selected from H, F, Cl, Br and I;

$R_e$ is each independently selected from H, F, Cl, Br and I.

2. The compound according to claim 1, or a pharmaceutically acceptable salt thereof, wherein $R_1$ is selected from H, —NH—$CH_2$—COOH and —NH—$CH_2CH_2$—COOH.

3. The compound according to claim 1, or a pharmaceutically acceptable salt thereof, wherein $L_2$ is selected from $CH_2$, $CH_2CH_2$, $C(CH_3)_2$ and $CH_2CH_2CH_2$.

4. The compound according to claim 1, or a pharmaceutically acceptable salt thereof, wherein $R_2$ is selected from H, —NH—$CH_2$—COOH, —NH—$CH_2CH_2$—COOH, —$N(CH_3)$—$CH_2CH_2$—COOH,

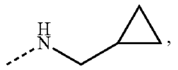, 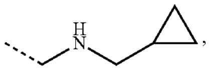,

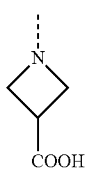 and 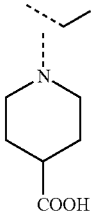 , wherein the —NH—$CH_2$—COOH, —NH—$CH_2CH_2$—COOH, —$N(CH_3)$—$CH_2CH_2$—COOH,

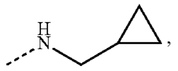, 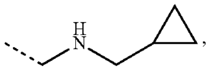,

-continued

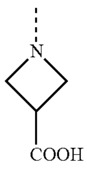 and 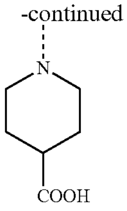

are optionally substituted with 1, 2 or 3 $R_b$.

5. The compound according to claim 4, or a pharmaceutically acceptable salt thereof, wherein $R_2$ is selected from H, —NH—$CH_2$—COOH, —NH—$CH_2CH_2$—COOH, —$N(CH_3)$—$CH_2CH_2$—COOH,

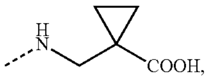, 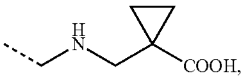,

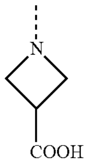 and 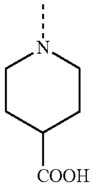 .

6. The compound according to claim 1, or a pharmaceutically acceptable salt thereof, wherein $R_3$ is selected from H, F, Cl, Br, CN and $CF_3$.

7. The compound according to claim 1, or a pharmaceutically acceptable salt thereof, wherein $R_4$ is selected from —O—$C_{1-4}$ alkyl, —O—$C_{1-3}$ alkyl-cyclopropyl, —O-cyclopropyl, —O-cyclopentyl and cyclohexyl, wherein the —O—$C_{1-4}$ alkyl, —O—$C_{1-3}$ alkyl-cyclopropyl, —O-cyclopropyl, —O-cyclopentyl and cyclohexyl are optionally substituted with 1, 2 or 3 $R_d$.

8. The compound according to claim 1, or a pharmaceutically acceptable salt thereof, wherein $R_4$ is selected from

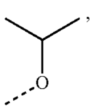, 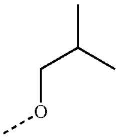, 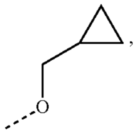,

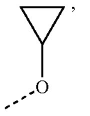, 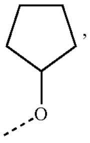, 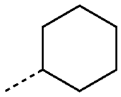 and 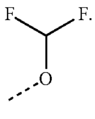.

9. The compound according to claim 1, or a pharmaceutically acceptable salt thereof, wherein $R_5$ is selected from H and F.

10. The compound according to claim 1, or a pharmaceutically acceptable salt thereof, wherein $R_6$ is selected from H, —NH—$CH_2$—COOH, —NH—$CH_2CH_2$—COOH, —$N(CH_3)$—$CH_2CH_2$—COOH and —NH—$(CH_2)_3$—COOH.

11. The compound according to claim 1, or a pharmaceutically acceptable salt thereof, wherein the compound is selected from (I)

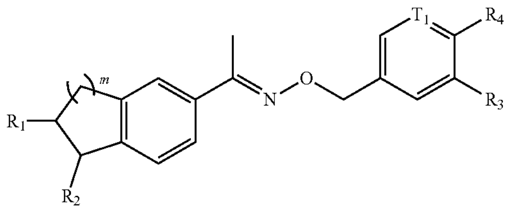

and (II-1)

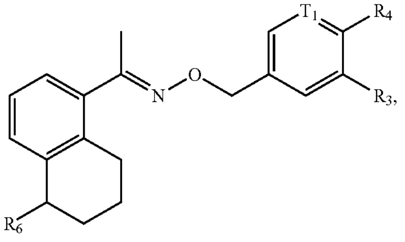

wherein m and $T_1$ are as defined in claim 1;

$R_1$ is as defined in claim 1;

$R_2$ is as defined in claim 1;

$R_3$ is as defined in claim 1;

$R_4$ is as defined in claim 1;

$R_6$ is as defined in claim 1.

12. The compound according to claim 11 or a pharmaceutically acceptable salt thereof, wherein the compound is selected from (I-1)

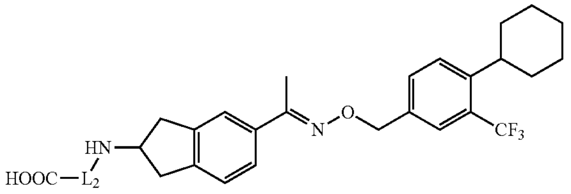

(I-2)

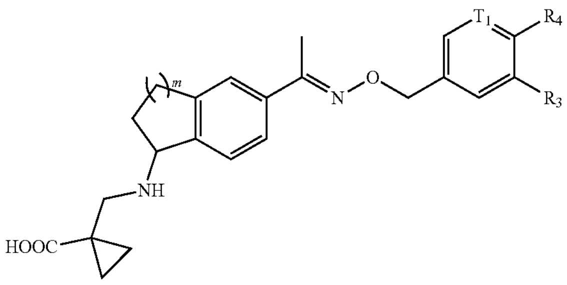

(I-3)

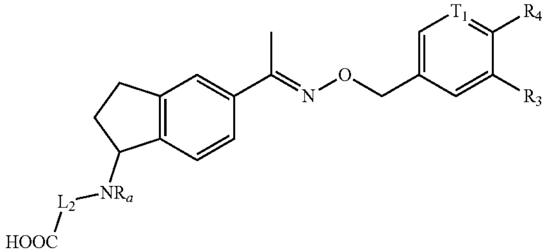

-continued (II-1-1)

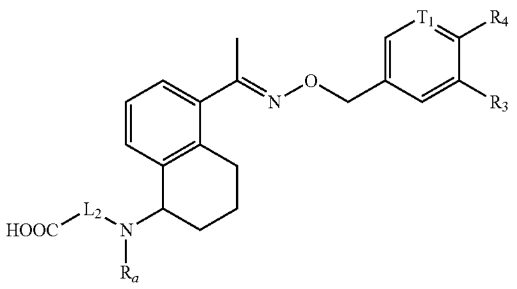

and (IV-1)

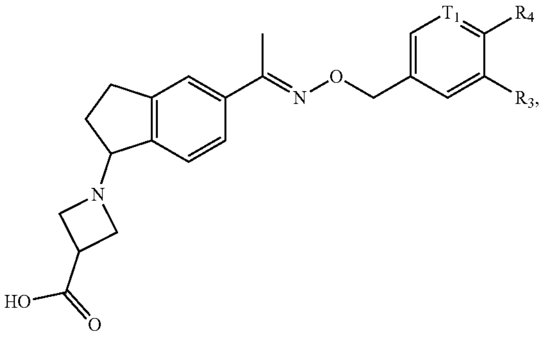

wherein $R_a$ is selected from H and $CH_3$;

m, $T_1$, $R_3$, and $R_4$ are as defined in claim 11;

$L_2$ is $C_{1-3}$ alkyl.

13. A compound represented by the following formula, or a pharmaceutically acceptable salt thereof,

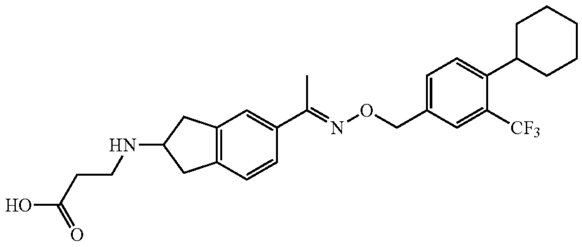

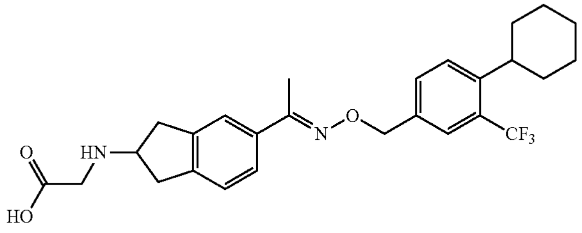

-continued
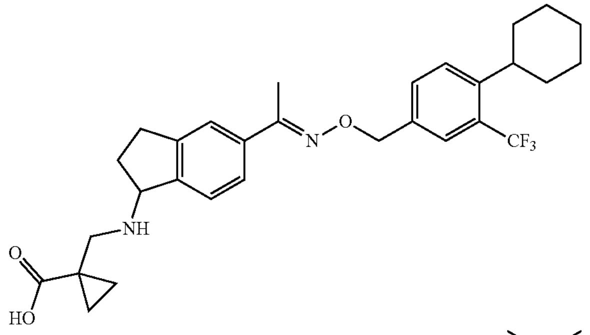
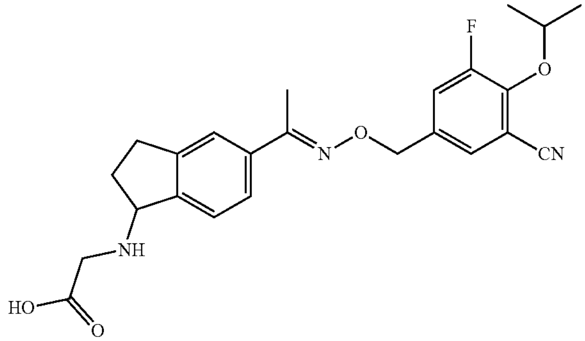
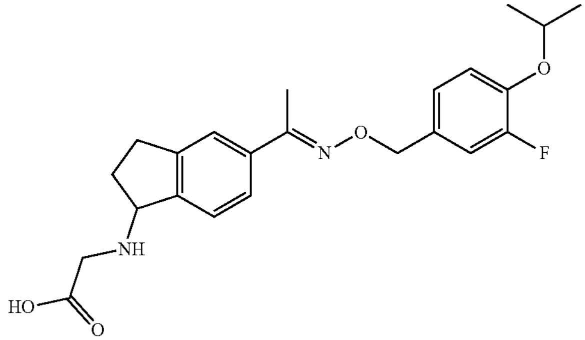
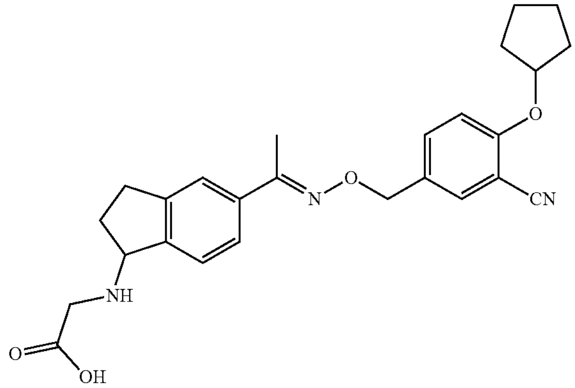
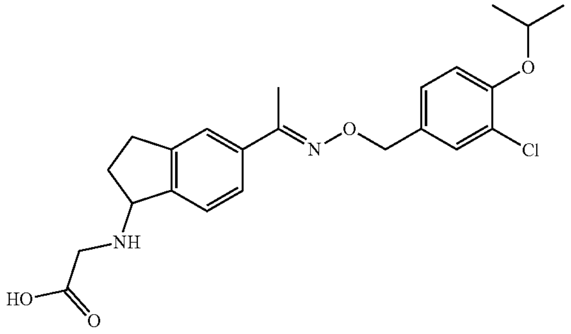
-continued
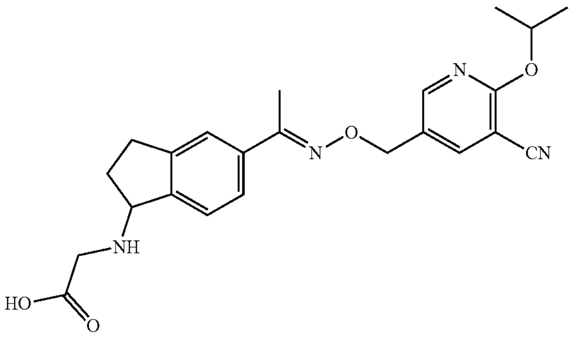
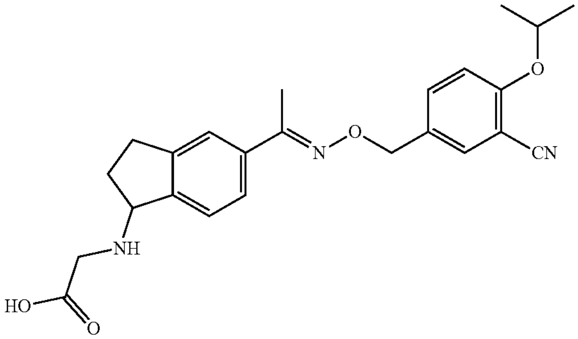
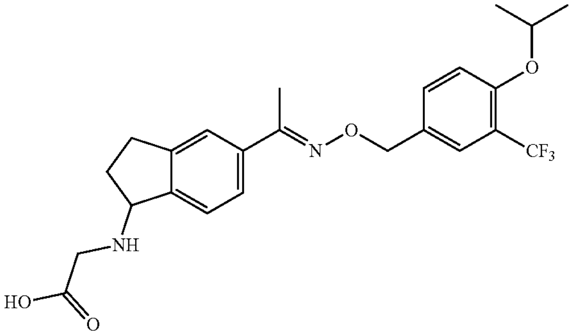
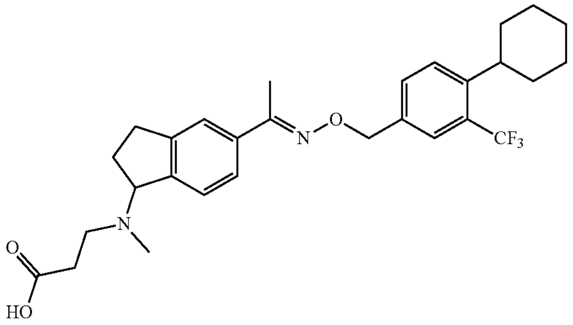
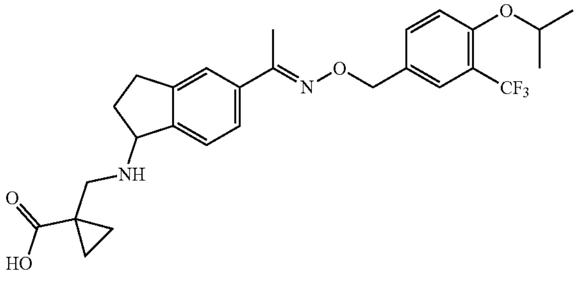

-continued
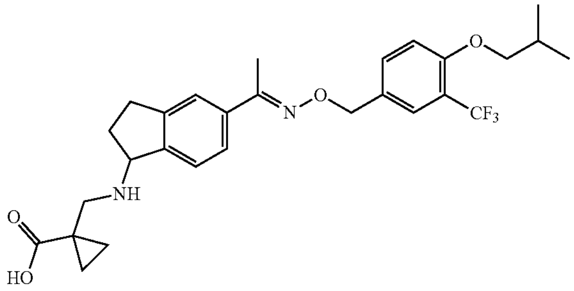
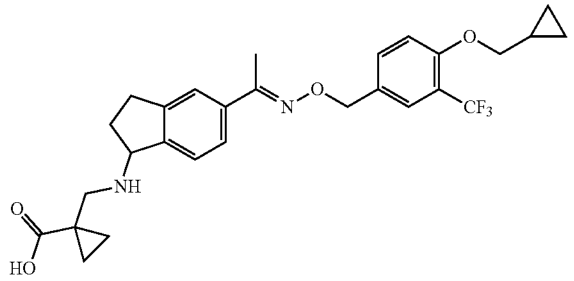
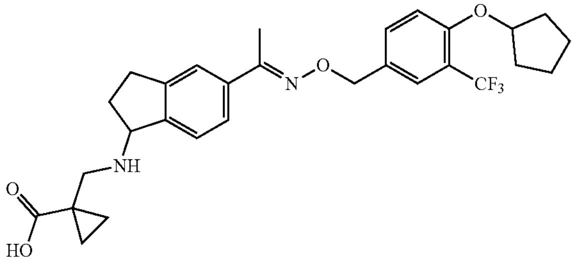
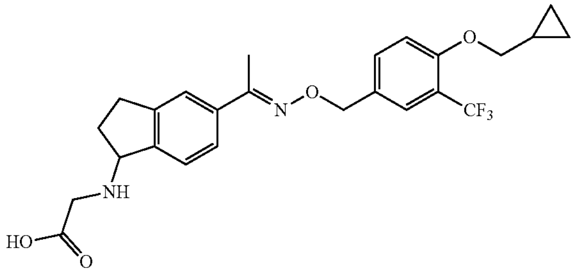
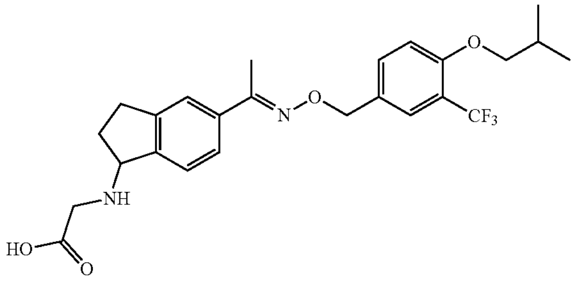
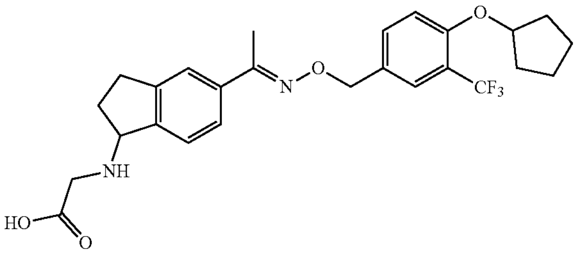
-continued
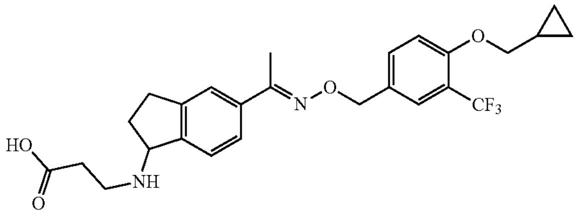
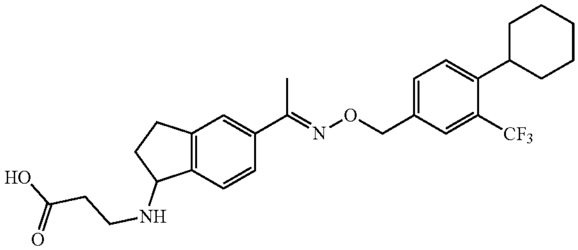
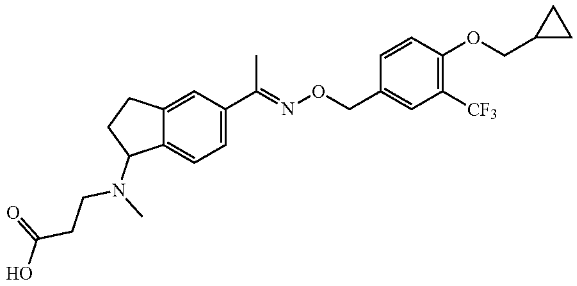
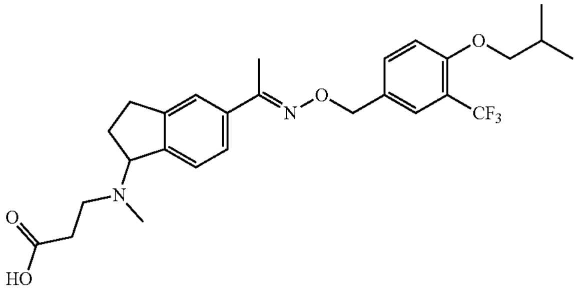
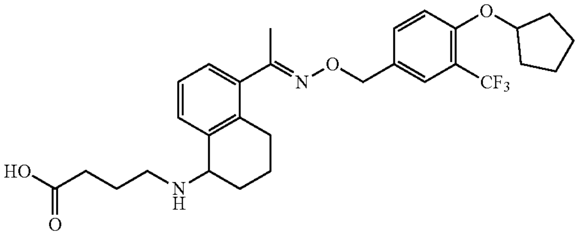
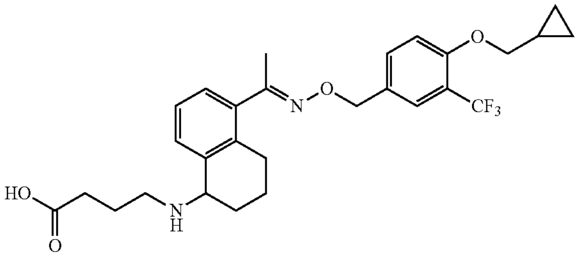

-continued
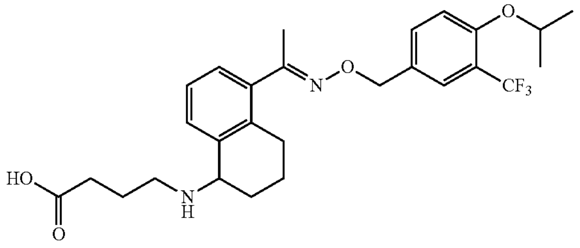
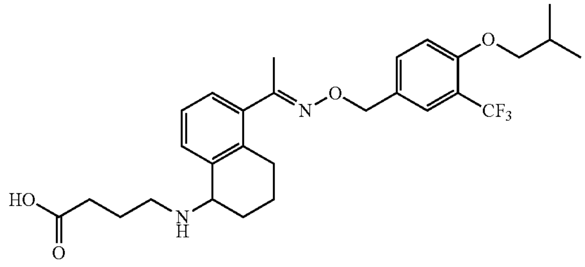
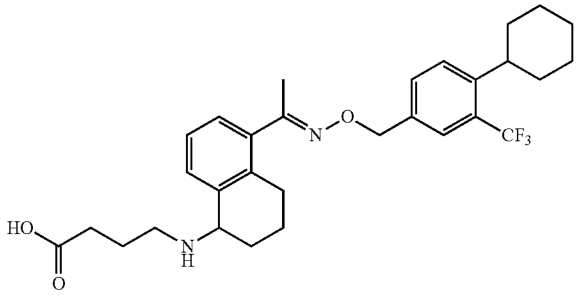
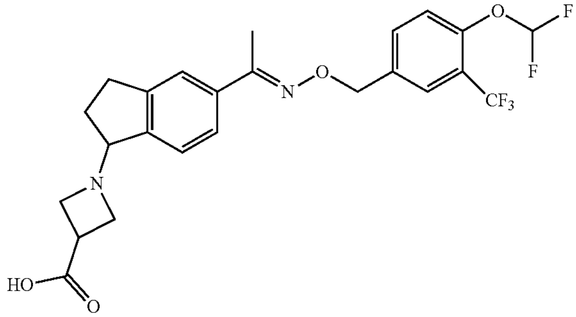
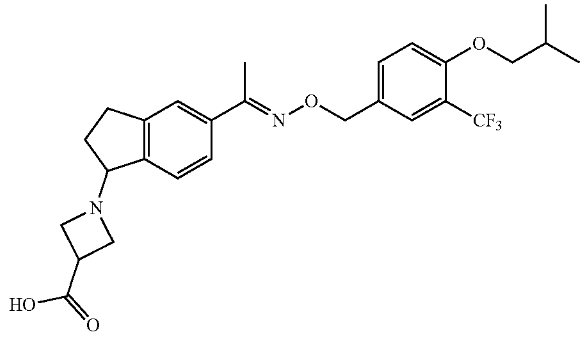
-continued
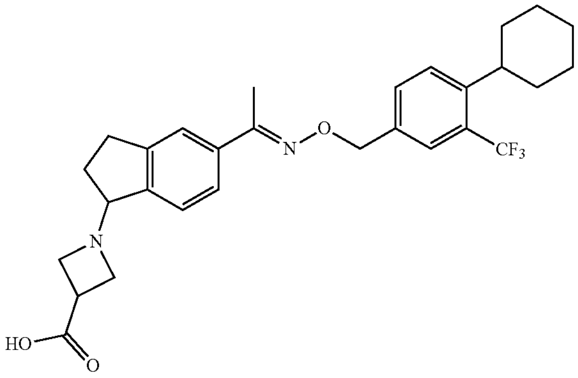
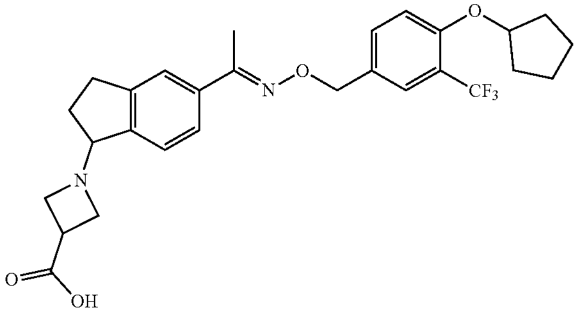
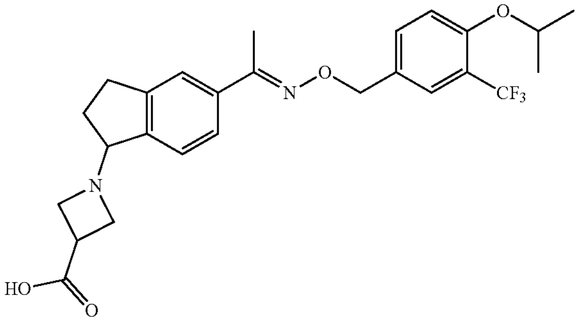
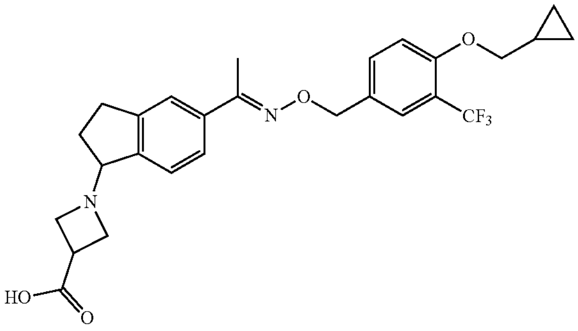
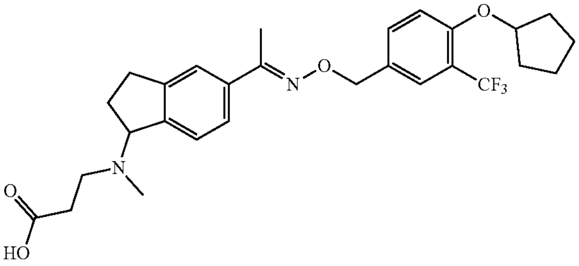

-continued
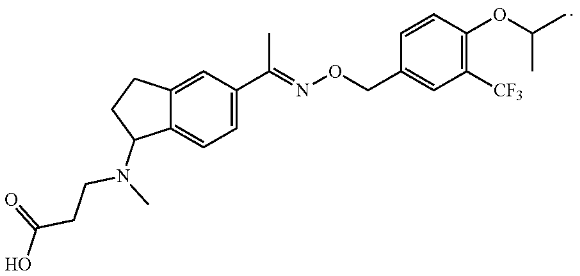
14. The compound according to claim 13, or a pharmaceutically acceptable salt thereof, wherein the compound is selected from
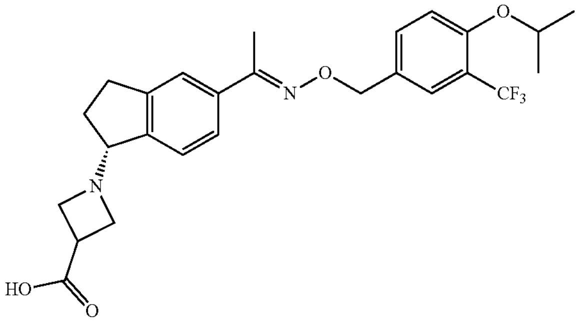
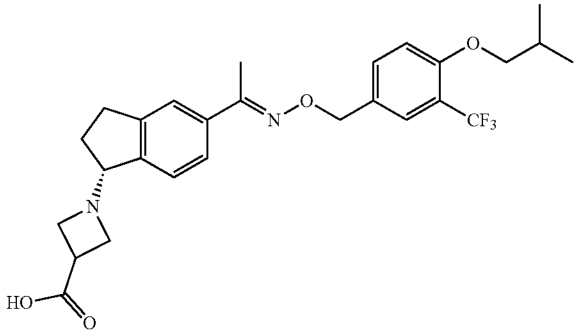
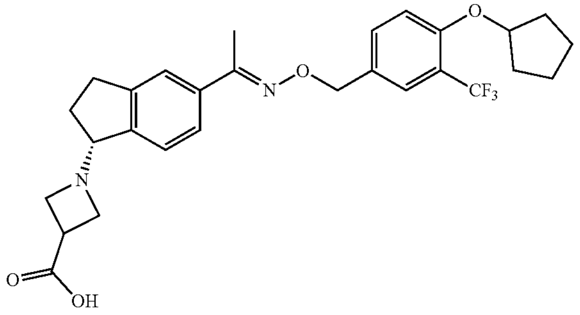
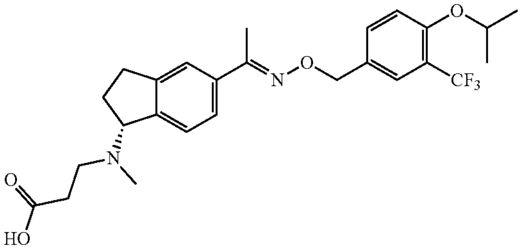
-continued
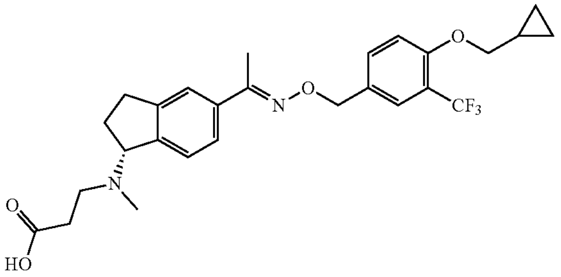
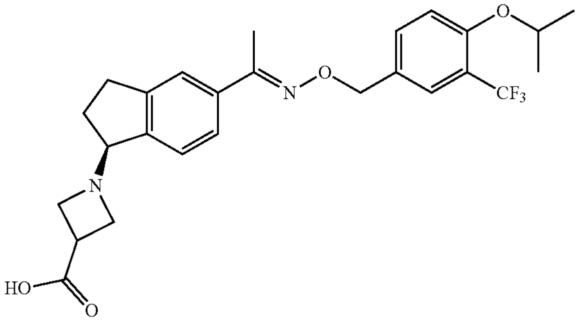
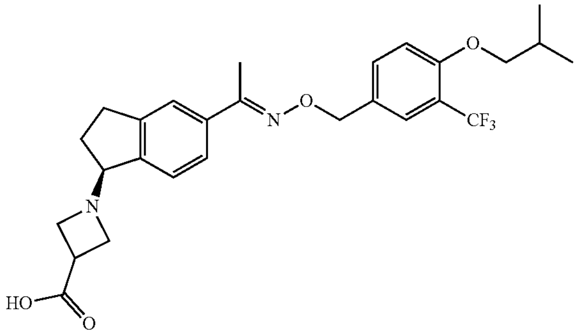
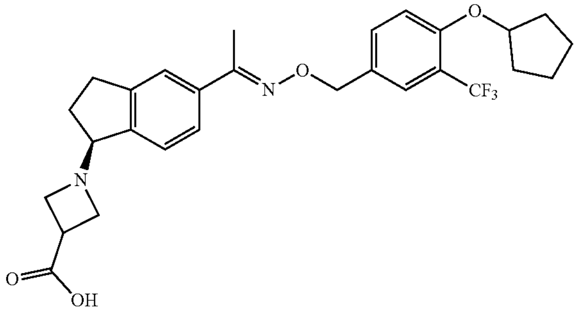
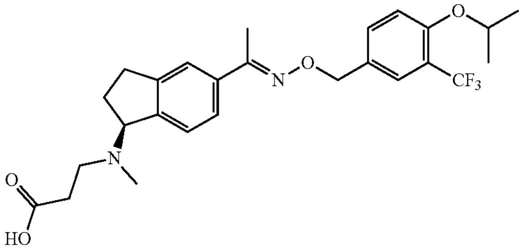
and -continued
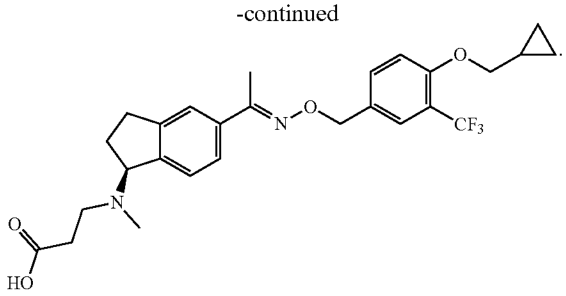
15. A method of treating ischemic stroke in a subject in need thereof, comprising administering to the subject the compound according to claim 1 or a pharmaceutically acceptable salt thereof.
* * * * *